United States Patent
Waddell et al.

(10) Patent No.: US 9,944,950 B2
(45) Date of Patent: Apr. 17, 2018

(54) METHODS AND COMPOSITIONS FOR PRODUCING INDUCED AIRWAY TISSUE PROGENITOR CELLS

(71) Applicants: Thomas K. Waddell, Toronto (CA); Li Guo, Toronto (CA); Andras Nagy, Toronto (CA)

(72) Inventors: Thomas K. Waddell, Toronto (CA); Li Guo, Toronto (CA); Andras Nagy, Toronto (CA)

( * ) Notice: Subject to any disclaimer, the term of this patent is extended or adjusted under 35 U.S.C. 154(b) by 0 days.

(21) Appl. No.: 14/295,004

(22) Filed: Jun. 3, 2014

(65) Prior Publication Data

US 2015/0004612 A1    Jan. 1, 2015

Related U.S. Application Data

(60) Provisional application No. 61/830,483, filed on Jun. 3, 2013.

(51) Int. Cl.
| | |
|---|---|
| *C12N 5/00* | (2006.01) |
| *C12N 15/00* | (2006.01) |
| *C12N 15/85* | (2006.01) |
| *C12N 5/074* | (2010.01) |
| *A61K 35/42* | (2015.01) |

(52) U.S. Cl.
CPC ........... *C12N 15/85* (2013.01); *C12N 5/0696* (2013.01); *A61K 35/42* (2013.01); *C12N 2501/602* (2013.01); *C12N 2501/603* (2013.01); *C12N 2501/604* (2013.01); *C12N 2501/605* (2013.01); *C12N 2501/608* (2013.01); *C12N 2506/27* (2013.01); *C12N 2830/003* (2013.01)

(58) Field of Classification Search
USPC ................................. 435/325, 455
See application file for complete search history.

(56) References Cited

U.S. PATENT DOCUMENTS

2011/0200568 A1*   8/2011   Ikeda .................... C12N 5/0696
                                                        424/93.21

OTHER PUBLICATIONS

Definition of epithelial cell adhsion molecule from Wikipedia, 2015.*
Somers (Stem Cells Oct. 2010, vol. 28, No. 10, p. 1728-1740).*
Raab (Stem Cells International, Nov. 6, 2014, p. 1-12).*
Carey (Nature Methods, Jan. 2010, vol. 7, No. 1, p. 56-59).*
Kesimer M., et al. (2009). Tracheobronchial air-liquid interface cell culture: a model for innate mucosal defense of the upper airways? American Journal of Physiology. Lung Cellular and Molecular Physiology, 296(1), L92-L100. doi:10.1152/ajplung.90388.2008.
Chilosi Mé, et al. (2010). Epithelial stem cell exhaustion in the pathogenesis of idiopathic pulmonary fibrosis. Sarcoidosis casculitis and diffuse lung diseases. 27; 7-18.
Marsh Leigh M., et al. (2009). Surface expression of CD74 by type II alveolar epithelial cells: a potential mechanism for macrophage migration inhibitory factor-induced epithelial repair. Am J Physiol Lung Cell Mol Physiol 296: L442-L452.
Rock, J. R., et al. (2009). Basal cells as stem cells of the mouse trachea and human airway epithelium. Proc. Natl. Acad. Sci. USA 106, 12771-12775.
Samavarchi-Tehrani Payman et al. (2010). Functional Genomics Reveals a BMP-Driven Mesenchymal-to-Epithelial Transition in the Initiation of Somatic Cell Reprogramming. Cell Stem Cell 7, 64-77.
Zemke Anna C., et al. (2009) Molecular staging of epithelial maturation using secretory cell—specific genes as markers. Am J Respir Cell Mol Biol vol. 40. pp. 340-348.
Woltjen, K. et al. (2009). PiggyBac transposition reprograms fibroblasts to induced pluripotent stem cells. Nature 458, 766-770.
Fehrenbach H., et al. (2001). Alveolar epithelial type II cell: defender of the alveolus revisited. Respir Res; 2: 33-46.
Berndt-Weis Lynn M. et al. (2009). Global transcriptional characterization of a mouse pulmonary epithelial cell line for use in genetic toxicology. Toxicology in Vitro 23, 816-833.
Jeffrey J Atkinson. et al. (2008). Clara cell adhesion and migration to extracellular matrix. Respiratory Research 10.1186/1465-9921-9-1.
Rawlins EL, Hogan BL. Epithelial stem cells of the lung: privileged few or opportunities for many? Development 2006; 133:2455-2465.
Okubo T. et al. Nmyc plays an essential role during lung development as a dosage-sensitive regulator of progenitor cell proliferation and differentiation. Development 2005; 132:1363-1374.
Wan H., et al. Compensatory roles of foxal and foxa2 during lung morphogenesis. J Biol Chem 2005;280:13809-13816.
Shu W., et al. Wnt/beta-catenin signaling acts upstream of n-myc, bmp4, and fgf signaling to regulate proximaldistal patterning in the lung. Dev Biol 2005; 283:226-239.
Lu Y. et al. Transgenic over-expression of the microrna mir-17-92 cluster promotes proliferation and inhibits differentiation of lung epithelial progenitor cells. Dev Biol 2007; 310:442-453.
Rupa S., et al. Role of the murine reprogramming factors in the induction of pluripotency. Cell 2009:136, 364-377.

(Continued)

*Primary Examiner* — Michael C Wilson
(74) *Attorney, Agent, or Firm* — Bereskin & Parr LLP; Carmela De Luca

(57) ABSTRACT

A method of generating an induced progenitor population (iPP) of cells and/or induced population of cells from somatic cells, comprising the steps:
a) obtaining a starting cell population, wherein cells of the starting cell population comprise, or are contacted with, a nucleic acid molecule encoding four reprogramming factors under the control of a control element, wherein the four reprogramming factors are optionally Oct4, Klf4, Sox2 and c-Myc, and wherein the control element prevents or stops expression of the reprogramming factors under its control in the absence of induction by an inducing agent; and
b) transiently inducing expression of the reprogramming factors in the starting cell population to obtain an iPP,
c) optionally isolating the iPP, and
d) terminating the transient induction while the proliferative capacity of the iPP remains under the control of the one or more exogenous reprogramming factors to produce an induced population of cells.

10 Claims, 31 Drawing Sheets

(56) References Cited

OTHER PUBLICATIONS

Carey Bryce W., et al. A single-gene transgenic mouse strain for reprogramming adult somatic cells. Nature Methods 2010; 7(1): 56-59.

Kim Sinae, et al. A novel culture technique for human embryonic stem cells using porous membranes. Stem cell 2007; 25:2601-2609.

McQualter et al. Evidence of an epithelial stem/progenitor cell hierarchy in the adult mouse lung. PNAS 2010; 107: 1414-1419.

Shulamit Levenberg et al. Differentiation of human embryonic stem cells on three-dimensional polymer scaffolds. PNAS 2003; 22: 12741-12746.

Stripp BR, et al. Plasticity of airway cell proliferation and gene expression after acute naphthalene injury. Am J Physiol 1995; 269(6 Pt 1): L791-9.

Yin L, et al. Induction of vascular progenitor cells from endothelial cells stimulates coronary collateral growth. Circ Res 2012; 110(2): 241-52.

Kim K., et al. Epigenetic memory in induced pluripotent stem cells. Nature 2010; 467(7313): 285-90.

Polo JM, et al. Cell type of origin influences the molecular and functional properties of mouse induced pluripotent cells. Nat Biotechnol 2010; 28(8): 848-55.

Herridge, M. S. et al. One-year outcomes in survivors of the acute respiratory distress syndrome. The New England journal of medicine 348, 683-693, doi:10.1056/NEJMoa022450 (2003).

Wiesen, J., et al. Relative cost and outcomes in the intensive care unit of acute lung injury (ALI) due to pandemic influenza compared with other etiologies: a single-center study. Annals of intensive care 2, 41, doi:10.1186/2110-5820-2-41 (2012).

Murray, C., et al. The global burden of disease in 1990: summary results, sensitivity analysis and future directions. Bulletin of the World Health Organization 72, 495-509 (1994).

Menzin, J., et al. Cost analysis of amlodipine versus enalapril in patients with coronary artery disease and normal blood pressure: findings from the CAMELOT economic substudy. Applied health economics and health policy 6, 157-162, doi:10.2165/00148365-200806020-00007 (2008).

Vasiliadis, H. M., et al. A cost-effectiveness and cost-utility study of lung transplantation. The Journal of heart and lung transplantation : the official publication of the International Society for Heart Transplantation 24, 1275-1283, doi:10.1016/j.healun.2004.10.012 (2005).

Bertoncello, I. & McQualter, J. L. Endogenous lung stem cells: what is their potential for use in regenerative medicine? Expert Rev Respir Med 4, 349-362 (2010).

Liu, X., et al. Stem cells in the lung. Methods in enzymology 419, 285-321 (2006).

Mou, H. et al. Generation of multipotent lung and airway progenitors from mouse ESCs and patient-specific cystic fibrosis iPSCs. Cell Stem Cell 10, 385-397 (2012).

Wong, A. P. et al. Directed differentiation of human pluripotent stem cells into mature airway epithelia expressing functional CFTRTR protein. Nat. Biotechnol. 30, 876-882 (2012).

Sridharan, R. et al. Role of the Murine Reprogramming Factors in the Induction of Pluripotency. Cell 136, 364-377 (2009).

Rawlins, E. L. et al. The Role of Scgb1a1+ Clara Cells in the Long-Term Maintenance and Repair of Lung Airway, but Not Alveolar, Epithelium. Cell Stem Cell 4, 525-534 (2009).

Wernig, M. et al. A drug-inducible transgenic system for direct reprogramming of multiple somatic cell types. Nat. Biotechnol. 26, 916-924 (2008).

Shao, L. et al. Generation of iPS cells using defined factors linked via the self-cleaving 2A sequences in a single open reading frame. Cell Res. 19, 296-306 (2009).

Eminli, S. et al. Differentiation stage determines potential of hematopoietic cells for reprogramming into induced pluripotent stem cells. Nat. Genet. 41, 968-976 (2009).

Hanna, J. et al. Direct cell reprogramming is a stochastic process amenable to acceleration. Nature 462, 595-601 (2009).

Hackett, B. P. & Gitlin, J. D. Cell-specific expression of a Clara cell secretory protein-human growth hormone gene in the bronchiolar epithelium of transgenic mice. Proc. Natl. Acad. Sci. U.S.A. 89, 9079-9083 (1992).

Tsao, P.-N. et al. Notch signaling controls the balance of ciliated and secretory cell fates in developing airways. Development 136, 2297-2307 (2009).

Williams, M. C., Cao, Y., Hinds, A., Rishi, A. K. & Wetterwald, A. T1 alpha protein is developmentally regulated and expressed by alveolar type I cells, choroid plexus, and ciliary epithelia of adult rats. Am. J. Respir. Cell Mol. Biol. 14, 577-585 (1996).

Rawlins, E. L. & Hogan, B. L. M. Ciliated epithelial cell lifespan in the mouse trachea and lung. AJP: Lung Cellular and Molecular Physiology 295, L231-L234 (2008).

Parish, C. R. Fluorescent dyes for lymphocyte migration and proliferation studies. Immunol. Cell Biol. 77, 499-508 (1999).

Benharouga, M. The Role of the C Terminus and Na+/H+ Exchanger Regulatory Factor in the Functional Expression of Cystic Fibrosis Transmembrane Conductance Regulator in Nonpolarized Cells and Epithelia. Journal of Biological Chemistry 278, 22079-22089 (2003).

Duchesneau, P., Wong, A. P. & Waddell, T. K. Optimization of Targeted Cell Replacement Therapy: A New Approach for Lung Disease. Molecular Therapy 18, 1830-1836 (2010).

Amabile, G. & Meissner, A. Induced pluripotent stem cells: current progress and potential for regenerative medicine. Trends Mol Med 15, 59-68 (2009).

Wu, S. M. & Hochedlinger, K. Harnessing the potential of induced pluripotent stem cells for regenerative medicine. Nat. Cell Biol. 13, 497-505 (2011).

Sommer, C. A. & Mostoslaysky, G. The evolving field of induced pluripotency: recent progress and future challenges. J. Cell. Physiol. 228, 267-275 (2013).

Plath, K. & Lowry, W. E. Progress in understanding reprogramming to the induced pluripotent state. Nat. Rev. Genet. 12, 253-265 (2011).

Ben-David, U. & Benvenisty, N. The tumorigenicity of human embryonic and induced pluripotent stem cells. Nat. Rev. Cancer 11, 268-277 (2011).

Pfisterer, U. et al. Direct conversion of human fibroblasts to dopaminergic neurons. Proc. Natl. Acad. Sci. U.S.A. 108, 10343-10348 (2011).

Caiazzo, M. et al. Direct generation of functional dopaminergic neurons from mouse and human fibroblasts. Nature 476, 224-227 (2011).

Ambasudhan, R. et al. Direct reprogramming of adult human fibroblasts to functional neurons under defined conditions. Cell Stem Cell 9, 113-118 (2011).

Chin, M. H. et al. Induced pluripotent stem cells and embryonic stem cells are distinguished by gene expression signatures. Cell Stem Cell 5, 111-123 (2009).

Ghosh, Z. et al. Persistent Donor Cell Gene Expression among Human Induced Pluripotent Stem Cells Contributes to Differences with Human Embryonic Stem Cells. PLoS ONE 5, e8975 (2010).

Marchetto, M. C. N. et al. Transcriptional Signature and Memory Retention of Human-Induced Pluripotent Stem Cells. PLoS ONE 4, e7076 (2009).

Denham, M. et al. A murine respiratory-inducing niche displays variable efficiency across human and mouse embryonic stem cell species. Am. J. Physiol. Lung Cell Mol. Physiol. 292, L1241-1247 (2007).

Rippon, H., et al. Initial observations on the effect of medium composition on the differentiation of murine embryonic stem cells to alveolar type II cells. Cloning Stem Cells 6, 49-56 (2004).

Van Vranken, Benjamin et al. The Differentiation of Distal Lung Epithelium from Embryonic Stem Cells. Current Protocols in Stem Cell Biology, 2007, 1G.1.1-1G.1.22.

Christodoulou, C. et al. Mouse ES and iPS cells can form similar definitive endoderm despite differences in imprinted genes. J. Clin. Invest. 121, 2313-2325 (2011).

Longmire, T. A. et al. Efficient derivation of purified lung and thyroid progenitors from embryonic stem cells. Cell Stem Cell 10, 398-411 (2012).

(56) References Cited

OTHER PUBLICATIONS

Brook B. Cole, et al. (2010) Tracheal Basal Cells A Facultative Progenitor Cell Pool Am J Pathol. 177(1): 362-376.

Lin, H., et al. (2007). Air-liquid interface (ALI) culture of human bronchial epithelial cell monolayers as an in vitro model for airway drug transport studies. J Pharm Sci. Feb. 2007;96(2):341-50.

Roszell, B. et al. Efficient derivation of alveolar type II cells from embryonic stem cells for in vivo application. Tissue Eng. Part A 15, 3351-3365 (2009).

Cortiella, J. et al. Tissue-engineered lung: an in vivo and in vitro comparison of polyglycolic acid and pluronic F-127 hydrogel/somatic lung progenitor cell constructs to support tissue growth. Tissue Eng. 12, 1213-1225 (2006).

Jensen, T. et al. A rapid lung de-cellularization protocol supports embryonic stem cell differentiation in vitro and following implantation. Tissue Eng. Part C Methods 18, 632-646 (2012).

Li, M. et al. Co-electrospun poly(lactide-co-glycolide), gelatin, and elastin blends for tissue engineering scaffolds. J. Biomed. Mater. Res. A 79, 963-973 (2006).

Takahashi, K. & Yamanaka, S. Induction of Pluripotent Stem Cells from Mouse Embryonic and Adult Fibroblast Cultures by Defined Factors. Cell 126, 663-676 (2006).

Soh, B.S. et al. CD166(pos) subpopulation from differentiated human ES and iPS cells support repair of acute lung injury. Mol. Ther. J. Am. Soc. Gene Ther. 20, 2335-2346 (2012).

Yang, K.-Y. et al. IV delivery of induced pluripotent stem cells attenuates endotoxin-induced acute lung injury in mice. Chest 140, 1243-1253 (2011).

Imaizumi, M. et al. Evaluation of the use of induced pluripotent stem cells (iPSCs) for the regeneration of tracheal cartilage. Cell Transplant. 22, 341-353 (2013).González F, Boué S, Izpisúa Belmonte JC. Methods for making induced pluripotent stem cells: reprogramming à la carte. Nat Rev Genet. Apr. 2011;12(4):231-42.

Onorati, M. et al. Neuropotent self-renewing neural stem (NS) cells derived from mouse induced pluripotent stem (iPS) cells. Mol. Cell. Neurosci. 43, 287-295 (2010).

Nagai, K. et al. Long-term culture following ES-like gene-induced reprogramming elicits an aggressive phenotype in mutated cholangiocellular carcinoma cells. Biochem. Biophys. Res. Commun. 395, 258-263 (2010).

Kim, K. et al. Epigenetic memory in induced pluripotent stem cells. Nature 467, 285-290 (2010).

Kunisato, A. et al. Generation of induced pluripotent stem cells by efficient reprogramming of adult bone marrow cells. Stem Cells Dev. 19, 229-238 (2010).

Guo, G. et al. Klf4 reverts developmentally programmed restriction of ground state pluripotency. Dev. Camb. Engl. 136, 1063-1069 (2009).

Prigione, A., Fauler, B., Lurz, R., Lehrach, H. & Adjaye, J. The senescence-related mitochondrial/oxidative stress pathway is repressed in human induced pluripotent stem cells. Stem Cells Dayt. Ohio 28, 721-733 (2010).

Wolfrum, K. et al. The Large principle of cellular reprogramming: lost, acquired and retained gene expression in foreskin and amniotic fluid-derived human iPS cells. Plos One 5, e13703 (2010).

Aasen, T. et al. Efficient and rapid generation of induced pluripotent stem cells from human keratinocytes. Nat. Biotechnol. 26, 1276-1284 (2008).

Seki, T. et al. Generation of induced pluripotent stem cells from human terminally differentiated circulating T cells. Cell Stem Cell 7, 11-14 (2010).

Lin, S.-L. et al. Mir-302 reprograms human skin cancer cells into a pluripotent ES-cell-like state. RNA 14, 2115-2124 (2008).

Lin, S.-L. et al. Regulation of somatic cell reprogramming through inducible mir-302 expression. Nucleic Acids Res. 39, 1054-1065 (2011).

\* cited by examiner d e f

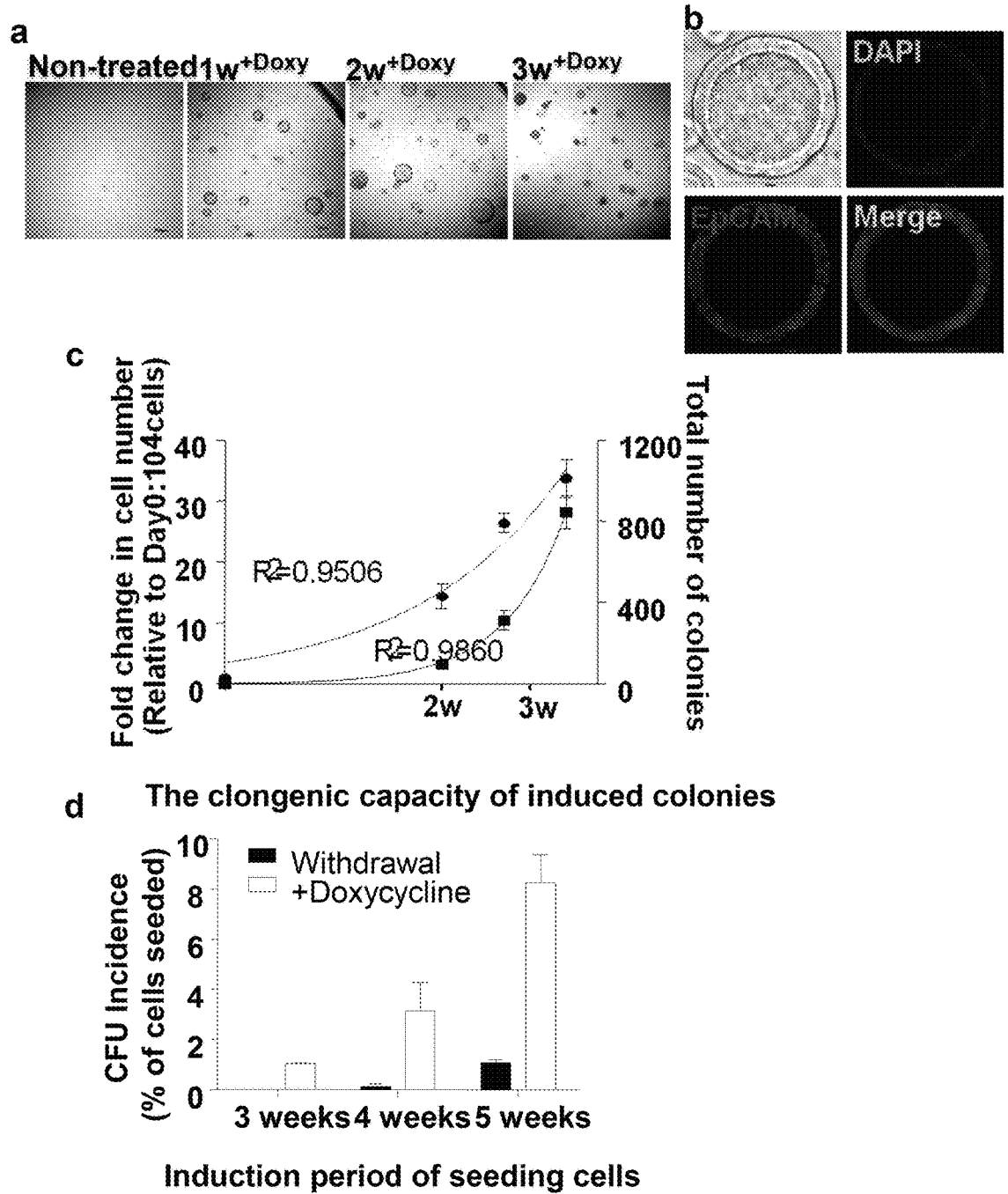

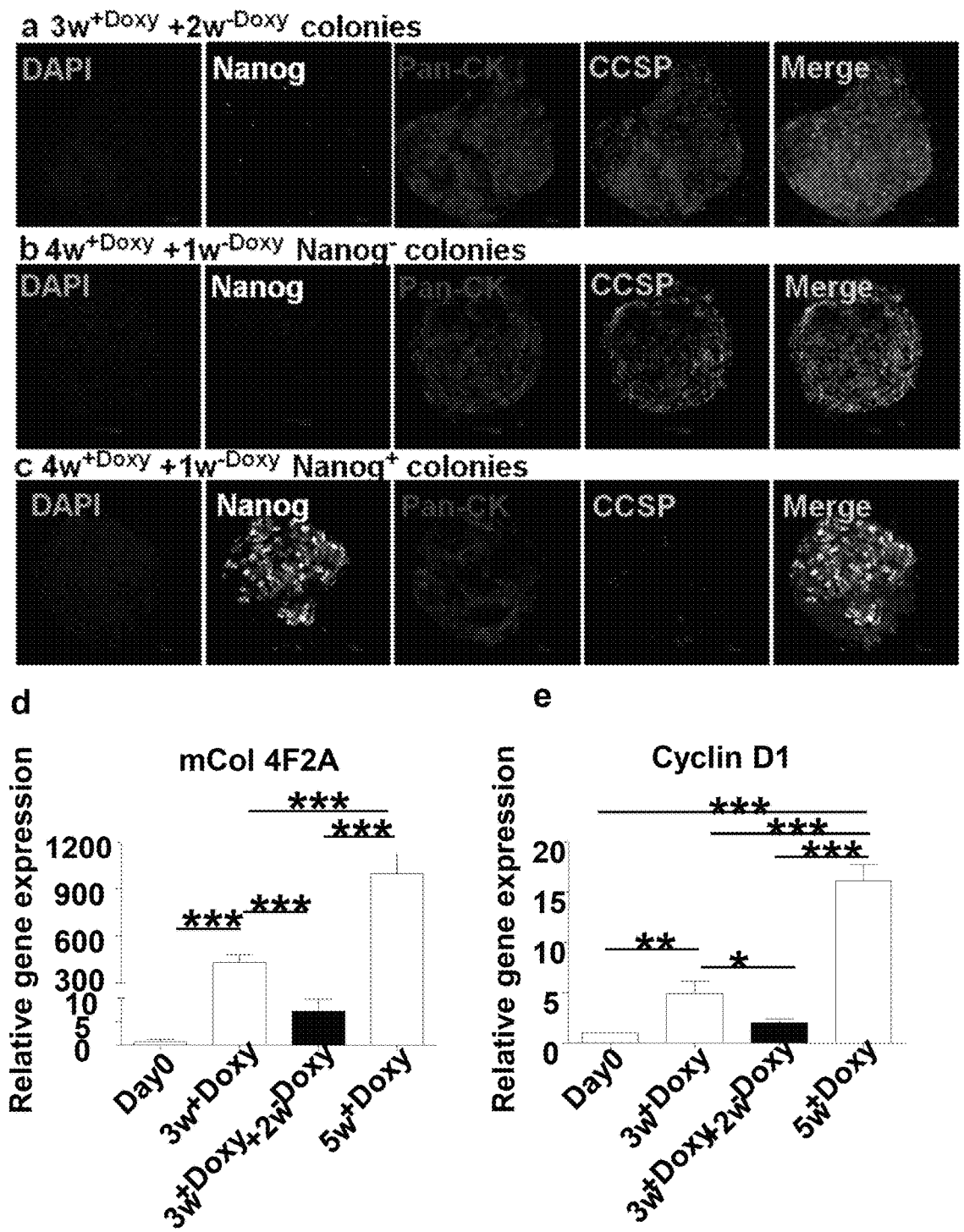

a b

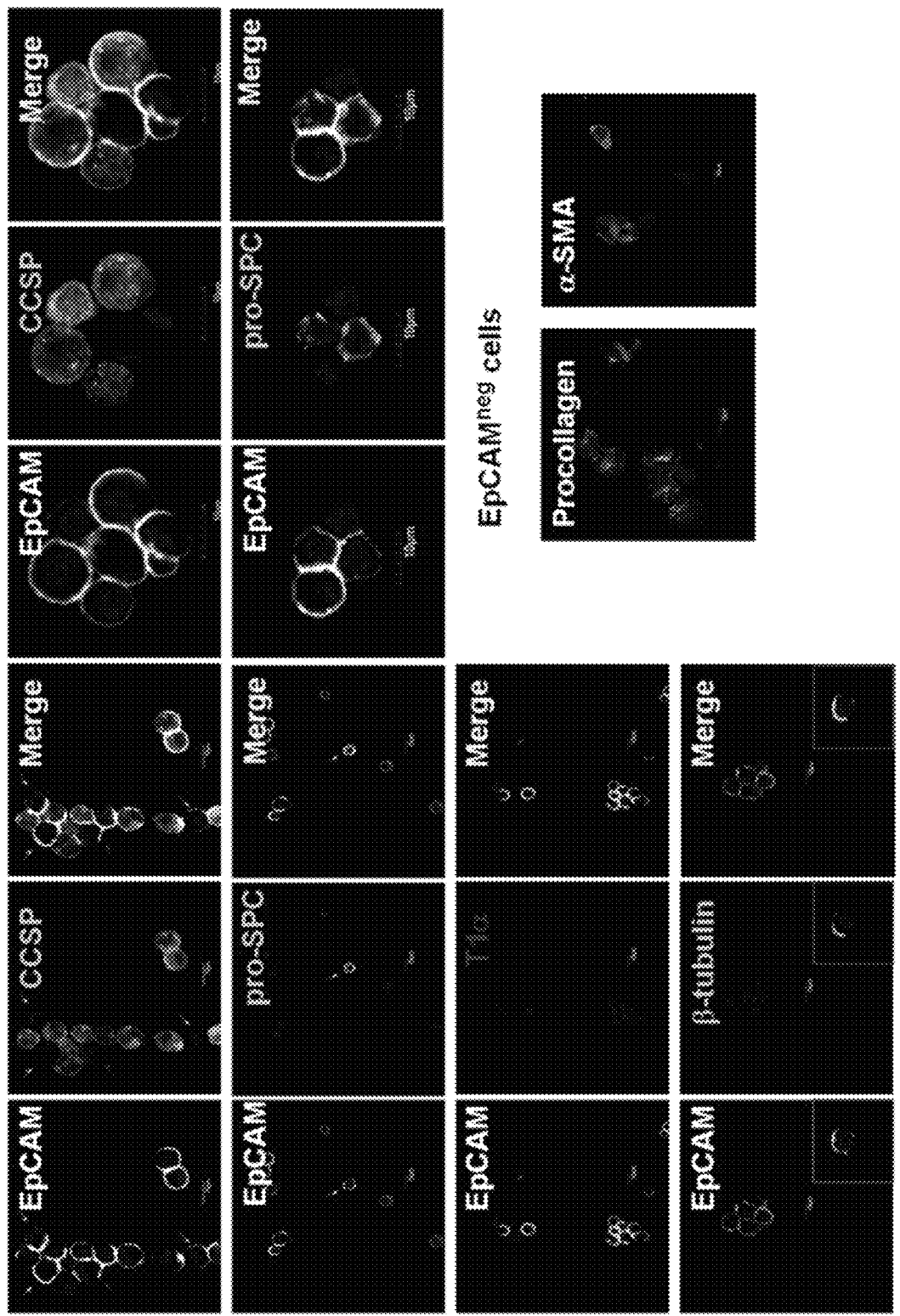
Figure 11. a b c a b

A

D

METHODS AND COMPOSITIONS FOR PRODUCING INDUCED AIRWAY TISSUE PROGENITOR CELLS

CROSS REFERENCE TO RELATED APPLICATIONS

This application claims the benefit of 35 USC 119 based on the priority of U.S. Provisional Application No. 61/830,483 filed Jun. 3, 2013, which is herein incorporated by reference in its entirety.

FIELD

The disclosure relates to methods for producing an induced progenitor population (iPP) of cells from somatic airway tissue cells, and particularly to methods of producing an expanded population of somatic airway tissue cells of a desired lineage using iPP, for use in cell replacement therapy, cell therapy, tissue engineering, disease modeling, and drug screening.

INTRODUCTION

Acute and chronic lung diseases remain major healthcare burdens, and are expected to increase with an aging population. Following acute lung injury, spirometry returns to normal but many patients still experience desaturation during exercise 12 months later [25]. Economic analyses indicate total direct costs of ~C$195,000 (2010 dollars) for the first hospitalization, with significant ongoing costs [26]. Chronic lung disease is even more costly; COPD alone was estimated to cost US$ 53.7B (2008 dollars) in direct medical costs in the USA (NIH-NHLBI, Disease statistics, 2011). Worldwide, it is a leading cause of death and disability [27]. For patients with end-stage lung disease, direct costs are high [28] and lung transplantation has become a cost-effective approach [29]. Lung transplantation remains limited by both a shortage of donors and a low utilization rate of donor lungs. Regeneration of healthy lung is an exciting long-term goal but successfully reproducing the complex architecture of the lung presents a formidable challenge.

The field of cell-based therapy in organ repair remains complex. Cell replacement therapy, for example, for cystic fibrosis, will likely require long-term engraftment and that the newly engrafted cells have a lifelong competitive repopulation advantage. Cell therapy, for instance, for acute lung injury, may be mediated by paracrine modulation of injury without any requirement of epithelial mimicry or long-term engraftment. Cell therapy per se may retain distinct advantages including the secretion of multiple synergistic factors. Organ regeneration, either on biohybrid devices with partially synthetic scaffolds or using decellularized scaffolds as substrates are also exciting possibilities. Biohybrid oxygenators are being developed and may have advantages for long-term usage in extracorporeal life support. Finally, drug screening and disease modeling applications are being developed that will allow characterization of individual patient pathophysiology and responses to therapy in specific cell types. Importantly, all of these applications require the ability to generate large numbers of cells of highly purified mature cell phenotypes.

Research groups all over the world have attempted different strategies to isolate and purify many types of stem cells, but the lack of specific markers for the prospective isolation and characterization of endogenous lung stem cell properties has compromised the ability to determine how to best harness their potential to attenuate disease or effect cure.

There has been significant effort put forth to generate lung epithelium using embryonic (ES) stem cells ([59], [58], [60], [65]). Recent progress in directed differentiation studies ([33], [62], [32]) have indicated their potential for use as a cell source for treatment of lung injury ([32], [33]) as well as in lung scaffolds ([66], [67], [68]). However the therapeutic use of these cells, is significantly limited by insufficient purity and low yields of mature cell types as well as safety issues resulting from potential teratoma formation in vivo ([32]). Two recent studies showed in vitro differentiation of iPS and ESCs to lung epithelium ([32], [33]), but were not able to generate large numbers of either Clara cells or ciliated cells. Neither group has evaluated the in vivo contribution of resultant cell types in a model of cell replacement therapy.

Induced pluripotent stem cells were initially generated via transfection of somatic cells with specific transcription factors to induce a pluripotent phenotype ([69]). Success in utilizing iPS cells as a source for lung regeneration both in cell-based applications ([70], [71]) as well as in scaffolds ([72]) has recently been presented. As with ES cells, however, therapeutic use of induced pluripotent stem cells remains significantly restricted in the production of sufficient numbers and desired phenotypes of 'end products'.

The generation of induced pluripotent stem cells is a multistep process comprised of initiation, maturation and stabilization phases. Events occurring in each of the phases of reprogramming mouse embryonic fibroblasts to induced pluripotent stem cells have been demonstrated [5]. One of the phenotypic changes in the initiation phase is rapid induction of proliferation with upregulation of proliferation genes such as Ccnd1, Ccnd2 and DNA replication genes. Moreover, successful reprogramming can be accomplished through the expression of the four inductive factors (c-Myc, Klf4, Oct4, and Sox2) until the induced pluripotent stem cell state is established [16].

Induced pluripotent stem cells can be derived from not only fibroblasts, but also other cell types, including blood, stomach and liver cells, keratinocytes, melanocytes, pancreatic B cells and neural progenitors [16]. All induced pluripotent stem cell lines express pluripotency genes and generate chimeric mice. Recent studies detected molecular and functional differences among induced pluripotent stem cells derived from different somatic cell types. Kim et al. (2010) and Polo et al. (2010) [23, 24] reported that the cell type of origin influences the transcriptional profile, the epigenetic state and differentiation potential of mouse induced pluripotent stem cells. A method of generating induced vascular progenitor cells from endothelial cells with the ability to differentiate into vascular smooth muscle cells or endothelial cells (EC) has been reported [22]. The reprogramming strategy used led to the production of induced pluripotent cells from mouse and rat fibroblasts but not rat EC. Numerous cell types can be converted to a pluripotency state with varying efficiencies and reprogramming is "context"-dependent with the cell type affecting the capability to become an iPSC. Also, reprogramming efficiency varies depending on the origin of cell type. Yin et al. (2011) indicate that using their reported reprogramming strategy, some cell types could be reprogrammed while others could not [22].

SUMMARY

Herein, cellular products via transient reprogramming are generated that can be used for various applications including therapeutic applications. A rapid induction of proliferation and identification of even more significant residual epigenetic "memory" in the early phase of the reprogramming process was exploited to generate lung precursor cells.

Using the herein presented strategy, large numbers of cells were generated from a purified lung epithelial population. Functionally these cells behave as "progenitors" in that they undergo controlled proliferation and differentiation into a limited range of progeny. Production of these progenitor cells was achieved by optimized, controllable, transient induction of exogenous reprogramming factors and by turning off expression of the reprogramming factors prior to the cells reaching pluripotency (FIG. 1). The term "induced Progenitor Population" (iPP) was coined to describe cells that proliferate upon expression of exogenous reprogramming factors, while retaining the ability to preferentially revert to the lineage of cell origin. These iPP cells differ from reprogrammed iPS cells in that proliferative capacity remains under the control of the exogenous inductive factors and the cells preferentially return to their original cell lineage upon cessation of expression of the exogenous reprogramming factors.

Isolation of very specific populations of adult cells is possible using advanced flow cytometric sorting and cell culture techniques. These populations, if bestowed with proliferative capacity and limited differentiation potential, could be used in a variety of regenerative medicine practices, including cell replacement therapy, biohybrid devices, as well as modelling studies and drug screening for human diseases.

An aspect of the disclosure provides a method of producing an induced progenitor population (iPP) or induced population of cells from airway tissue somatic cells, comprising the steps:
 a. obtaining a starting cell population of airway tissue somatic cells, the cells of the starting cell population comprising one or more exogenous reprogramming factors; and
 b. culturing the cell under conditions suitable for transient expression of the one or more reprogramming factors in the starting cell population for a period of time to obtain an iPP of cells,
 c. optionally isolating the iPP cells; and
 d. terminating the transient expression of the one or more reprogramming factors while the proliferative capacity of the iPP of cells remains under the control of the one or more reprogramming factors to produce an induced population of cells.

In an embodiment, obtaining the starting population comprises a step of isolating the starting cell population from an antecedent population of cells.

In another embodiment, obtaining the starting population comprises a step of harvesting cells from a subject, isolating a starting population and introducing into the starting population the one or more exogenous reprogramming factor protein(s) and/or as mRNA(s) encoding the one or more exogenous reprogramming factor(s) and/or nucleic acid molecule(s) encoding the one or more reprogramming factor(s) each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent.

In yet another embodiment, the subject is human. In yet another embodiment the subject is murine.

In an embodiment, introducing into the starting population the one or more exogenous reprogramming factor protein(s) comprises delivering the protein(s) by transduction, liposomes, membrane permeabilization, trypsinization, osmotic shock, microinjection, and/or electroporation.

In an embodiment, introducing into the starting population the mRNA(s) encoding the one or more exogenous reprogramming factor(s) comprises delivering the mRNA by transfection, calcium phosphate or calcium chloride co-precipitation, DEAE-dextran mediated transfection, lipofection, electroporation and/or microinjection.

In an embodiment, the one or more exogenous reprogramming factor protein(s) and/or mRNA(s) encoding the one or more exogenous reprogramming factor(s) are delivered into the cells during the culturing step at a frequency of at least once every 10 days, at least once every 7 days, at least once every 5 days, at least every 2 days, at least every day, or at least every 12 hours.

mRNA (or miRNA) can be introduced using a delivery system that comprises a single delivery for example wherein the mRNA (or miRNA) is under the control of an inducible element such as a drug controllable expression component, for example in a retroviral construct. For example an inducible Tet system such as pTet-On-tTS element can be used to deliver inducible expression (82, 83).

In an embodiment, the one or more exogenous reprogramming factor protein(s) and/or mRNA(s) encoding the one or more exogenous reprogramming factor(s) are delivered into the cells during the culturing step more than 2 times, more than 4 times, more than 5 times, more than 10 times, more than 20 times, or more than 40 times.

In an embodiment, the period of time for the culturing step is less than 6 weeks, less than 5 weeks, less than 4 weeks, less than 3 weeks, less than 2 weeks or less than 1 week.

In an embodiment, terminating the expression of the one or more exogenous reprogramming factors is achieved by ceasing delivery of the exogenous reprogramming factor protein(s) and/or mRNA(s) encoding the one or more exogenous reprogramming factor(s) into the cells, and culturing the cells for a sufficient time to reduce the expression of the one or more exogenous reprogramming factors to levels insufficient to cause proliferation of the cells, for example levels comparable to levels in the starting population (e.g. Day 0).

In an embodiment, terminating the expression of the one or more exogenous reprogramming factors is achieved by removing the culture medium and halting cell growth, for example by freezing the iPP population and/or lyophilizing the iPP population.

An aspect of the disclosure provides a method of producing an induced progenitor population (iPP) of cells from airway tissue somatic cells, comprising the steps:
 a. obtaining a starting cell population of airway tissue somatic cells, the cells of the starting cell population comprising one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent; and
 b. transiently inducing expression of the reprogramming factors in the starting cell population for a period of time to obtain an iPP population of cells,
 c. optionally isolating the iPP and d. terminating the transient induction while the proliferative capacity of the iPP population of cells remains under the control of the one or more exogenous reprogramming factors to produce an induced population of cells.

In an embodiment, obtaining the starting population comprises a step of isolating the starting cell population from an antecedent population of cells.

In another embodiment, obtaining the starting population comprises a step of harvesting cells from a subject, isolating a starting population and introducing into the starting population the one or more exogenous nucleic acid molecules encoding one or more reprogramming factors each operably linked to an inducible control element, the one or more reprogramming factors comprising Oct4, Klf4, Sox2 and/or c-Myc, and the inducible control element directing expression of the reprogramming factor(s) under its control in response to the presence or the absence of an inducing agent.

In yet another embodiment, the subject is human. In yet another embodiment the subject is murine.

In another embodiment, the starting population comprises lung cells or tracheal cells.

In yet another embodiment, the lung cells are epithelial lung cells, optionally comprising alveolar Type I cells (AT-I), alveolar Type II cells (AT-II), Clara cells, ciliated columnar cells, goblet cells, and or basal cells.

In another embodiment, the Clara cells include variant Clara cells. In an embodiment the tracheal cells are epithelial tracheal cells, optionally basal tracheal cells.

In yet another embodiment, the starting cell population is isolated from the antecedent cell population using flow cytometry, magnetic separation, affinity chromatography, and/or resistance to cytotoxic agent.

In one embodiment the flow cytometry is fluorescence-activated cell sorting (FACS). In another embodiment the magnetic separation comprises use of magnetic beads. In an embodiment the cytotoxic agent is naphthalene.

In another embodiment, isolating the starting cell population comprises isolating cells on the basis of cell surface marker expression profile. In an embodiment the cell surface markers are selected from NGFR, CD45, CD31, EpCAM, CD74, CCSP, Pan-CK and/or Cldn10 when the starting population to be isolated comprises epithelial cells;

In one embodiment the starting cell population isolated comprises $NGFR^{pos}$ cells isolated from tracheal cells, optionally the method of isolating $NGFRP^{pos}$ cells comprises using FACS.

In another embodiment the starting cell population isolated comprises $CD31^{neg}/CD45^{neg}/EpCAM^{pos}$ cells isolated from lung cells, optionally the method of isolating $CD31^{neg}/CD45^{neg}/EpCAM^{pos}$ cells comprises using FACS.

In one embodiment the starting cell population comprises $CD31^{neg}/CD45^{neg}/EpCAM^{pos}$ cells further separated according to EpCAM expression level into a higher EpCAM expressing subpopulation ($EpCAM^{high}$) and/or a lower EpCAM expressing subpopulation ($EpCAM^{low}$). In one embodiment, the method of further separation comprises using FACS.

In one embodiment, the starting cell population comprises an $EpCAM^{high}$-Clara cell population isolated on the basis of a surface marker expression profile, the expression profile comprising of $CD45^{neg}$, $CD31^{neg}$, and/or $EpCAM^{high}$ optionally the method of isolating $CD45^{neg}$, $CD31^{neg}$, and/or $EpCAM^{high}$ cells comprises using FACS.

In yet another embodiment, isolation of the starting population of cells on the basis of cell surface marker profile results in enrichment of the starting cell population such that at least 50%, at least 60%, at least 70%, at least 80%, at least 90%, at least 95%, or about 100% of the starting cell population comprises the selected cell surface marker profile.

In another embodiment, the transient induction is for a time period of less than 6 weeks, less than 5 weeks, less than 4 weeks, less than 3 weeks, less than 2 weeks or less than 1 week.

In another embodiment, the induced progenitor number of cells in the iPP of cells increases at least 5-fold, 10-fold, 20-fold, 30-fold, 50-fold, 100-fold or more during the period of transient induction In one embodiment, the transient induction is terminated prior to detectable expression of one or more of SSEA-3, SSEA-4, TRA-1-60, TRA-1-81, tissue non-specific alkaline phosphatase, and/or Nanog.

In another embodiment an iPP population of cells show decreased expression of one or more of CCSP and Pan-CK, when the iPP population of cells is derived from $EpCAM^{high}$-Clara cells.

In another embodiment the transient induction is terminated by optionally washing the iPP population of cells and/or culturing the iPP population of cells in a withdrawal culture medium.

In yet another embodiment, the iPP population of cells is cultured with a withdrawal culture medium until the expression level of the reprogramming factors is decreased by at least 4-fold, 6-fold, 10-fold or more to produce an expanded withdrawal cell population expressing one or more lineage markers of the starting cell population.

In another embodiment the withdrawal cell population is cultured with one or more differentiation factors and/or under conditions that promote differentiation.

Another aspect provides a method of generating an expanded population of differentiated cells, comprising:
  a. producing an induced progenitor population (iPP) of cells from a starting cell population as described herein;
  b. culturing the iPP cells with a withdrawal culture medium to generate a withdrawal cell population, the withdrawal culture medium lacking inducing agent; and optionally
  c. differentiating the withdrawal cell population by culturing the withdrawal cell population under conditions that promote differentiation to produce a differentiated population of cells.

In one embodiment conditions that promote differentiation comprise culturing the iPP cells after withdrawal of transient induction in an air-liquid interface (ALI) culture system.

In another embodiment the culture system comprises a 3D culture matrix. In yet another embodiment the 3D culture matrix is supported by feeder cells.

In an embodiment, the cells are cultured in withdrawal medium for less than 5 weeks, less than 4 weeks, less than 3 weeks, less than 2 weeks or less than 1 week.

In another embodiment, differentiating the withdrawal population step lasts for less than 5 weeks, less than 4 weeks, less than 3 weeks, less than 2 weeks or less than 1 week.

In one embodiment, the number of cells making up the withdrawal population of cells and/or the differentiated population of cells is at least 5-fold, 10-fold, 20-fold, 30-fold, 50-fold, 100-fold or more, greater than the number of cells making up the starting cell population.

In another embodiment, the starting population comprises an isolated population of Clara cells.

In another embodiment, isolation of the Clara cell population comprises sorting a population of $CD31^{neg}CD45^{neg}EpCAM^{pos}$ lung epithelial cells on the basis of EpCAM expression and isolating the $EpCAM^{high}$ cells, optionally using FACS.

An aspect provides a method of isolating a naphthalene sensitive Clara-enriched population from lung epithelial cells comprising sorting a population of $CD31^{neg}CD45^{neg}EpCAM^{pos}$ lung epithelial cells on the basis of EpCAM expression and isolating the $EpCAM^{high}$ cells, optionally using FACS.

Another aspect provides a method of producing an induced pluripotent stem (IPS) cell population from somatic cells, comprising the steps:
 a) isolating a starting cell population;
 b) introducing into the starting population one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent; and
 c) transiently inducing expression of the reprogramming factors in the starting cell population for a period of time to obtain an induced pluripotent stem cell population of cells, and
 d) terminating the transient induction at a point during the induction when the proliferative capacity of the induced pluripotent stem cell population is independent of the one or more exogenous reprogramming factors.

Yet another aspect provides a method of producing an expanded population of epithelial lineage cells, comprising the steps:
 a. obtaining a starting population of Clara cells;
 b. introducing into the starting population one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent;
 c. transiently inducing expression of the reprogramming factors in the starting cell population for a period of time to obtain an expanded population of cells;
 d. optionally isolating the expanded population of cells;
 e. terminating the transient induction by withdrawing the inducing agent before the expanded population of cells reaches a pluripotent state; and
 f. culturing the induced cell population after withdrawal of the inducing agent (e.g. the withdrawal population) in epithelial medium, to generate a withdrawal cell population comprising cells expressing one or more markers selected from Pan-CK, EpCAM, Claudin 10 and E-Cadherin.

In one embodiment, obtaining the starting population of Clara cells comprises a step of isolating the starting cell population from an antecedent population of cells. In another embodiment obtaining the starting population comprises steps of harvesting cells from a subject, isolating a starting population and introducing into the starting population the one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent.

In yet another embodiment, obtaining a starting population of Clara cells comprises isolating a population of cells enriched in $EpCAM^{high}$-Clara cells relative to the antecedent population of cells.

In another embodiment, isolation of the population of cells enriched in $EpCAM^{high}$-Clara cells from the antecedent population comprises using FACS to isolate cells on the basis of cell surface expression profile.

In another embodiment, the cell surface expression profile comprises $CD31^{neg}/CD45^{neg}/EpCAM^{high}$ cells.

In one embodiment, the starting population of Clara cells enriched in $EpCAM^{high}$-Clara cells comprises at least 80%, at least 90%, at least 95%, or about 100% of $EpCAM^{high}$ Clara cells.

In another embodiment, the transient induction lasts for a period of less than 5 weeks, less than 4 weeks, less than 3 weeks, less than 2 weeks or less than 1 week.

In yet another embodiment, the starting cell population is cultured in a 3D matrix culture during induction.

In another embodiment, the inducible control element comprises a tet-on or a tet-off promoter system.

In an embodiment, induction comprises adding or withdrawing an inducing agent, wherein the inducing agent is tetracycline or doxycycline.

In another embodiment, the withdrawal cell population comprises cells of Clara lineage, wherein the Clara lineage cells express the markers Pan-CK, EpCAM, E-Cadherin, Claudin10 and CCSP.

In yet another embodiment, culturing the induced cell population after withdrawal of the inducing agent comprises culturing in epithelial medium in a 3D matrix culture optionally with the support of feeder cells.

In another embodiment, culturing the induced cell population after withdrawal of the inducing agent lasts for a period of less than 5 weeks, less than 4 weeks, less than 3 weeks, less than 2 weeks or less than 1 week. In another embodiment, the method further comprises a step of culturing the induced cell population or withdrawal cell population under conditions that promote differentiation.

In an embodiment, the conditions that promote differentiation comprise an air-liquid interface (ALI) culture system. In another embodiment, the ALI culture system comprises a 3D culture matrix with support of feeder cells.

In yet another embodiment, the withdrawal population of cells and/or the differentiated population of cells is administered to a subject.

A further aspect provides an isolated cell or population of cells generated by the methods described herein, or a cell or cells derived and/or differentiated therefrom.

Another aspect provides a composition comprising an isolated population of cells generated by the methods described herein, or cells derived and/or differentiated therefrom, and a diluent.

Yet another aspect provides a method of engraftment or cell therapy comprising:
 a. producing an induced progenitor population of cells or cells derived and/or differentiated therefrom according to a method described herein, the starting population of cells being donor cells harvested from a donor; and
 b. administering the induced population of cells produced from the donor cells to a target tissue, scaffold, or subject.

Another aspect provides a use of an isolated population cells (e.g. iPPs or expanded epithelial population of cells)

generated by a method described herein, or cells derived and/or differentiated therefrom, for engraftment or cell therapy in a subject in need thereof. In one embodiment, the subject is human.

In another embodiment the cells are autologous or non-autologous.

In another embodiment the administering or engraftment occurs ex vivo or in vivo.

In yet another embodiment, the induced population of cells produced from the starting population of donor cells is tested for teratoma formation prior to administration.

Another aspect provides a method of drug screening comprising:
a. obtaining an induced cell population prepared according to any of the methods described herein;
b. contacting the induced cell population with a test compound; and
c. assessing the effect of the drug of interest on the cell population.

In one embodiment, the starting cell population is harvested from a human patient.

In one embodiment, the test compound is for the treatment of cystic fibrosis.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description

BRIEF DESCRIPTION OF THE DRAWINGS

An embodiment of the present disclosure will now be described in relation to the drawings in which.

DETAILED DESCRIPTION OF THE DISCLOSURE

I. Definitions

Figure 1:
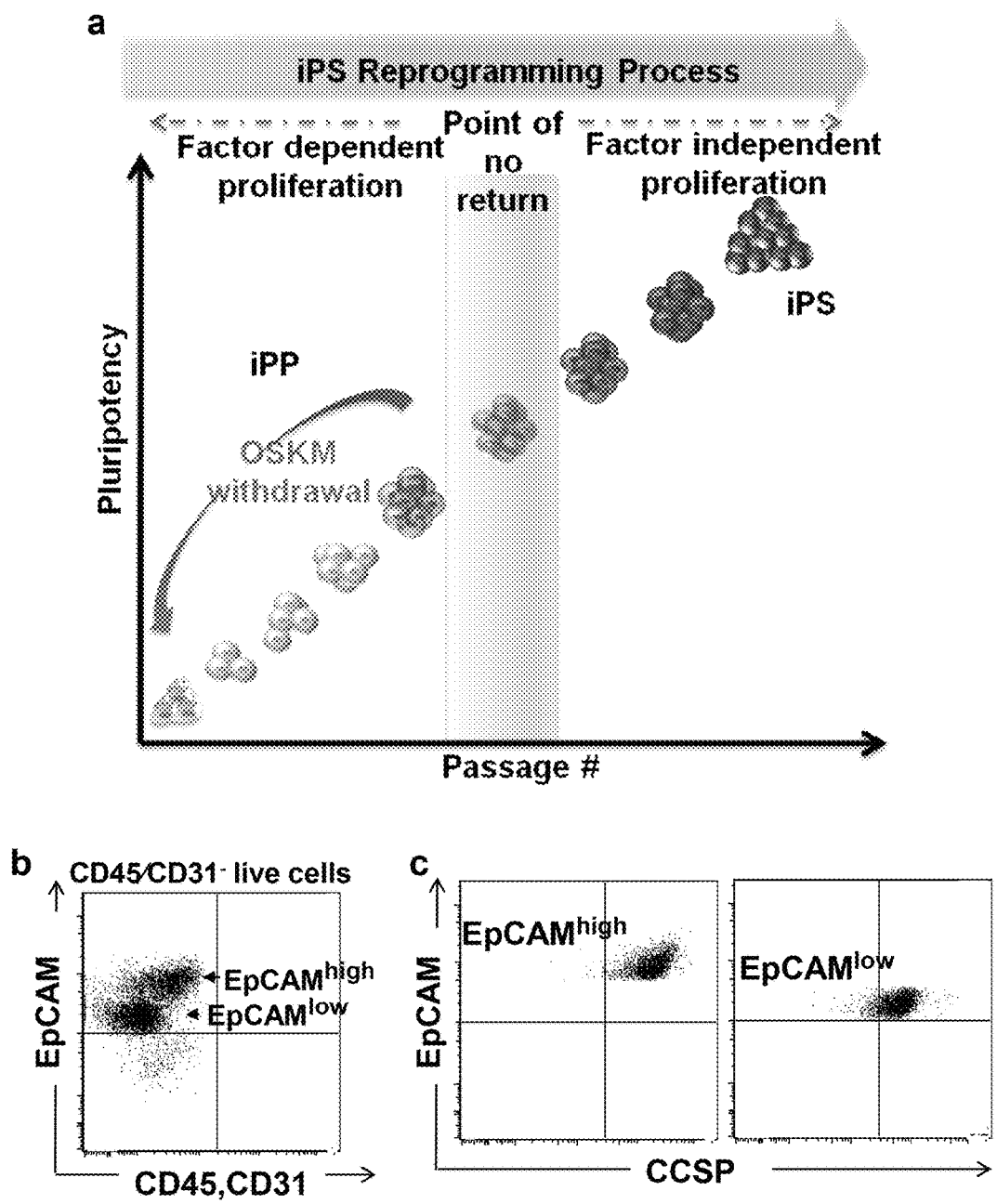
FIG. 1 $CD31^-CD45^-EpCAM^{high}$ epithelial cells are a highly purified naphthalene-sensitive Clara cell population in which regulation of inductive factors results in controlled proliferation. (a) Schematic graph depicting iPP generation. Representative flow cytometry dot-plots showing (b) $EpCAM^{high}$ and $EpCAM^{low}$ cells in a parental population of $CD31^-CD45^-$ fresh isolated lung tissue digested cells. (c) Dot plots showing $EpCAM^+CCSP^+$ lung epithelial cells. Expression of (d) Clara-cell and (e) epithelial lineage related genes, comparing fold-differences in gene expression in $EpCAM^{high}$ (solid black bars) and $EpCAM^{low}$ (open bars) cells. (f) Representative dot-plots comparing EpCAM expression in $CD45^-CD31^-$ freshly isolated lung cells from non-treated and naphthalene treated mice (n=3). (g) Dot-plots depicting CFSE labeled $EpCAM^{high}$ cells in the presence and absence of doxycycline in a feeder-separated semi-supportive culture system, at 5 days (top panel) and 7 days (bottom panel) post CFSE staining. (h) Dot plots showing CFSE-labelled Day 7 doxy-treated $EpCAM^{high}$ cells, maintained in culture for an additional 7 days with and without doxycycline treatment. Control untreated cells were cultured without Doxy for the entire 14 days. Expression of (i) mCol4F2A, (j) Cyclin D1, (k) EpCAM, and (l) CCSP, comparing fold-differences in gene expression in freshly isolated (Day 0), one-week doxy-treated (1 $w^{+Doxy}$), and induced cells cultured for an additional week in the presence (2 $w^{+Doxy}$) and absence (1 $w^{+Doxy}$+1 $w^{-Doxy}$) of doxycycline. In b, c, f and g data are representative of three biological replicates. For d, e, and i-l, values are mean±S.D. of triplicate samples. *, $p<0.05$; , $p<0.001$; *, $p<0.0001$.
Figure 1:
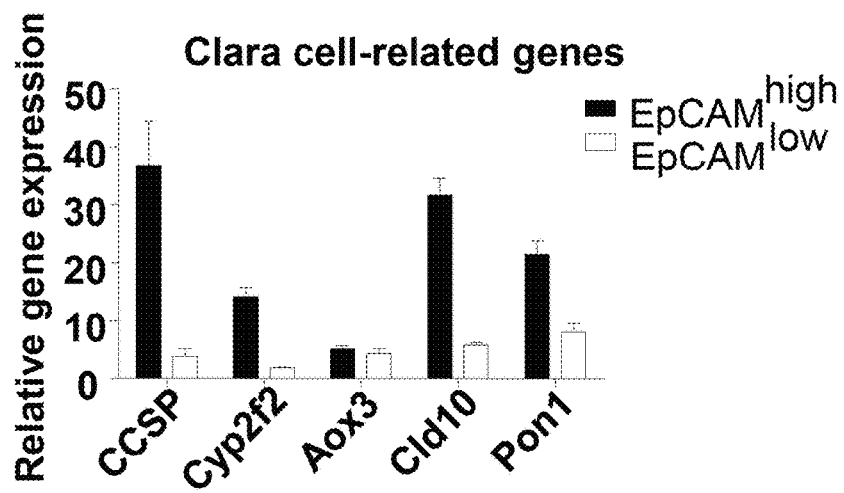
Figure 1:
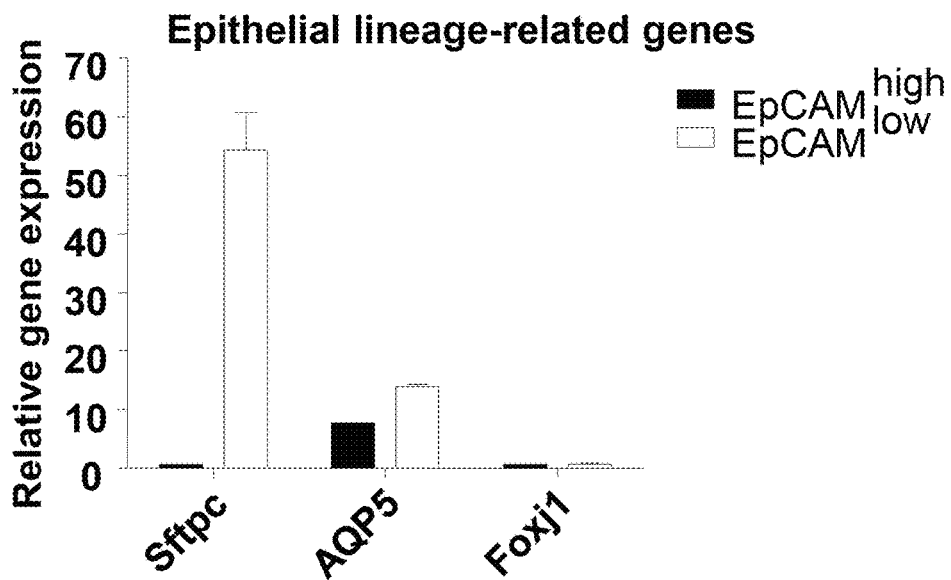
Figure 1:
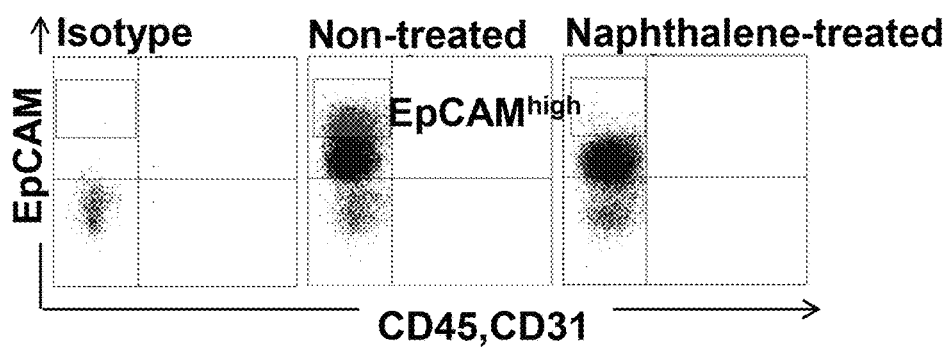
Figure 1:
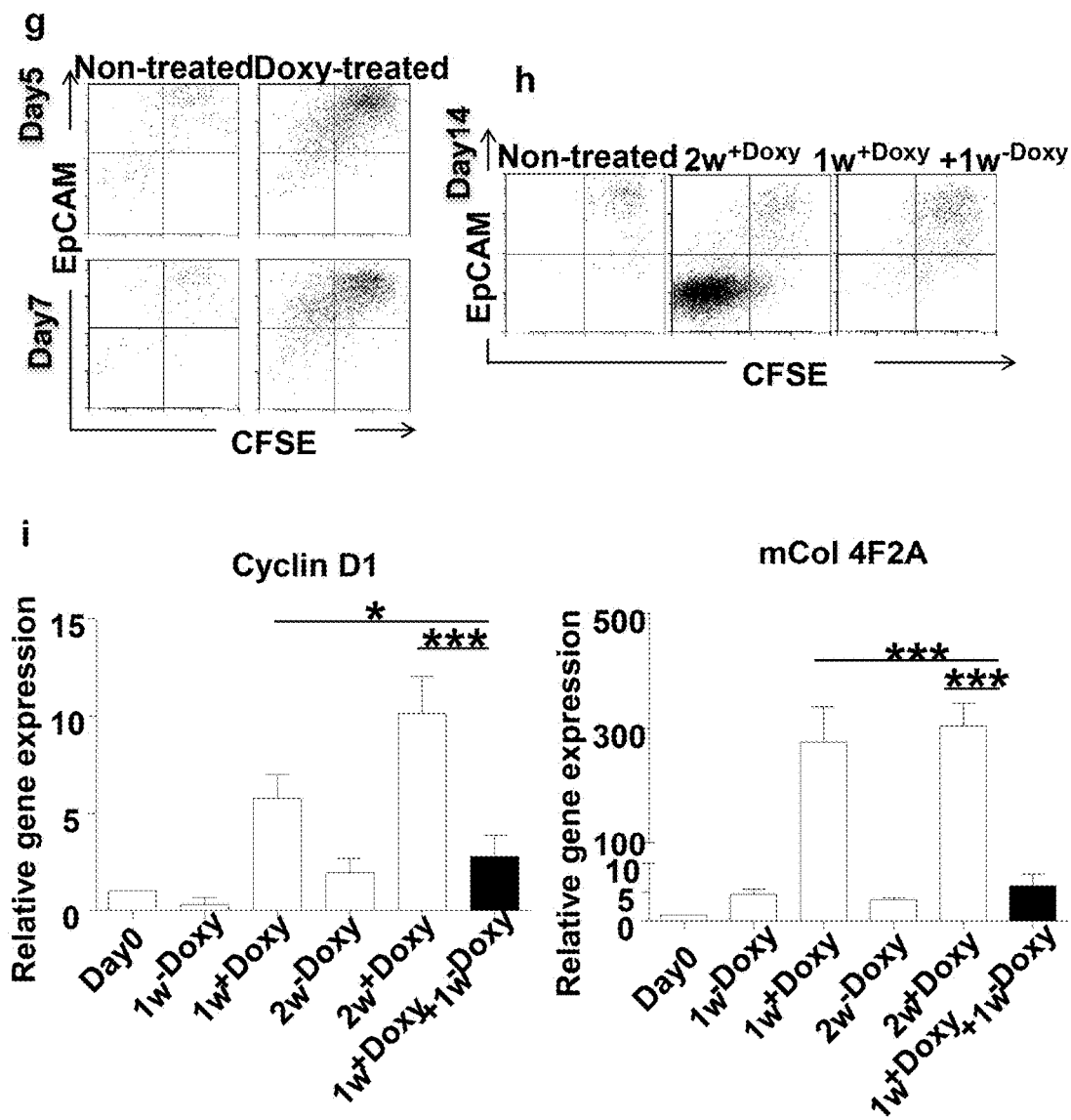
Figure 1:
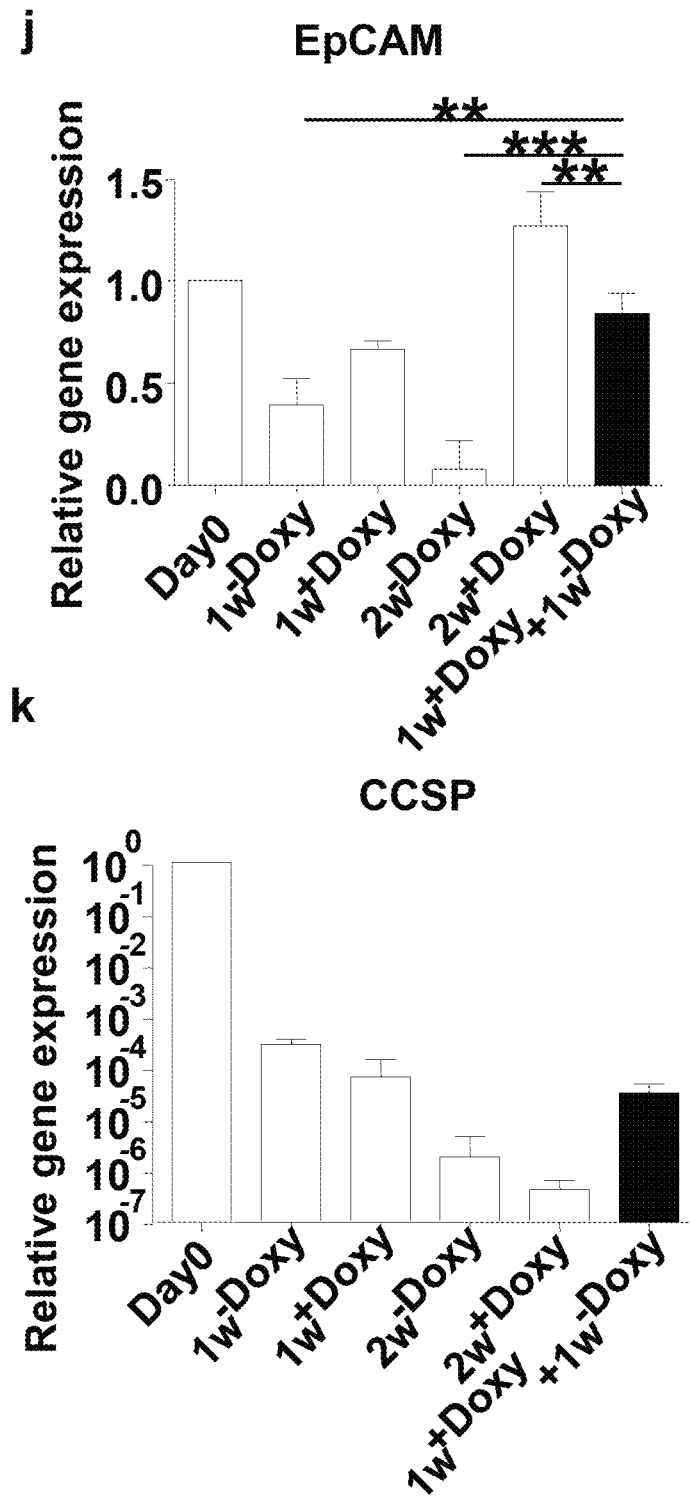

The term "reprogramming factors" as used herein refers to transcription factors, which have been shown, alone or in combination, to be sufficient to reprogram somatic cells into induced pluripotent stem cells. A number of reprogramming factors and conditions, which have been demonstrated to be sufficient to reprogram somatic cells into induced pluripotent stem cells and would be known to one skilled in the art, are reviewed in González et al., 2011. Reprogramming factors include, for example, Oct4, Klf4, Sox2, c-Myc, Nanog, and Lin28.

The term "somatic cell" as used herein includes both differentiated and undifferentiated somatic cells.

The term "induced progenitor population" (iPP) as used herein refers to a population of somatic cells that have increased proliferative capacity upon controlled expression of exogenous reprogramming factors, while retaining the ability to preferentially revert to the lineage of cell origin (e.g. a starting population cell type) upon cessation of the expression of exogenous reprogramming factors. The iPP of cells as used herein includes a population of cells undergoing transient expression of reprogramming factors according to a method described herein and also includes the "induced population of cells", produced when transient expression of exogenous reprogramming factors is terminated, and cells derived therefrom.

The term "induced population of cells" as used herein means a population of cells produced using a method described herein wherein the cells have expressed exogenous reprogramming factors, for example transiently, and expression of the exogenous reprogramming factors was terminated and the cells were optionally differentiated. The "induced population of cells" includes for example an induced progenitor population of cells wherein the induction is terminated by culturing in a withdrawal medium e.g. a withdrawal population, an expanded withdrawal population, an expanded population of differentiated cells, such as epithelial lineage cells, and an induced pluripotent stem cell population wherein the induction is terminated.

The term "withdrawal population of cells" refers to an "expanded population of cells" which has been or is being cultured under conditions which do not permit the cells to express the one or more exogenous reprogramming factors, for example, by culturing in withdrawal medium, wherein the cells have not acquired exogenous factor-independent proliferative capacity and/or pluripotency.

The term "withdrawal medium" as used herein refers to a cell culture medium that does not comprise an inducing agent.

The terms "pluripotency" and "pluripotent" as used herein refer to the ability of a cell to differentiate into a cell of all three germ layers. In particular, pluripotent cells are capable of differentiating into cells of the endoderm, mesoderm, or ectoderm.

The phrase "when the proliferative capacity of the cell population is independent of exogenous reprogramming factors" as used herein refers to the acquisition, by a cell or cell population, of the ability to proliferate in the absence of expression of the exogenous reprogramming factors. Cells that are no longer under the control of exogenous reprogramming factors may be partially reprogrammed iPS cells and/or acquire other stem cell-like properties and in particular pluripotency, which is the ability to differentiate into cells of all three germ layers. Whether cells have acquired the ability to proliferate independent of the exogenous reprogramming factors may be assayed, for example, by proliferation assays of the cells under conditions in which the exogenous reprogramming factors are not expressed. Whether cells have acquired pluripotency can be assessed for example in a teratoma assay and/or chimera generation. Indicators that an induced population of cells have, or will soon traverse to the pluripotent state and have acquired the ability to proliferate independent of exogenous reprogramming factors, include, for example, expression of pluripotent markers such as SSEA-1, endogenous Oct4, endogenous Sox2, SSEA-3, SSEA-4, TRA-1-60, TRA-1-81, tissue non-specific alkaline phosphatase, and/or Nanog. These markers are referred to as "indicators of pluripotency" herein.

The term "antecedent population" as used herein refers to a predecessor population of cells from which a sub-population of cells are derived, sorted, selected, separated, purified, or isolated.

The phrase "while the proliferative capacity of cells remains under the control of one or more exogenous reprogramming factors" as used herein means, for example, induced cells that remain under the proliferative control of the exogenous induction factors and do not express pluripotent markers such as SSEA-1, endogenous OCT4, endogenous SOX2, SSEA-3, SSEA-4, TRA-1-60, TRA-1-81, tissue non-specific alkaline phosphatase, and/or Nanog. These iPP cells for example can be Nanog$^{negative}$ and pan-CK/CCSP$^{low}$. For a given starting population the period of time a starting population can be induced without traversing to pluripotency can be determined by for example assessing for expression of pluripotency at different time points under specified conditions as described for example in Example 1. A suitable time point for example is one that permits for greatest expansion under the control of the exogenous induction genes, while maintaining restricted lineage differentiation and harbouring returning ability Conversely, in embodiments where induced stem cells are desired, "when the proliferative capacity of the cell population is independent of exogenous reprogramming factors" refers to cells who do express one or more pluripotent markers such as SSEA-3, SSEA-4, TRA-1-60, TRA-1-81, tissue non-specific alkaline phosphatase (detectable for example by TRA-2-49/6E), endogenous Oct4, endogenous Sox2 and/or Nanog. For example, human cells can express SSEA-3, SSEA-4, TRA-1-60, TRA-1-81, tissue non-specific alkaline phosphatase and/or Nanog, mouse cells can express Nanog.

The terms "expression" or "express" as used herein refers to the process resulting in production of an expression product which can be a nucleic acid, protein or peptide by a cell or cell population. The term "detectable expression" as used herein refers to a level of expression of an expression product which is detectable using methods that are known to the skilled person and include for example quantitative RT-Both mouse and human PCR and immunobased assays such as immunostaining or western blot, or fluorescence-activated cell sorting (FACS).

The term "Clara cells" refer to non-ciliated secretory epithelial cells found in the lungs and trachea. Clara cells express epithelial lineage markers such as Pan-CK, EpCAM, E-Cadherin, and Claudin 10, as well as Clara-related genes or gene products, including, for example, CCSP, Cyp2f2, Cldn10, Aox3, and Pon1.

The terms "EpCAM$^{high}$" and "EpCAM$^{low}$", as used herein, refer to isolated populations of CD45$^{neg}$/CD31$^{neg}$/EpCAM$^{pos}$ lung epithelial cells, which are characterized by level of EpCAM expression. For example, CD45$^{neg}$/CD31$^{neg}$/EpCAM$^{pos}$ lung epithelial cells may show two distinct populations of cells based on EpCAM expression by FACS analysis, wherein "EpCAM$^{high}$" cells are the "higher" EpCAM expressing population and "EpCAM$^{low}$" cells are the "lower" EpCAM expressing population. "EpCAM$^{high}$-Clara cells isolated from mouse lung cells can consist almost entirely, for example at least 90%, preferably at least 95%, more preferably at least 99%, even more preferably at least 99.99%, of naphthalene-sensitive Clara cells and are positive for Cldn10 and CCSP expression. The EpCAM$^{high}$-Clara cell population may be further distinguished by an increased CCSP expression (about 10-fold) and decreased sftpc expression (about 80-fold) relative to the EpCAM$^{low}$ population. As used herein, the terms "EpCAM$^{high}$ cells" and "EpCAM$^{high}$-Clara cells refer to an isolated population of cells having the characteristics described above, independent of the method used to isolate the population.

The term "variant Clara cells" refers to subset of Clara cells which are CCSP-expressing and resistant to cytochrome p450-bioactivated toxicant naphthalene.

The terms "patient" and "subject" which are used herein interchangeably refer to any member of the animal kingdom, preferably a human being including for example for embodiments involving administering a population of cells produced using a method described herein, a subject that has or is suspected of having a lung injury. The term "inducible control element" as used herein refers to a an element such as a DNA sequence which regulates transcription of an operably linked coding sequence in a particular cell or host organism in response to the presence or absence of an inducing agent. The induction can for example be reversible, for transcription is induced in the presence or absence of an inducer. The inducible control element may for example comprise one or more repeats of the Tet operator (tetO) sequence, for example Tet-off or Tet-on, which is responsive to tetracycline and/or its derivatives such as doxycycline. A control element may increase, decrease, start, stop or prevent transcription of an operably linked coding sequence in response to the presence or absence of an inducing agent. As used herein, the inducible control element will not activate or suppress expression of operably linked genes under its control in the absence or upon withdrawal of induction.

An "inducing agent" is a factor that may be administered, or may be withdrawn, in order to affect the inducible control element. An inducing agent may be, for example, tetracycline or a tetracycline derivative such as doxycycline. An example of an inducible control element is provided in Example 1, which describes an expression system wherein a Tet promoter drives expression of inducible polycistronic cassette (4F2A) encoding the reprogramming factors Oct4, Klf4, Sox2 and c-Myc. As demonstrated therein, the expression of the reprogramming factors is inducible by the inducing agent, doxycycline.

The term "induction" or "transient induction" as used herein refers to the process of driving expression of reprogramming genes under the control of an inducible control element for a limited period of time. Induction may be achieved, for example, through the administration of an inducing agent or through the withdrawal of a repressing agent.

The term "late induction" as used herein comprises a transient induction preceded by a period of differentiation, for example about or up to 1 week, about or up to 2 weeks, about or up to 3 weeks or about or up to 4 weeks or more according to the cell time. For example, as described herein a method for inducing AT-II cells comprises differentiation for 2 weeks prior to induction.

The term "expression" or "expressing" as used herein refers to the presence of a protein within a cell. Expression of a protein may result, for example, from synthesis of the protein within the cell or from introduction of the protein into the cell. Expressed proteins include, for example, secretary and surface proteins produced by the cell.

The phrases "introducing a protein into a cell" or "delivering a protein into a cell" refer to the introduction of a protein into a cell or cell population. Introduction of exogenous protein may be accomplished by a number of methods known in the art, including, for example, by trypsinization, osmotic shock, microinjection, electroporation, cell-penetrating peptide conjugates, transduction and/or permeabilization, for example, by Sendai virus.

The term "differentiation" or "differentiated" as used herein refers to the process by which a less specialized cell, such as a progenitor cell, becomes a more specialized cell type, such that it is committed to a specific lineage.

The term "culture medium" as used herein refers to a nutritive liquid or gel medium that contains nutrients and factors capable of supporting growth and/or maintenance of cells cultured therein. Persons skilled in the art will appreciate the appropriate culture medium will vary depending on the cell population being cultured. Culture medium suitable for epithelial cells includes for example, ES (embryonic stem cell) medium, epithelial-specific (EpiS) medium, and Air-liquid-interface specific (ALI-specific) medium as described, for example, in Example 1.

Specifically, the term "ES medium" as used herein refers to media capable of supporting growth and/or maintenance of embryonic stem cell. For example ES medium may comprise Dulbeccos' Modified Eagles Medium, high glucose, without Na-Pyruvate containing 15% (v/v) Fetal Calf Serum (FCS), 1 mM Na-Pyruvate, 2 mM Glutamine, 100 µM β-Mercaptoethanol, 1× nonessential Amino Acids and 1000 U/ml leukocyte inhibitory factor (LIF).

The term "epithelial specific medium" or "epithelial medium" as used herein refers to media capable of supporting growth and/or maintenance of epithelial cells. For example, Epithelial medium may comprise EGF, FGF-10, HGF. In an embodiment, the epithelial medium is the EpiS medium described in Example 1, comprising DMEM/F12 (Invitrogen™) supplemented with 10% FBS, penicillin/streptomycin, 10 mg/ml insulin, 5 mg/ml transferring-selenium (Sigma-Aldrich®), epidermal growth factor (EGF, 20 ng/mL; Sigma-Aldrich®), fibroblast growth factor-10 (FGF-10, 50 ng/mL; R&D Systems®) and hepatocyte growth factor (HGF, 30 ng/mL; R&D Systems®).

The term "ALI-specific medium" as used herein refers to media capable of supporting growth and/or maintenance of cells in an air-liquid interface culture. For example Ali-specific medium may be Clonetics™ S-ALI™ air-liquid interface medium (LONZA) comprising EGF, epinephrine, insulin, triiodothyronine, transferrin, GA-1000, BSA-FAF, inducer, and retinoic acid.

The term "withdrawal medium" as used herein refers to a cell culture medium that does not comprise an inducing agent. The term "withdrawal population" refers to an IPP population of cells that has been cultured in withdrawal medium after transient induction. The withdrawal medium or recovery medium may for example be ES medium.

A "3D matrix culture" as used herein refers to a culture in which cells are cultured on a 3-dimensional scaffold.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments for treating cancer. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the terms "administering," "introducing" and "transplanting" are used interchangeably in the context of delivering cells into a subject, by a method or route which results in at least partial localization of the introduced cells at a desired site. The cells can be implanted directly to a tissue such as the lung, or alternatively be administered by any appropriate route which results in delivery to a desired location in the subject where at least a portion of the implanted cells or components of the cells remain viable.

The phrase "introducing into the starting population one or more exogenous nucleic acid molecules" describes the introduction of one or more exogenous nucleic acid molecules into one or more cells. Exogenous nucleic acid molecules can be introduced by a number of techniques generally known in the art, including, for example, calcium phosphate transfection, DEAE-dextran transfection, infection, electroporation, lipofection, heat shock, magnetofection, nucleofection, integrating episome, use of a gene gun or microinjection. Introduction of nucleic acid molecules to a cell or cell population refers to both stable and transient uptake of the genetic material.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and the include plural referents unless the content clearly dictates otherwise.

A number of genes and gene products are described herein. Table 1 provides reference accession numbers for genes and gene products referred to, the sequences associated therewith are herein incorporated by reference.

TABLE I

| Gene/Gene-product | NCBI Gene ID | Genbank Accession |
|---|---|---|
| alpha-SMA | 59 (human), 11475 (mouse) | NM_007392 |
| Aox3 | 71724 (mouse) | NM_023617 |
| beta-catenin | 1499 (human), 12387 (mouse) | NM_001165902 |
| beta-tubulin III | 10381 (human), 22152 (mouse) | NM_023279 |
| beta-tubulin IV | 10382 (human), 22153 (mouse) | NM_146116 |

TABLE I-continued

| Gene/Gene-product | NCBI Gene ID | Genbank Accession |
|---|---|---|
| BMP4 | 652 (human), 12159 (mouse) | NM_007554 |
| Ccnd1 | 595 (human), 12443 (mouse) | NM_007631 |
| Ccnd2 | 894 (human), 12444 (mouse) | NM_009829 |
| CCSP | 7356 (human), 22287 (mouse) | NM_011681 |
| CD31 | 5175 (human), 18613 (mouse) | NM_001032378 |
| CD45 | 5788 (human), 19264 (mouse) | NM_001111316 |
| CD74 | 972 (human), 16149 (mouse) | NM_001042605 |
| CFTR | 1080 (human), 12638 (mouse) | NM_021050 XM_622568 |
| Cldn10 | 9071 (human), 58187 (mouse) | NM_001160097 |
| c-Myc | 4609 (human), 17869 (mouse) | NM_019660 |
| Col1a1 | 1277 (human), 12842 (mouse) | NM_007742 |
| Cyclin D1 | 595 (human), 12443 (mouse) | NM_007631 |
| Cyp2f2 | 13107 (mouse) | NM_007817 |
| E-Cadherin | 999 (human), 12550 (mouse) | NM_009864 |
| EpCAM | 4072 (human), 17075 (mouse) | NM_008532 |
| Foxa1 | 3169 (human), 15375 (mouse) | NM_008259 XM_915825 |
| Foxa2 | 3170 (human), 15376 (mouse) | NM_010446 |
| foxj1 | 2302 (human), 15223 (mouse) | NM_008240 |
| Foxp1 | 27086 (human), 108655 (mouse) | NM_053202 |
| Hes1 | 3280 (human), 15205 (mouse) | NM_001197321 |
| Klf4 | 9314 (human), 16600 (mouse) | NM_008235 XM_192801 |
| Lin28 | 79727 (human), 83557 (mouse) | NM_010637 |
| Nanog | 79923 (human), 71950 (mouse) | NM_028016 |
| NGFR | 4804 (human), 18053 (mouse) | NM_033217 |
| N-myc | 4613 (human), 18109 (mouse) | NM_008709 (MYCN) |
| Oct4 | 5460 (human), 18999 (mouse) | NM_013633 (Isoform1) NM_001252452 (Isoform2) |
| Pon1 | 5444 (human), 18979 (mouse) | NM_011134 |
| pro-collagen | 4318 (human), 17395 (mouse) | NM_013599 |
| pro-SPC | 6440 (human), 20389 (mouse) | NM_011359 |
| Sox2 | 6657 (human), 20674 (mouse) | NM_011443 XM_985079 |
| Sox9 | 6662 (human), 20682 (mouse) | NM_011448 |
| SSEA-1 | 2526 (human) | NM_002032 |
| SSEA-3 | 2526 (human) | NM_002033 |
| SSEA-4 | 2526 (human) | NM_002033 |
| Tra-1-60 | | NM_001018111, NM_005397 |
| Tra-1-80 | | NM_001018111, NM_005397 |

Further, the definitions and embodiments described in particular sections are intended to be applicable to other embodiments herein described for which they are suitable as would be understood by a person skilled in the art. For example, in the following passages, different aspects are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods and Compositions

The inventors have through transient expression of reprogramming factors developed methods for exploiting, the residual epigenetic "memory" of the cell of origin. For example, described herein are methods for generating large numbers of proliferating cells, which revert to differentiated cells upon withdrawal of the reprogramming factors. This pool of cells has been termed an "induced Progenitor Population (iPP)". The iPP cells described herein are for example obtained at an earlier phase of reprogramming process and are different from partially reprogrammed iPS cells in that expression of exogenous genes can be sufficiently silenced in iPP cells and their proliferative capacity remains under the control of the exogenous inductive factors. These iPP cells, which are not fully reprogrammed, may be less pluripotent than true induced pluripotent stem cells and likely not as tumorogenic.

The methods of generating iPP cells described herein, involve use of a characterized purified somatic cell population, specifically, in terms of the differentiation status of the cells. Differentiation status refers to the degree of lineage commitment of a cell or cell line. Terminally differentiated cell have the greatest lineage commitment, while embryonic stem cells have little or no lineage commitment. Lineage commitment of a cell or cell population is determined by epigenetic factors such as, for example, DNA methylation and histone modification, which regulate gene expression.

The methods of generating iPP cells described herein involve harnessing the residual epigenetic memory of a somatic cell during reprogramming. As diagrammed in FIG. 1a, during the early phases of the iPS reprogramming process, withdrawal of reprogramming factors can cause a cell or cell population to revert to the original lineage. The methods disclosed herein involve the use of controlled expression of exogenous reprogramming factors. Specifically, the methods involve controlled termination, or silencing, of the expression of the exogenous reprogramming factors, while the cells are still able to return to their original lineage, and before the cells acquire exogenous factor-independent proliferative capacity.

The successful reprogramming of a variety of cell types to iPS cells has been reported and methods of reprogramming cells are known in the art (see Gonzalez et al., 2011). For example, successful reprogramming has been reported for number of murine cells including fibroblasts (Onorati et al., 2010), gastrointestinal cancer cells (Nagai et al., 2010), B cells (Kim et al, 2010), hematopoietic cells (Kim et al, 2010), neural progenitor cells (Kim et al, 2010), lymphocytes (Kim et al, 2010), neural stem cell (Kim et al, 2010), and bone marrow mononuclear cells (Kunisato et al., 2010). Similarly, successful reprogramming to iPS cells has been reported for a number of human cells including fibroblasts (Prigione et al., 2010), amniotic fluid cells (Wolfrum et al., 2010), hepatocytes (Liu et al, 2010), keratinocytes (Aasen, 2008), and terminally differentiated circulating T cell (Seki et al, 2010). A variety of transcription factors have been used in various combinations to successfully reprogram somatic cells to iPS cells. Successful iPS reprogramming has been achieved through the expression of as few as one reprogramming factor (Guo et al., 2009).

The iPP cells described herein can be a source of cells in the clinical setting for cell therapy. For example, iPP cells derived from lung cells and/or differentiated cells derived therefrom, can be used for treating lung injury, since lung epithelial cells can be harvested from the patient, expanded, and differentiated into functional ciliated lung epithelial cells for autologous lung regenerative cell therapy.

The iPP cells described herein can also be a source of cells for further expansion and/or differentiation using the methods disclosed. For example, an induced progenitor population produced according to the methods disclosed may be subjected to further cycles (e.g. isolation, induction of induction factors to iPP, withdrawal of inducing factor can be a cycle or induction of induction factors to iPP and withdrawal of inducing factors can be a cycle) of transient induction. The number of cycles a cell or cell population is subject to can result in increased expansion, and maintenance of epithelial cell lineage commitment without traversing to pluripotency. For example, cells may be subjected to 1.5 cycles or more, 2 cycles or more, 2.5 cycles or more, 3 cycles or more, 4 cycles or more, 5 cycles or more, 10 cycles or more, 20 cycles or more, or 100 cycles or more.

For 1.5 cycles for example means a period of induction and withdrawal (e.g. one cycle) followed by a further period of induction (0.5 cycle) prior to use, for example prior to introduction into a subject or engraftment in a scaffold or use in a screening assay.

An aspect of the disclosure provides a method of producing an induced progenitor population (iPP) and/or induced population of cells from airway tissue somatic cells, comprising the steps:
 a. obtaining a starting cell population, the cells of the starting cell population comprising one or more exogenous reprogramming factors; and
 b. culturing the cell under conditions suitable to allow transient expression of the reprogramming factors in the starting cell population for a period of time to obtain an iPP of cells, and
 c. optionally isolating the iPP and
 d. terminating the transient expression of the one or more reprogramming factors while the proliferative capacity of the iPP of cells remains under the control of the one or more exogenous reprogramming factors to produce an induced population of cells.

Expression of exogenous proteins within a cell or cell population may be achieved by a variety of methods known in the art. For example, cells may be transfected with nucleic acid molecules, including mRNA and DNA, encoding the exogenous protein. Expression of exogenous proteins may also be achieved, for example, by direct introduction of the exogenous protein into the cell or cell population. Where proteins and/or mRNA are directly introduced into a cell, the short intracellular half-life of the introduced molecules may require that the molecules be periodically reintroduced to maintain expression levels during the step of culturing the cell under conditions which allow expression of the reprogramming factors.

The methods described herein involve controlled expression of exogenous reprogramming factors, which allows expression of the factors to be terminated. Where the expression is achieved through transfection of the cells with nucleic acids encoding the exogenous factors, termination of the expression may be achieved by methods known in the art. For example, gene expression may be terminated by the expression of a repressor acting on the gene, by excision of the gene, through the use of siRNA, or by ceasing induction if an inducible expression system is used. If the expression is achieved through direct introduction of protein and/or mRNA into the cell, expression may be terminated, for example, by ceasing to introduce new protein and/or mRNA into the cell.

In an embodiment, obtaining the starting population comprises a step of isolating the starting cell population from an antecedent population of cells.

In another embodiment, obtaining the starting population comprises a step of harvesting cells from a subject, isolating a starting population and introducing into the starting population the one or more exogenous reprogramming factor protein(s) and/or mRNA(s) encoding the one or more exogenous reprogramming factor(s) and/or nucleic acid molecule(s) encoding the one or more reprogramming factor(s) each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent. In yet another embodiment, the subject is human. In yet another embodiment the subject is murine.

In an embodiment, introducing into the starting population the one or more exogenous reprogramming factor protein(s) comprises delivering the protein(s) by transduction, liposomes, membrane permeabilization, trypsinization, osmotic shock, microinjection, and/or electroporation.

In an embodiment, introducing into the starting population the mRNA(s) encoding the one or more exogenous reprogramming factor(s) comprises delivering the mRNA by transfection, calcium phosphate or calcium chloride co-precipitation, DEAE-dextran mediated transfection, lipofection, electroporation and/or microinjection.

In an embodiment, the one or more exogenous reprogramming factor protein(s) and/or mRNA(s) encoding the one or more exogenous reprogramming factor(s) are delivered into the cells during the culturing step at a frequency of at least once every 10 days, at least once every 7 days, at least once every 5 days, at least every 2 days, at least every day, or at least every 12 hours.

In an embodiment, the one or more exogenous reprogramming factor protein(s) and/or mRNA(s) encoding the one or more exogenous reprogramming factor(s) are delivered into the cells during the culturing step more than 2 times, more than 4 times, more than 5 times, more than 10 times, more than 20 times, or more than 40 times.

In an embodiment, the period of time for the culturing step is less than 6 weeks, less than 5 weeks, less than 4 weeks, less than 3 weeks, less than 2 weeks or less than 1 week.

In an embodiment, terminating the expression of the one or more exogenous reprogramming factors is achieved by ceasing delivery of the exogenous reprogramming factor protein(s) and/or mRNA(s) encoding the one or more exogenous reprogramming factor(s) into the cells, and culturing the cells for a sufficient time to reduce the expression of the one or more exogenous reprogramming factors to levels insufficient to cause proliferation of the cells.

An aspect of the disclosure provides a method of producing an induced progenitor population (iPP) of cells from a starting population of somatic cells, comprising the following steps obtaining a starting cell population, the cells of the starting cell population comprising one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent; and
 a) transiently inducing expression of the reprogramming factors in the starting cell population for a period of time to obtain an iPP population of cells, and
 b) optionally isolating the iPP and
 c) terminating the transient induction while the proliferative capacity of the iPP remains under the control of the one or more exogenous reprogramming factors to produce an induced population of cells.

In an embodiment, obtaining the starting population comprises a step of isolating the starting cell population from an antecedent population of cells. For example, lung epithelium cells can be separated into different cell populations according to for example cell marker expression. In another embodiment, obtaining the starting population comprises a step of harvesting cells from a subject. In yet another embodiment, the subject is human.

In certain embodiments, the nucleic acid molecules encoding one or more reprogramming factors are introduced into a starting cell population.

In another embodiment, obtaining the starting population comprises introducing into the starting population one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent; prior to transiently inducing expression.

In another embodiment, the obtaining step comprises isolating a starting population from an antecedent population, optionally harvested from a subject; and introducing into the starting population the one or more exogenous nucleic acid molecules encoding the reprogramming factors.

Another aspect provides a method of producing an induced progenitor population (iPP) of cells from somatic cells, comprising the steps:
 a) isolating a starting cell population from an antecedent cell population;
 b) introducing into the starting population one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent; and
 c) transiently inducing expression of the reprogramming factors in the starting cell population for a period of time to obtain an iPP population of cells, and terminating the transient induction while the induced cell population remains under the control of the one or more exogenous reprogramming factors to produce an induced population of cells.

A skilled person would appreciate that there are numerous methods of introducing one or more exogenous nucleic acid molecules to a cell or cell population, including, for example, calcium phosphate transfection, DEAE-dextran transfection, infection, electroporation, lipofection, heat shock, magnetofection, nucleofection, integrating episome, use of a gene gun or microinjection. Introduction of nucleic acid molecules to a cell or cell population refers to both stable and transient uptake of the genetic material. Stable uptake may be preferred when the cell population produced by the iPP method is self-renewing. Stably integrated reprogramming factors in a self-renewing population of cells would allow the cell population, for example, to be subsequently re-induced and expanded by the iPP methods taught herein. Transient uptake may be preferred, for example, when the cell population produced by the iPP method is terminally differentiated.

In situations where genomic integration of the exogenous nucleic acid molecules is not desired, excisable integration systems may be used. Examples of excisable integration systems include the Cre-Lox system and the PiggyBac transposon system. A Cre-Lox system may be employed, for example, by introducing an expression cassette comprising nucleic acid molecules encoding the one or more transcription factors to a target nucleic acid comprising a target site within the cell. The cassette may subsequently be removed by expressing Cre recombinase within the cell to excise regions of DNA flanked by the loxP target sites. A PiggyBac transposon system may be employed, for example, by introducing an expression cassette comprising nucleic acid molecules encoding the one or more transcription factors flanked by transposon-specific inverted terminal repeat sequences (ITRs) to a target nucleic acid comprising a TTAA target site within the cell. The cassette may subsequently be removed by expressing PiggyBac (PB) transposase within the cell to excise regions of DNA flanked by the ITRs.

In an embodiment, cells comprising the exogenous reprogramming factors are purified prior to induction.

The reprogramming factors comprising Oct4, Klf4, Sox2, c-Myc, Nanog, and/or Lin28 may be under the control of a single inducible control element, or multiple inducible control elements. Moreover, each inducible control element may control expression of one or more reprogramming factors. Inducible expression systems are well known in the art, and include, for example, the "tet-on" and "tet-off" promoter system.

As described, iPP are not stem cells and the methods result in a population of cells that retain epigenetic cell lineage memory. Suitable somatic cells for producing an iPP according to the methods disclosed herein include differentiated and/or undifferentiated somatic cells.

Induced pluripotent stem cells from somatic cells by forcing expression of reprogramming factors, comprising Oct4, Klf4, Sox2, c-Myc, Nanog, and/or Lin28 have been demonstrated in different cell types including cells derived from fibroblasts, blood cells, stomach and liver cells, keratinocytes, melanocytes, pancreatic B cells and neural progenitors [16].

In an embodiment, the starting cell population comprises airway epithelial cells. Epithelial cells can be found in lung and trachea. Airway epithelial cells include basal cells, AT-I, AT-II, Clara cells, Ciliated cells, and NE cells.

In an embodiment, the starting population comprises lung cells and/or tracheal cells.

Yin et al. 2011 describes partially reprogrammed rat aortic endothelial cells that failed to complete a typical iPS reprogramming process. The partially reprogrammed iPS cells expressed the exogenous factors and exhibited an uncontrollable proliferation similar to iPS cells. Withdrawal of induction in Yin et al was performed according to colony morphology changes.

In another embodiment the starting cell population is isolated or purified for example from an antecedent cell population or after introduction of the exogenous reprogramming factors, using flow cytometry, magnetic separation, affinity chromatography, and/or resistance to cytotoxic agent.

In one embodiment the flow cytometry is fluorescence-activated cell sorting (FACS). In another embodiment the magnetic separation comprises use of magnetic beads. In an embodiment the cytotoxic agent is naphthalene.

In another embodiment, isolating the starting cell population comprises isolating cells on the basis of cell surface marker expression profile. In an embodiment the cell surface markers are selected from NGFR, CD45, CD31, EpCAM, CD74, CCSP, Pan-CK and/or Cldn10 when the starting population to be isolated comprises epithelial cells; In another embodiment,
 i) the cell surface markers are selected from CD45, CD31, EpCAM, and CD74 when the starting population is AT-II;
 ii) the cell surface markers are selected from CD45, CD31, NGFR and EpCAM when the starting population is trachea basal cells; or iii) the cell surface markers are selected from CCSP, Pan-CK and/or Cldn10 when the starting population is lung Clara cells;

In one embodiment, the starting population comprises tracheal cells. In one embodiment the starting cell population isolated comprises NGFR$^{pos}$ and/or EpCAM$^{high}$ cells isolated from tracheal cells (e.g. tracheal basal cells). Basal-progenitor cells in the mouse trachea are enriched in NGFR and EpCAM expression. It has been shown that a population of cells enriched in basal-progenitor cells can be isolated from mouse trachea by FACs sorting on the basis of NGFR expression.

In an embodiment, the starting population of cells comprises epithelial cells. Differentiation markers indicative of an epithelial phenotype include pan-CK.

In another embodiment, the starting cell population comprises lung cells. In an embodiment, the starting population isolated comprises CD31$^{neg}$/CD45$^{neg}$/EpCAM$^{pos}$ cells isolated from lung cells. CD31 is a cellular marker for endothelial cells. CD45 is a marker for hematopoietic cells. EpCAM is a marker for epithelial cells. As demonstrated in example 1, FACS sorting on the basis of CD31$^{neg}$/CD45$^{neg}$/EpCAM$^{pos}$ can be used to prepare a population of cells enriched in lung epithelial cells. Other markers that can be used for epithelial cells for example include NGFR, CD45, CD31, EpCAM, CD74, CCSP, Pan-CK and/or Cldn10.

In one embodiment the starting cell population comprises CD31$^{neg}$/CD45$^{neg}$/EpCAMP$^{pos}$ cells further separated according to EpCAM expression level into a higher EpCAM expressing subpopulation (EpCAM$^{high}$) and/or a lower EpCAM expressing subpopulation (EpCAM$^{low}$). In one embodiment this separation is accomplished using FACS.

In a further embodiment, the epithelial cell is a lung epithelial cell such as a Clara cell. In one embodiment, the starting cell population comprises an EpCAM$^{high}$-Clara cell population isolated on the basis of a surface marker expression profile of CD45$^{neg}$, CD31$^{neg}$, and EpCAM$^{high}$.

In yet another embodiment, isolation or purification of for example the starting population of cells on the basis of cell surface marker profile results in enrichment such that at least 50%, at least 60%, at least 70%, at least 80%, at least 90%, at least 95%, or about 100% of the isolated/purified population comprises the selected cell surface marker profile. Isolation or purification, can also be on the basis of expression, such that the isolated or purified population results in enrichment such that at least 50%, at least 60%, at least 70%, at least 80%, at least 90%, at least 95%, or about 100% of the isolated/purified population comprises the desired expression profile (e.g. reprogramming factors).

Enrichment of a cell population is measured relative to the antecedent population. Methods of detecting the presence of a selected expression or cell surface profile are generally known and include for example, drug selection, immunostaining methods and/or FACS.

An EpCAM$^{high}$-Clara cell population was isolated from mouse lung cells by FACS on the basis of a surface marker expression profile of CD45$^{neg}$, CD31$^{neg}$, and EpCAM$^{high}$. The isolated EpCAM$^{high}$-Clara population was enriched in Clara cells such that about 100% of the population comprised Clara cells, as determined by expression of Clara cell marker Cldn10 and measured by FACS, as described in Example 1. Differentiation markers indicative of a Clara cell phenotype also include for example CCSP and Cld10.

In another embodiment, the transient induction lasts for a period of less than 6 weeks, less than 5 weeks, less than 4 weeks, less than 3 weeks, less than 2 weeks or less than 1 week. The transient induction will vary for example on the cell type and the culture conditions.

Figure 3:
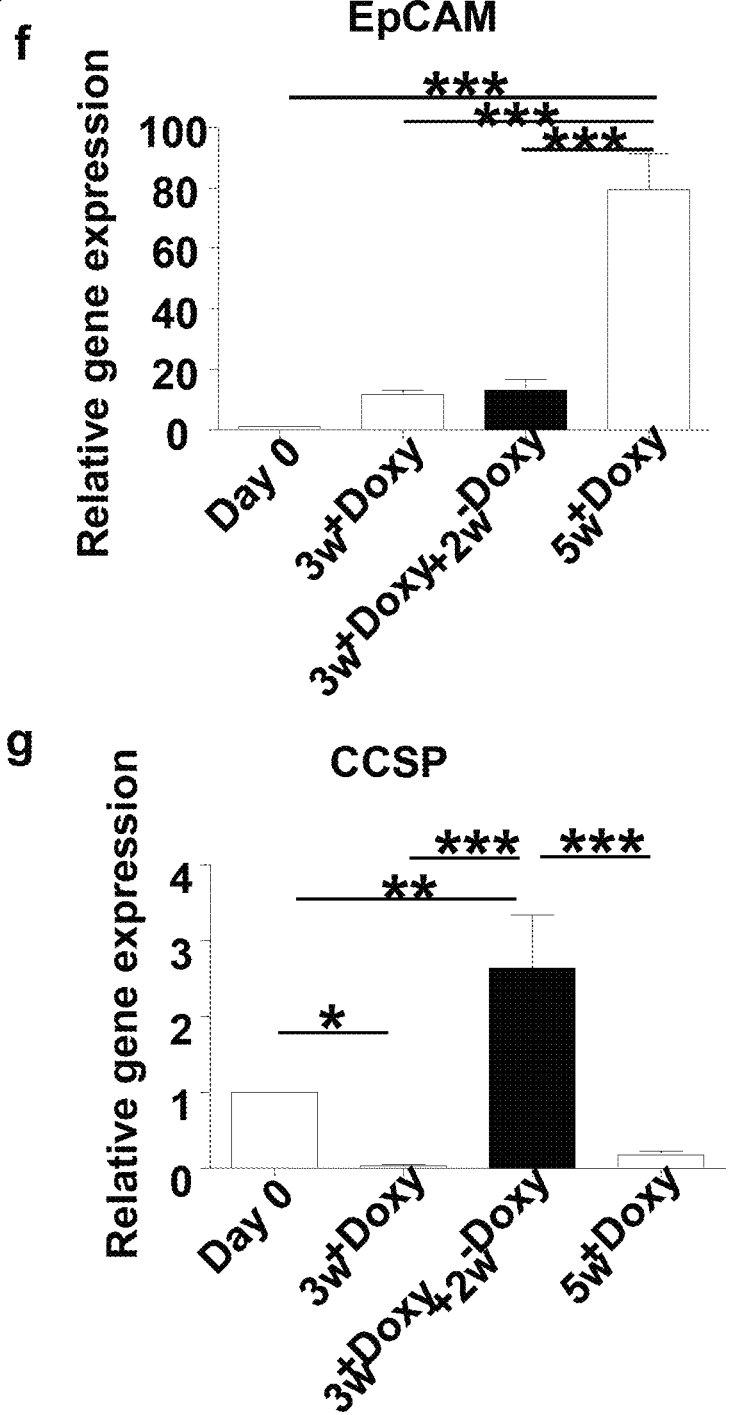
FIG. 3 Transient induction for 3 weeks under 3D Matrigel™-based conditions allows $EpCAM^{high}$-derived colonies to return to their original Clara cell phenotype upon withdrawal of inductive factors. Confocal microscopy images of (a) 3-week induced colonies maintained in culture for 2 weeks in the absence of doxycycline (3 $W^{+Doxy}$+2 $w^{-Doxy}$), (b) Nanog-negative 4-week induced colonies maintained in culture for 1 week in the absence of doxycycline (4 $W^{+Doxy}$+1 $W^{-Doxy}$), and (c) nanog-positive 4-week induced colonies maintained in culture for 1 week (4 $W^{+Doxy}$+1 $W^{-Doxy}$) without doxycycline showing cells stained with nuclear stain DAPI, Nanog, Pan-CK and CCSP (from the right panel to the left panel). Expression of (d) the transgene construct mCol4F2A (e) Cyclin D1, (f) Nanog, (g) EpCAM and (h) CCSP, as measured by qRT-PCR comparing fold-differences in gene expression in freshly isolated cells (Day 0), 3-week induced cells (3 $W^{+Doxy}$), 3-week induced cells with subsequent 2-week culture in doxycycline-free media (3 $W^{+Doxy}$+2 $w^{-Doxy}$), and 5-week induced cells (5 $W^{+Doxy}$). For d-g, values are mean±S.D. of triplicate samples. *, $p<0.05$; , $p<0.001$; *, $p<0.0001$. Scale bar, 10 µm (a-c).

As described herein, the period of transient induction to produce an iPP can be determined by monitoring induced cells for expression of indicators of pluripotency, including the marker Nanog, at various times during induction. A preferred period of induction is a period that is long enough to allow the induced cells to express the reprogramming factors and to proliferate, without expressing an indicator of pluripotency. For example, the isolated EpCAM$^{high}$-Clara cell population is negative for Nanog after 3 weeks of induction, however 20-30% of the 5 week induction population colonies express Nanog, indicating a preferred induction window of between 3-5 weeks under the conditions tested, as shown in FIG. 3d.

In yet another embodiment, the starting cell population is cultured in a 3D matrix culture during induction.

Figure 4:
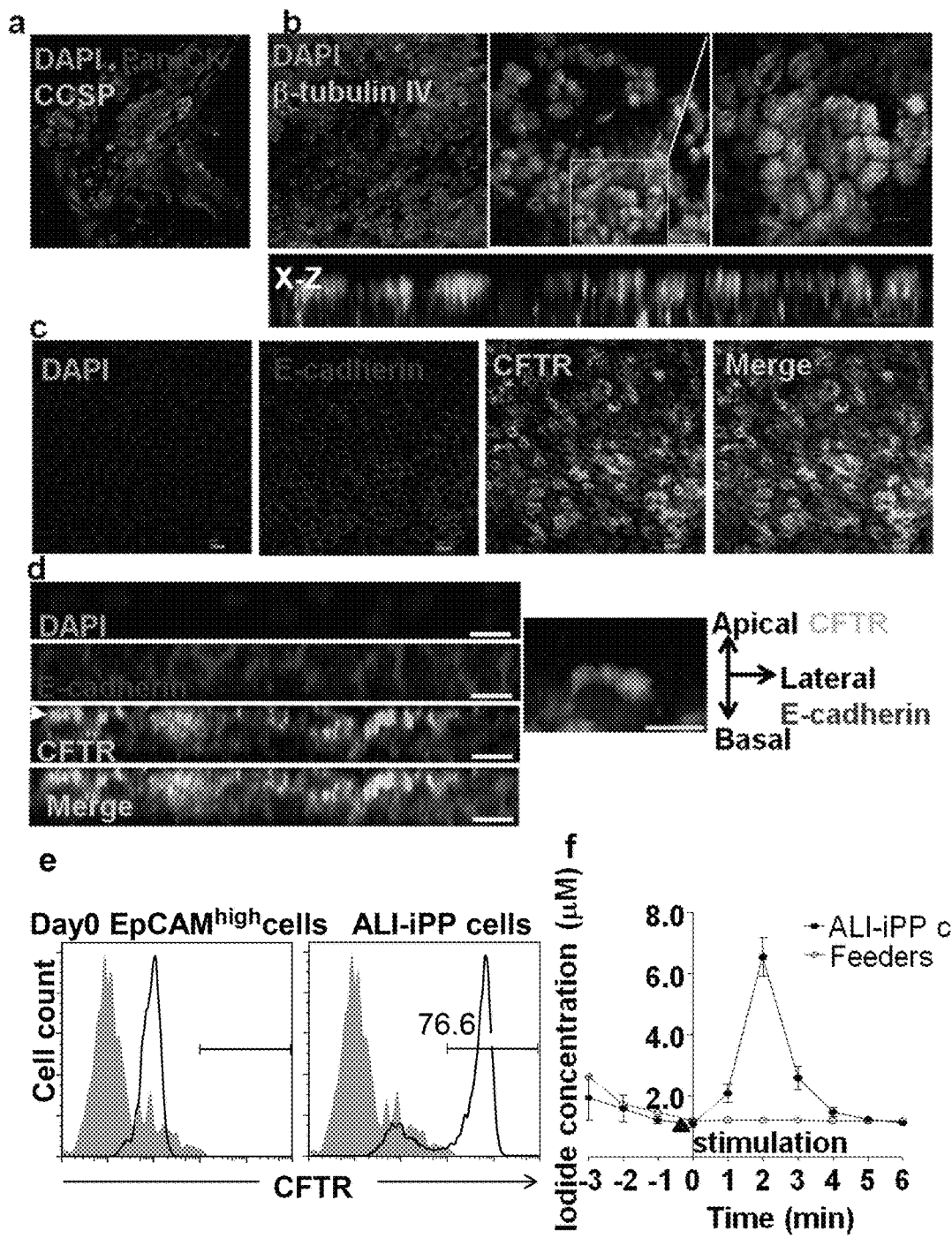
FIG. 4 iPP cells are able to generate functional CFTR-expressing ciliated epithelium. (a) Confocal microscopy images showing immunostaining of iPP cells before ALI differentiation, with nuclear stain DAPI, Pan-CK and CCSP. (b) Immunostaining of iPP cells following culture in 3D Matrigel™-based ALI system with nuclear stain DAPI and β-tubulin IV; (c) with nuclear stain DAPI, E-cadherin and CFTR. (d) Reconstruction of X-Z projections of horizontal sections showing nuclear stain DAPI, the apical membrane staining of CFTR and the lateral membrane staining of E-cadherin. (e) Flow cytometry analysis of CFTR expression in day 0 fresh isolated $EpCAM^{high}$ cells (left) and ALI-conditioned cells (right). (f) Iodide efflux assay showing CFTR activity in ALI-iPP cells induced by cyclic AMP agonist. Expression of (g) CCSP, FoxJ1, and CFTR, as measured by qRT-PCR comparing fold-differences in expression in freshly isolated cells (Day 0), 3-week induced cells with subsequent 2-week culture in Doxycycline-free media (3 W$^{+Doxy}$+2 W$^{-Doxy}$), and 3 W$^{+Doxy}$+2 W$^{-Doxy}$ cells maintained in 3D Matrigel™-based ALI culture system for 2-3 weeks. In e, data are representative of a minimum of three biological replicates. For f-h, values are mean±S.D. of triplicate samples. *, p<0.05; , p<0.001; *, p<0.0001. Scale bar, 10 μm (a-d).
Figure 4:
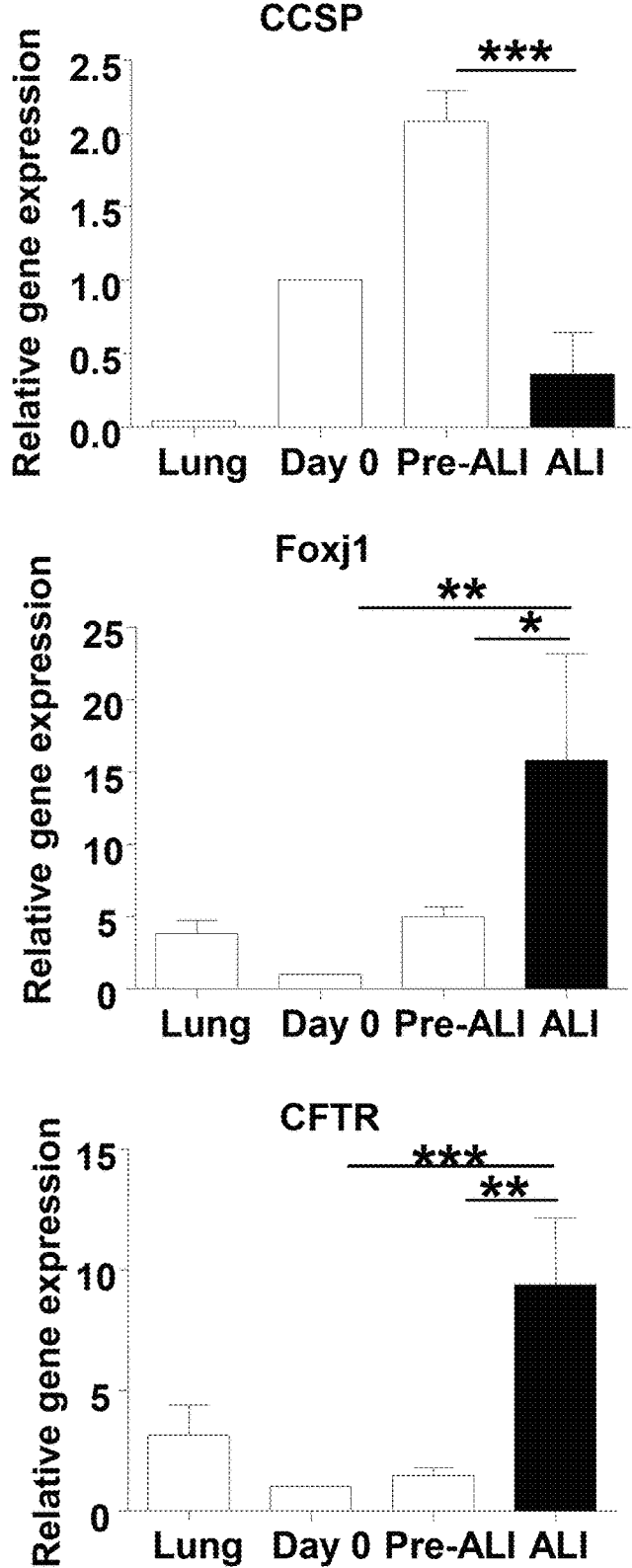

The majority of 3-week induced EpCAM$^{high}$-Clara cells were positive for pan-CK and CCSP following a 2 week withdrawal from doxyclyine, indicating a capacity to differentiate after induction as shown in FIG. 4a.

The induction period of time can vary for example according to the culture method and cell type. Embodiments, where a 2D culture system is used remain IPP under induction for longer periods of time. In one embodiment, the transient induction is for a time period of less than 6 weeks, less than 5 weeks, less than 4 weeks, less than 3 weeks, less than 2 weeks or less than 1 week.

In another embodiment, the number of induced progenitor cells in the induced cell population increases at least 5-fold, 10-fold, 20-fold, 30-fold, 50-fold, 100-fold or more during the period of transient induction.

The fold-increase in number of cells in the induced population is determined relative to the starting population of cell which express the exogenous induction factors. As indicated in FIG. 3c, EpCAM$^{high}$-Clara cells undergo an approximately 30-fold expansion during a 3-week induction.

In another embodiment the transient induction is terminated by optionally washing the iPP population of cells and/or culturing the iPP population of cells in a withdrawal culture medium.

In an embodiment, the cells are cultured in withdrawal medium for at least 3 days, at least 1 week, at least 2 weeks, at least 3 weeks or more. Withdrawal continues for example until exogenous factors have been sufficiently silenced which can be tested, for example by measuring cell protein levels at different points after withdrawal.

In yet another embodiment, the iPP population of cells is cultured with a withdrawal culture medium until the expression level of the reprogramming factors is decreased by at least 4-fold, 6-fold, 10-fold or more to produce an expanded withdrawal cell population expressing one or more lineage markers of the starting cell population. In an embodiment, exogenous and endogenous levels of the reprogramming factors are silenced (e.g. level of expression as seen in differentiated cell of similar cell lineage).

In another embodiment the withdrawal cell population is cultured with one or more differentiation factors and/or under conditions that promote differentiation.

A number of differentiation factors and differentiation conditions that promote differentiation of specific cell types are generally known in the art. Differentiation of epithelial cells may, for example, be promoted by air-liquid interface (ALI) culturing methods. Clara cells generated from EpCAM$^{high}$-Clara-derived iPP cells were able to differentiate into ciliated epithelial cells using ALI-culturing as indicated Example 1 and FIG. 5b.

Accordingly, another aspect provides a method of generating an expanded population of differentiated cells, comprising:

a) producing an induced progenitor population (iPP) of cells from a starting cell population as described herein;

b) culturing the iPP cells with a withdrawal culture medium to generate a withdrawal cell population, the withdrawal culture medium lacking inducing agent; and optionally c) differentiating the withdrawal cell population by culturing the withdrawal cell population under conditions that promote differentiation to produce a differentiated population of cells.

In an embodiment, differentiating the withdrawal cell population by culturing the withdrawal cell population under conditions that promote differentiation includes culturing the cell population in media comprising insulin, transferrin, EGF, HGF, and/or FGF-10. In an embodiment, the media is an EpiS medium comprising EGF, FGF-10, HGF and optionally MEF secreted factors.

Withdrawal can for example result in loss of pluripotency and return to a population of cells that expresses at least one of the markers of the isolated starting population prior to transient induction. This population can be further differentiated, for example by addition of differentiation factors and/or use of specific culture methods.

In one embodiment conditions that promote differentiation comprise culturing the iPP cells after withdrawal of transient induction in an air-liquid interface (ALI) culture system. The ALI configuration mimics the physical conditions of airways in vivo. It drives differentiation and induces ciliogenesis (Kesimer 2009; Lin 2007).

In another embodiment the culture system comprises a 3D culture matrix. In yet another embodiment the 3D culture matrix is supported by feeder cells.

In another embodiment, differentiating the withdrawal incubation step lasts until a desired population is obtained for example, a population that is corresponds to an isolated starting population and expresses at least one lineage marker of the starting population and/or which is more or less differentiated than the starting population. For example, the withdrawal population can be cultured for up to about 3 weeks. This culture period can comprise different steps including addition of different differentiation factors and/or methods.

In one embodiment, the cells are differentiated to CFTR expressing ciliated epithelium, for example Clara cells and/or ciliated epithelial cells. For example the expanded population can return to the original first-Clara cell, then differentiates to ciliated cells as do native Clara cells. In another embodiment the cells are differentiated to AT-1 cells. For example the expanded population can return to AT-II. AT-II can also differentiate to AT-I, if for example AT-I is the desired cell type.

In yet another embodiment, culturing the induced cell population after withdrawal of the inducing agent comprises culturing in epithelial medium in a 3D matrix culture optionally with the support of feeder cells.

In an embodiment, the conditions that promote differentiation comprise an air-liquid interface (ALI) culture system. In another embodiment, the ALI culture system comprises a 3D culture matrix with support of feeder cells.

As mentioned above, the progenitor cells have an increased ability to proliferate compared to the starting population. In one embodiment, the number of cells making up the withdrawal population of cells and/or the differentiated population of cells is at least 5-fold, 10-fold, 20-fold, 30-fold, 50-fold, 100-fold or more, than the number of cells making up the starting cell population prior to transient induction.

It is demonstrated herein that the methods can be used with epithelial cells and particularly Clara cells.

Yet another aspect provides a method of producing an expanded population of epithelial lineage cells, comprising the steps:

a) obtaining a starting population of Clara cells;

b) introducing into the starting population one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent;

c) transiently inducing expression of the reprogramming factors in the starting cell population for a period of time by adding an inducing agent to obtain an iPP population of cells;

d) optionally isolating the iPP and e) terminating the transient induction while the proliferative capacity of the iPP remains under the control of the one or more exogenous reprogramming factors to produce an induced population of cells.

f) culturing the induced cell population after withdrawal of the inducing agent in epithelial medium, to generate a withdrawal cell population comprising cells expressing one or more markers selected from Pan-CK, EpCAM, Claudin 10 and E-Cadherin.

The method for example optionally comprises differentiating the withdrawal cell population by culturing the withdrawal cell population under conditions that promote differentiation to produce a differentiated population of cells.

In an embodiment, obtaining a starting population of Clara cells comprises isolating a population of cells enriched in EpCAM$^{high}$-Clara cells relative to the antecedent population of cells. In an embodiment, isolation of the population of cells enriched in EpCAM$^{high}$-Clara cells from the antecedent population comprises using FACS to isolate cells on the basis of cell surface expression profile. In another embodiment, the cell surface expression profile comprises CD31$^{neg}$/CD45$^{neg}$/EpCAM$^{high}$ cells. In one embodiment, the starting population of Clara cells enriched in EpCAM$^{high}$-Clara cells comprises at least 80%, at least 90%, at least 95%, or about 100% of EpCAM$^{high}$-Clara cells.

As mentioned, the inducible control element comprises a tet-on or a tet-off promoter system. In an embodiment, induction comprises adding or withdrawing an inducing agent, wherein the inducing agent is tetracycline or a tetracycline derivative such as doxycycline. In an embodiment, cells are induced by adding doxycycline for a selected period of time then doxycycline is withdrawn for a selected period of time. In yet other embodiments the inducible control element is comprised optionally with the exogenous reprogramming factor polynucleotides in an excisable integration system. For example the inducible control element and the exogenous reprogramming factors may be flanked by loxP sites and excisable using Cre. Other excisable integration systems can also be used.

As described herein, cells induced to express reprogramming factors can traverse to become pluripotent. Such cells also have a number of applications.

Accordingly, in another aspect is provided a method of producing an induced pluripotent stem (IPS) cell population from somatic cells, comprising the steps:

a. obtaining a starting cell population;
b. introducing into the starting population one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent;
c. transiently inducing expression of the reprogramming factors in the starting cell population for a period of time to obtain an induced pluripotent stem cell population of cells, and
d. terminating the transient induction at a point during the induction when the proliferative capacity of the cell population is independent of the one or more exogenous reprogramming factors to produce an iPS cell population.

In an embodiment, the starting cell population is a Clara cell comprising population, optionally isolated as described herein.

In another embodiment, the inducing transient expression is performed using a 3D Matrigel™ culture system.

In an embodiment, the method comprises:
a) Isolating a starting cell population from an antecedent cell population;
b) introducing into the starting population one or more exogenous nucleic acid molecules encoding one or more reprogramming factors each operably linked to an inducible control element, the one or more reprogramming factors comprising Oct4, Klf4, Sox2, c-Myc, Nanog, and/or Lin28, and the inducible control element directing expression of the reprogramming factor(s) under its control in response to the presence or the absence of an inducing agent; and
c) transiently inducing expression of the reprogramming factors in the starting cell population for a period of time to obtain an induced pluripotent stem cell population of cells, and
d) terminating the transient induction at a point during the indication when the proliferative capacity of the induced pluripotent stem cell population is independent of the one or more exogenous reprogramming factors to produce an induced population of cells.

Also a further aspect provides an isolated induced population cells produced by the methods described herein, or cells derived and/or differentiated therefrom. The isolated population can comprise a diluent and/or carrier and can be further purified or isolated to provide a subset of a population described herein.

In an embodiment, the cells have been deleted of the inducible construct, for example using the Cre-Lox system or the PiggyBac transposon system.

Another aspect provides a composition comprising an isolated induced population cells generated by the methods described herein, or cells derived and/or differentiated therefrom, and a diluent and/or carrier.

Acceptable diluents include for example, culture media, buffered salines and/or other cell suitable diluents. Cells produced according to the methods described herein can be suitably resuspended in freezing media for example comprising culture media, serum DMSO and/or glycerin. Cells can for example be stored in a sterile vial or other cell suitable vessel.

Cells can be used for a number of purposes including, engrafting, cell therapy and/or drug screening.

Yet another aspect provides a method of engraftment or cell therapy comprising:
a) obtaining a population of cells consisting of the cells prepared by any of the methods described herein, the starting population of cells being donor cells harvested from a donor; and
b) administering the population of cells derived from the donor cells to a target tissue, scaffold, or subject in need thereof.

Cells can be administered for example by direct introduction, depending for example on the cell type and the site to be targeted. For example, lung cells can be administered transtracheally and/or systemically.

Cells can also for example be used to recellularize scaffolds.

In another embodiment, the subject is human. The subject may have for example sustained an injury (e.g. a burn, naphthalene induced injuries, bleomycin induced injuries) or have a condition comprising nonfunctioning cells, such as epithelial cells with CFTR mutation.

In yet another embodiment, the donor cells are autologous or non-autologous.

In another embodiment the engraftment occurs ex vivo or in vivo.

In an embodiment, the cells are exposed to one or more cycles of induction.

Cyclical induction can enhance the cell replacement potential of engrafted iPP-derived cells relative to uninduced cells. For example, as demonstrated herein in FIGS. 19B and C, engrafted iPP-derived cells can engraft after in vivo cyclical induction. It is also shown herein that the expression of the transgene 4F2A is not expressed in non-treated lung cells and that it can be activated under doxycycline treatment and down-regulated or silenced upon removal of doxycycline.

Cyclical induction can also efficiently restore CCSP (Clara cell secretory protein) expression of recipient airways. As shown herein in FIGS. 19D and E, cyclical induction of doxycycline can engraft and restore the CCSP expression of injured epithelium.

Figure 20:
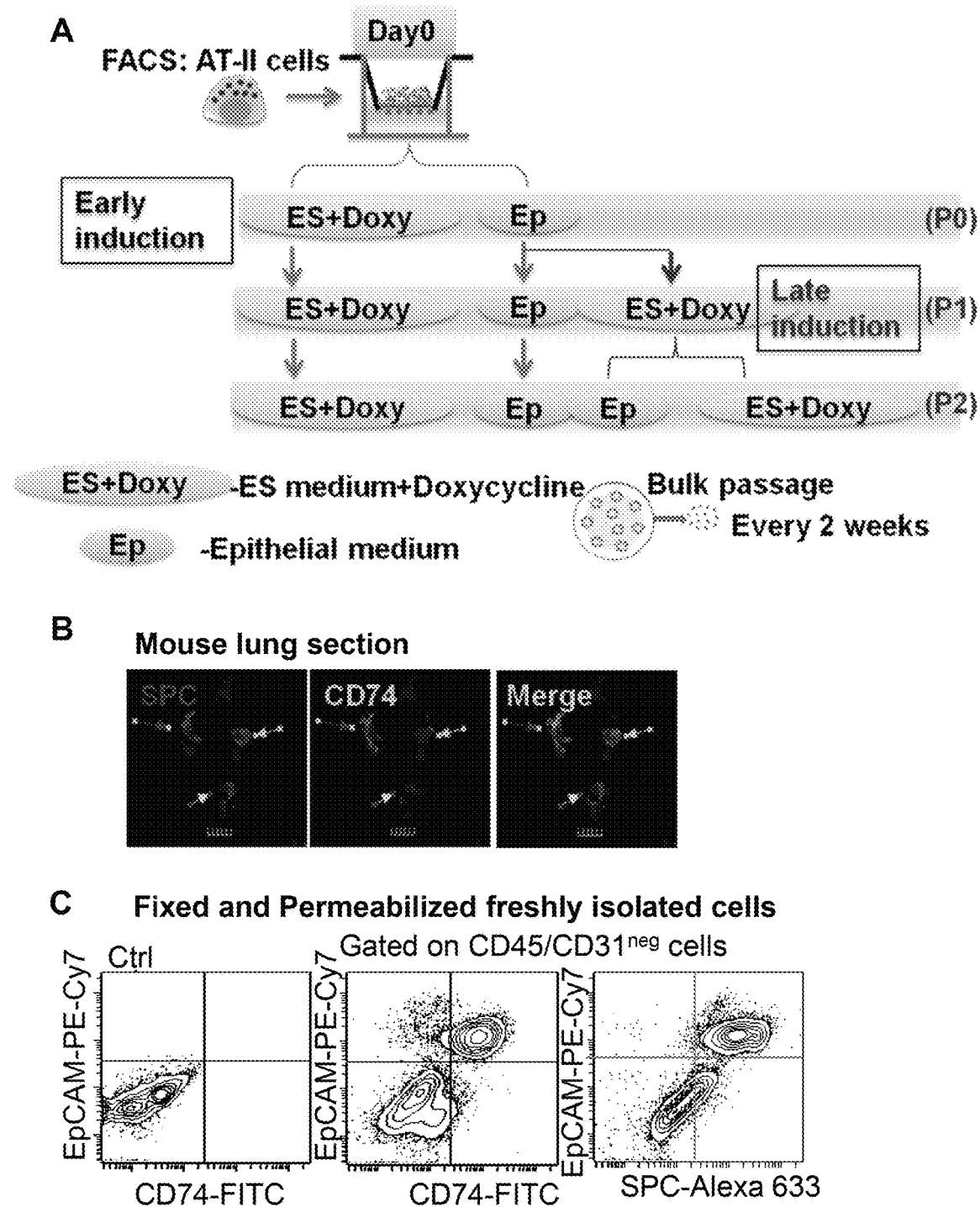
FIG. 20 (A) is a scheme showing induction of AT-II cells with doxycycline. (B) is a graph showing immunohistochemical staining of frozen mouse lung sections of Spc and CD74. (C) is series of graphs showing a flow cytometric analysis of SPc and CD74 expression in freshly isolated AT-II cells. (D) is a series of images showing the colony forming ability of AT-II cells under iPP induction. (E) is a graph showing colony forming efficiency of AT-II cells under iPP induction. (F) is a graph showing cell number counts of AT-II cells under iPP induction. Values are mean±S.D. of triplicate samples. *, p<0.05; , p<0.001; *, p<0.0001. (G) depicts confocal microscopy images of AT-II derived colonies under different treatments, day 0-AT-II cells (top left), 4-week without doxycycline treatment (top right) and iPP induced cells (2 $W^{ND}$+2 $W^{+Doxy}$) (bottom), showing nuclear stain DAPI (blue), proSPC (green), EpCAM (red). Scale bar, 10 μm. (H) depicts confocal microscopy images of AT-II derived colonies at week 4. 4-week without doxycycline treatment (4 $W^{ND}$) (left) and iPP induced cells (2 $W^{ND}$+2 $W^{+Doxy}$) (right), showing nuclear stain DAPI (blue), proSPC (green), T1α, (red). Scale bar, 10 μm. (I) depicts confocal microscopy images of AT-II derived colonies at week 6. Colonies in 2 $W^{ND}$+4 $W^{+Doxy}$ (top) and 2 $W^{ND}$+2 $W^{+Doxy}$+2 $W^{ND}$ roup (bottom), of which the inductive factors were withdrawn for 2 weeks after a 2-week late induction, showing nuclear stain DAPI (blue), proSPC (green), EpCAM (red). Scale bar, 100 μm and 10 μm (zoom).
Figure 20:
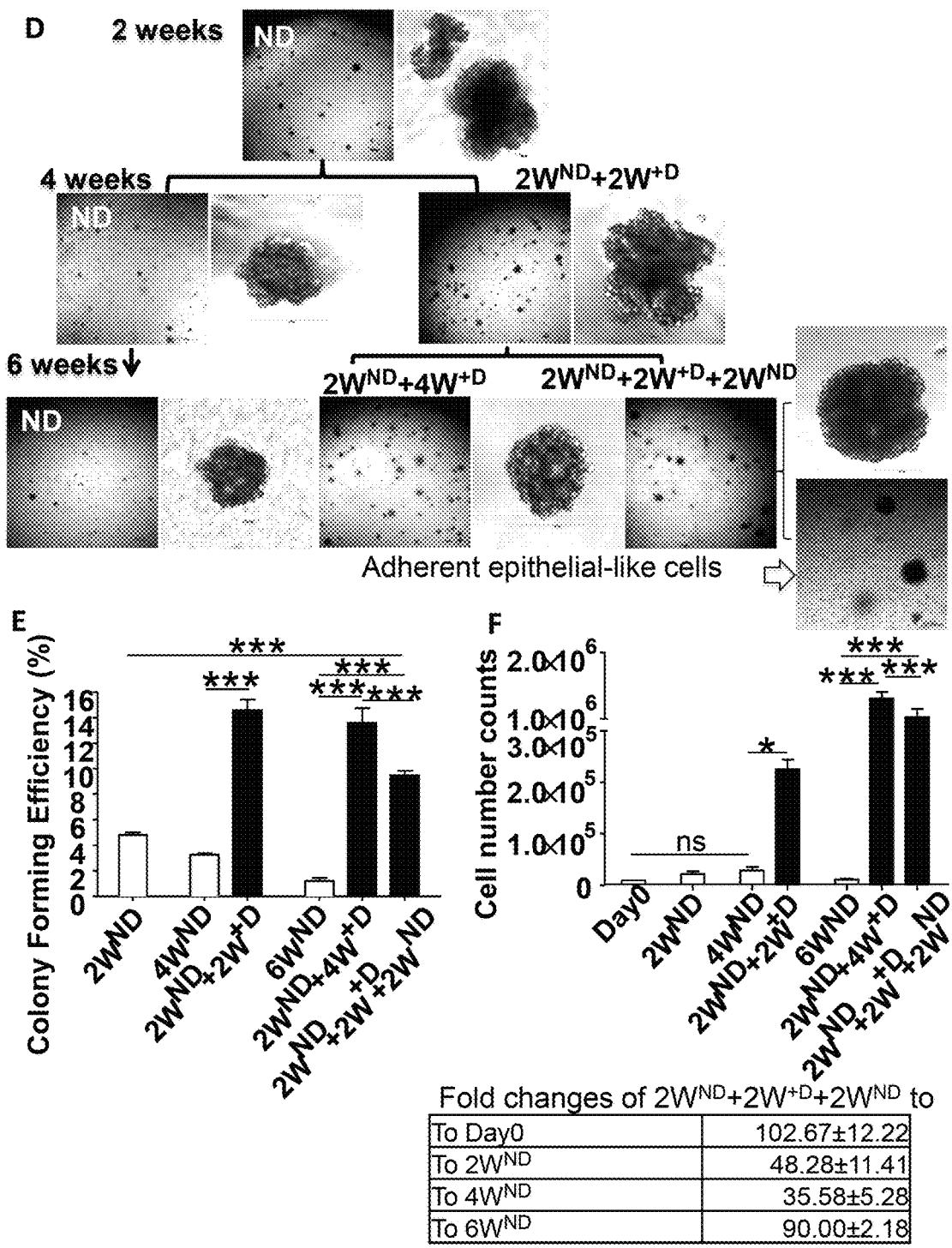
Figure 20:
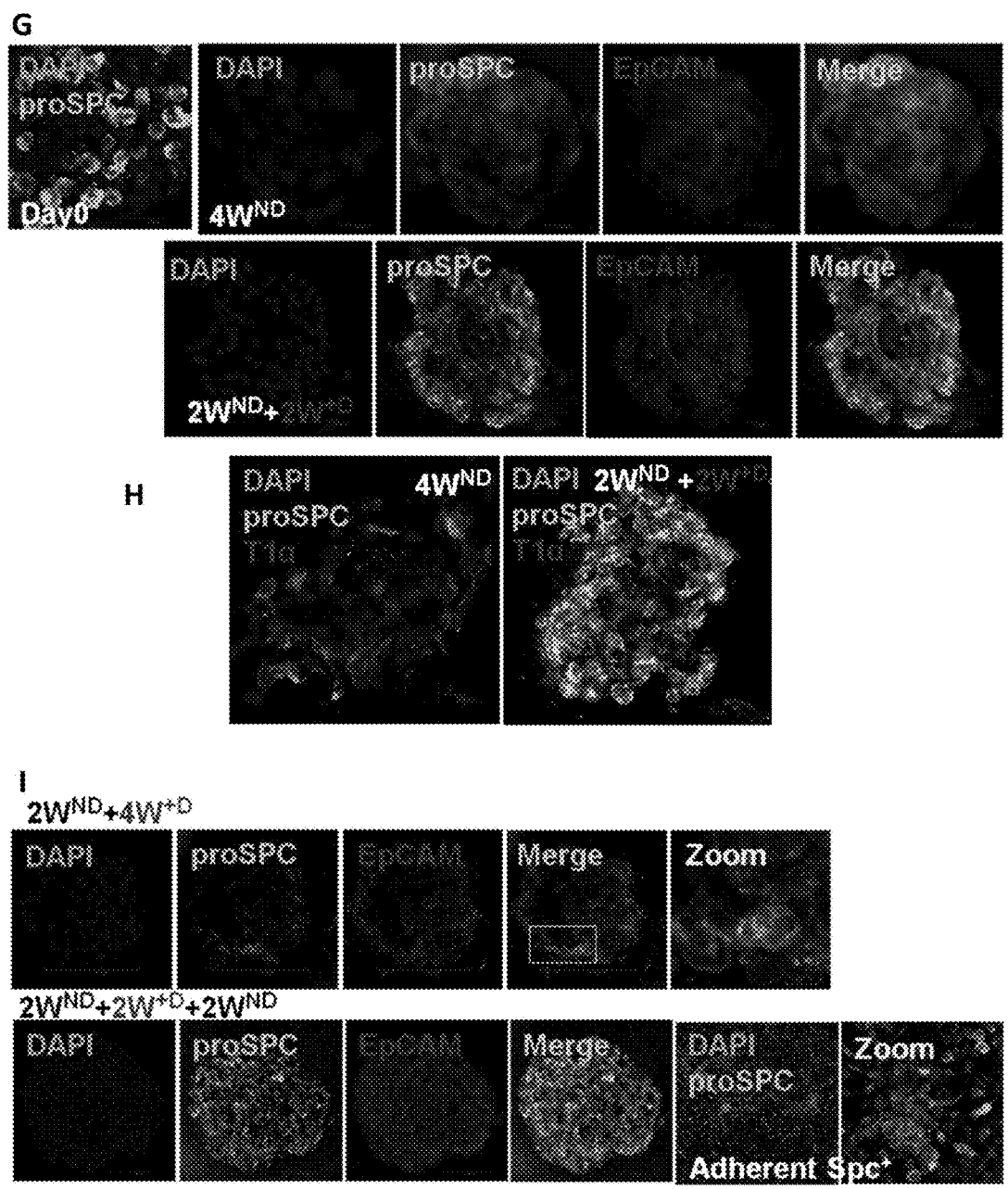

It is also demonstrated herein that iPP induction can rescue the limited passaging capacity of lung cell AT-II colonies and expand cells in vitro. For example, as shown in FIG. 20D-F, induction or late induction, for example a 2-week late induction, can significantly increase the colony forming efficiency and total number of AT-II cells. It is shown herein, at FIG. 20G, that the induced colonies are alveolar-like colonies that express a higher level of Spc and EpCAM compared to the non-treated group.

In an embodiment, induction conditions for AT-II cells progenitor cells comprises late induction. For example, late induction can comprise differentiating the cells in Matrigel for 2 weeks prior to exposing to doxycycline. As demonstrated in FIG. 20A, this 2-week "late induction" (2 $W^{ND}$+2 $w^{+Doxy}$) significantly increased the colony forming efficiency (FIG. 20D-E) and total number of cells (FIG. 20F). Importantly, these induced colonies are alveolar-like colonies expressing higher level of SPC and EpCAM, compared to non-treated group (FIG. 20G). Furthermore, the differentiation status of colonies can be evaluated by immunostaining of AT-I cell marker (T1α). As demonstrated herein, in non-doxycycline treated group (ND), AT-I cell markers are greatly up-regulated at both gene (AQP5) and protein (T1a) levels (FIG. 20H), indicating the differentiation of AT-II cells to AT-I cells in vitro. Under late induction, more Spc+ and less T1α+ cells were found, which may suggest the de-differentiation of AT-II derived AT-I cells to the original clonogenic AT-II cells.

In yet another embodiment, the population of cells to be administered are tested for teratoma formation and or pluripotency markers (e.g. if an iPP derived cell population is desired) prior to administration. Cells that are not teratoma forming and/or that do not express pluripotency markers and/or that express differentiation markers can be administered. These cells can, for example, also be modified to remove the induction factor construct using, for example, a Cre-Lox system or PiggyBac transpon system if applicable.

The population administered (or for administration) can be iPP or differentiated therefrom. In yet another embodiment, the withdrawal population of cells and/or the differentiated population of cells is administered to a subject.

It is demonstrated, herein that iPP cells can differentiate to CFTR expressing cells in vivo in CFTR-KO lungs.

As shown herein, the cells produced using the methods described can be used to replace injured cells.

Another aspect provides a use of an isolated population cells (iPPs) generated by the methods described herein, or cells derived and/or differentiated therefrom, for engraftment or cell therapy in a subject in need thereof. In one embodiment, the subject is human.

Another aspect provides a method of drug screening. For example, primary cells can be expanded providing for a more appropriate cell population than cell lines for drug screening.

In an embodiment, the method comprises testing a putative drug compound, the method comprising:
a) obtaining an induced population of cells produced according to a method described herein;
b) contacting the cell population with a test compound; and
c) assessing the effect of the test compound on the cell population compared to an untreated control.

The screening methods described herein can permit for example, personalized testing as cells from a patient can be harvested and tested.

In an embodiment, the method comprises:
a) obtaining an induced cell population prepared according to any of the methods described herein from a starting population, wherein the starting cell population harvested from a subject, such as a human subject;
b) contacting the cell population with a test compound; and
c) assessing the effect of the test compound on the cell population compared to an untreated control.

The effect of the drug assessed will depend for example on the test compound and the desired effect. If the desired effect is to increase or decrease of a factor, the level of the factor is assessed.

In an embodiment the test compound is for the treatment of cystic fibrosis.

Patient specific screening methods comprise a step of generating an iPP of cells from a patient sample. The generated cells, or cells derived therefrom, may be used to assess the response of the cells to one or more test compounds or to assess disease-related cellular function and/or characteristics. For example, airway epithelial cells isolated from a patient may be used to generate patient-specific CFTR expressing ciliated cells (e.g. ciliated cells can be identified by positive staining for ciliated cell specific marker β-tubulin IV), which may be assayed in Ussing chambers to test the functionality of CFTR. Differentiated cells can be assessed to see if they form tight monolayers in 24 well plates and be utilized in Ussing chambers (used to measure chloride transport across epithelial membranes). This can be used to test the functionality of CFTR in a population of cells with and without prior treatment of the cells to test compound.

Another aspect provides a use of the cell populations prepared according to any of the methods described herein, with or without a diluent, for drug screening.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Materials and Methods

Animal Husbandry

ROSA26-rtTA and Col1a1:tetO-4F2A mice, purchased from Jackson's lab (011004) were used to generate inducible lung epithelial cells. The system makes use of doxycycline to activate the tet promoter which subsequently drives expression of doxycycline-inducible polycistronic 4F2A cassette from the Col1a1 locus. Animals were maintained as an in-house breeding colony under specific pathogen-free conditions.

Naphthalene Administration and Cell Delivery

Adult (6- to 8-week-old) female mice C57/BL6 and CFTR-knockout mice (Jackson Laboratory) were used for naphthalene treatment studies. Naphthalene (>99% pure; Sigma-Aldrich, St Louis, Mo.) was dissolved in Mazola corn oil and injected intra-peritoneally between 8:00 and 10:00 A. M. at a dose of 200 mg/kg as previously described [21]. Busulfan (Otsuka America Pharmaceutical, Rockville, Md.) was given by intra-peritoneal injection 1 day after naphthalene treatment at a dose of 20-50 mg/kg and donor cells were transplanted the following day ($10^6$ cells in 50 μl PBS) transtracheally using sterile gel-loading tips. The mice received donor cells were rotated to ensure equal dispersion of cell suspension to both lungs.

Isolation of Clara Cells from Mouse Lung

Mice were injected intra-peritoneally with heparin (250 U/mouse) and sacrificed by CO2 narcosis. Before lung dissection, lungs were perfused through the right ventricle with cold phosphate buffered saline (PBS) (~10 mL) to remove blood by directing the catheter towards the main pulmonary artery. Endo-bronchial lavage was then performed to remove alveolar leukocytes. Clara cells were isolated using a previously described protocol (Atkinson et al, 2008) with modifications. Briefly, lungs were instilled with 0.5 mL of 1% low melting temperature agarose in PBS through the trachea then placed on ice for 2 min. For lung digestion, 0.5~1 mL of 0.25% trypsin was instilled into the lung followed by ligation of the trachea with a suture. Lungs were incubated for 10 min at 37° C., then lung tissue was teased away from the large airways, finely minced to 1 mm² pieces and placed in 250 μg/mL of DNAse I in DMEM containing antibiotic for 10 min minutes. The suspension was transferred to a 50 mL tube, and FBS was added to 10% of final volume. The suspension was sieved through 100 and 40 μm nylon meshes and centrifuged at 200 g for 10 minutes. The cell pellet was re-suspended in red blood cell lyses buffer for 3 min to remove the extra red blood cells and the lysing was stopped by addition of an equal volume of PBS. Cells were centrifuged at 40 g for 6 min then re-suspended in 10% FBS-DMEM and centrifuged 2 more times at 40 g for 6 min. The final pellet was suspended in 0.5% vol/vol FBS-PBS for all subsequent procedures.

Fluorescence Activated Cell Sorting and Analysis

For purification of epithelial cells, fresh isolated cells were suspended and incubated in 0.5% vol/vol FBS-PBS containing an optimally pre-titered mixture of antibodies [anti-CD45, anti-CD31 (BD Biosciences), anti-EpCAM (Abcam) and relevant isotype controls] for approximately 30 min on ice. Labeled cells were washed in 0.5% vol/vol FBS-PBS, re-suspended at $3\sim5\times10^6$ cells/mL, and held on ice for flow cytometric analysis and sorting. Cell viability was accessed by propidium iodide (1 μg/mL) staining. For intra-cellular antigen analysis, cells were fixed and stained using a Fix and Perm kit (Invitrogen) as manufacturer instructions. Sorting was performed using a Moflo BRU cell sorter (Becton Dickinson), aquisition was performed using a BD LSRII analyzer (Becton Dickinson) and data were analyzed using FlowJo software.

Immunofluorescence

Immunoreactivity of different antigens was evaluated using immunofluorescence techniques. Briefly, samples were fixed with 4% paraformaldehyde (PFA) for 30 min and blocked with 5% goat serum and 2% BSA in PBS containing 0.5% Triton X-100 for 1 hour. Primary antibodies were diluted in BSA/PBS, applied to samples and incubated overnight at 4° C. Secondary antibodies AlexaFluors 488, 532, 546, 633 or 647 (Invitrogen) were applied according to the species in which the primary antibody was used for 2 hours at room temperature. Nuclear staining was performed using 2 mg/ml 4, 6, diamidino-2-phenylindole (DAPI; Sigma). Stained samples were mounted with immunofluorescent mounting medium (DAKO). Appropriate non-specific IgG isotypes were used as controls for the antibodies. Immunoreactivities of antigens were visualized as single optical planes using an Olympus Fluoview confocal microscope and analyzed using FV10-ASW 2.0 Viewer software.

Real-Time PCR Analysis

Total RNA was prepared from sorted fresh cells and cultured cells using the RNeasy® Kit (Qiagen) as per manufacturer's instructions. Equal amounts of mRNA were used for each cDNA synthesis reaction. cDNA was prepared and assayed using Superscript® III (Sigma) according to manufacturer's protocol. Differential gene expression was determined using SYBR® green detection (Roche). All Real-time PCR reactions were done in triplicate for each sample. GAPDH was used as a housekeeping gene to normalize gene expression levels using LightCycler® 480 software (Roche). Normalized mRNA levels were shown as relative to the control samples (day 0 fresh isolated cells or adult lung).

Cell Cultures:

Bottom-Feeder Conditioned CFSE Assay

CFSE (carboxyfluorescein diacetate, succinimidyl ester) cell proliferation assay was performed to evaluate the proliferative capacity of the induced cells. In order to separate seeding cells from feeders, a previously described[18] bottom-feeder seeding method was applied in which mitomycin treated in-activated mouse embryonic fibroblasts (MEF) feeders were seeded and allowed to attach to the bottom of the Transwell® (Corning) membrane one day prior to addition of sorted cells on the top of the membrane. CFSE working solution (10-15 μM/$10^6$ cells; Invitrogen) was prepared and applied to cells according to the manufacturer's protocol. Cell were labelled with CFSE at day 0 or 7 days after culturing and measured by flow cytometry as indicated in results.

Matrigel™-Based iPP Induction

Mitomycin treated in-activated mouse embryonic fibroblasts (MEF) were seeded on 0.1% gelatin coated 24-well Transwell® filter inserts (Corning) one day prior to the addition of epithelial cells. FAC sorted epithelial cells resuspended in 100 μL of Matrigel™ (BD Biosciences) prediluted 1:1 (vol/vol) with epithelial-specific (EpiS) media were added to a MEF-coated 24-well Transwell® filter inserts in a 24-well tissue culture plate containing 500 μL of epithelial media for 3-5 days then replaced with ES (embryonic stem cell) medium containing 1.5 μg/ml Doxycycline (Sigma). EpiS medium comprised of DMEM/F12 (Invitrogen) supplemented with 10% FBS, penicillin/streptomycin, 10 mg/ml insulin, 5 mg/ml transferring-selenium (Sigma), epidermal growth factor (EGF, 20 ng/mL; Sigma), fibroblast growth factor-10 (FGF-10, 50 ng/mL; R&D Systems) and hepatocyte growth factor (HGF, 30 ng/mL; R&D Systems). Media was replenished three times per week. For bulk passaging, whole cultures were dissociated in Collagenase (1 mg/ml; Sigma)/Dispase (3 mg/ml; BD Biosciences) in PBS to generate a single-cell suspension. For clonal passaging, single colonies were picked and dissociated in the Collagenase/Dispase solution.

Differentiation Assays:

Air-Liquid Interface (ALI) Differentiation Assay

To determine the ability of induced cells to generate ciliated cells a novel ALI system was developed. In comparison with the traditional ALI system, this Matrigel™-based 3D system, allows the differentiation to occur under the support of feeder cells, thereby enhancing the efficiency of ciliogenesis. Prior to the ALI assay, induced cells were cultured and recovered in ES medium for 2 weeks. For ALI culture, the ES medium from upper chamber was removed in order to expose cells to the air while medium of lower chamber was replaced with ALI-specific medium (Lonza). Media was replenished 2 times per week and cells were maintained under ALI conditions for 2-3 weeks.

In Vitro Pluripotency Assay

To elucidate the lineage preference of induced cells, an in vitro pluripotency assay using a previously described protocol (Shulamit Levenberg et al, 2003) was performed. Briefly, 3-week and over 8-week induced cells were dissociated then re-suspended in 50% (Matrigel™) and 20% FBS containing medium supplemented with the following growth factors have been shown to induce pluripotent stem cell differentiation: activin-A (20 ng/ml), transforming growth factor (TGF)-β1 (2 ngml), 10 g/ml insulin, 5 g/ml transferrin and retinoic acid (RA) (300 ng/ml) for 2-3 weeks. Lineage differentiation was accessed by immunostaining of Pan-Cytokeratin (endoderm epithelial cell marker), α-actinin (mesoderm cardiomyocyte marker) and β-tubulin III (ectoderm neuron cell marker).

Neuron Differentiation Assay

To further determine the lineage commitment of induced cells, a defined neuron differentiation assay (Millipore) was performed with a slight modification. Briefly, 3-week and over 8-week induced cells obtained from Matrigel™ cultures were digested to single cell suspension and differentiated in neuron conditions for 2-3 weeks following the manufacturer's protocol. The generation of neuron cells was accessed by immunostaining of β-tubulin III (a specific marker of neuron cells).

Statistics

Statistical analysis was performed using GraphPad Prism 5.0 statistical software (San Diego, Calif., USA). The statistical significance of multiple groups was compared to each other using Tukey's multiple comparison test ANOVA. A p value of <0.05 was considered significant Results:

Isolation and Identification of Distinct Lung Clara Cell Populations

Figure 7:
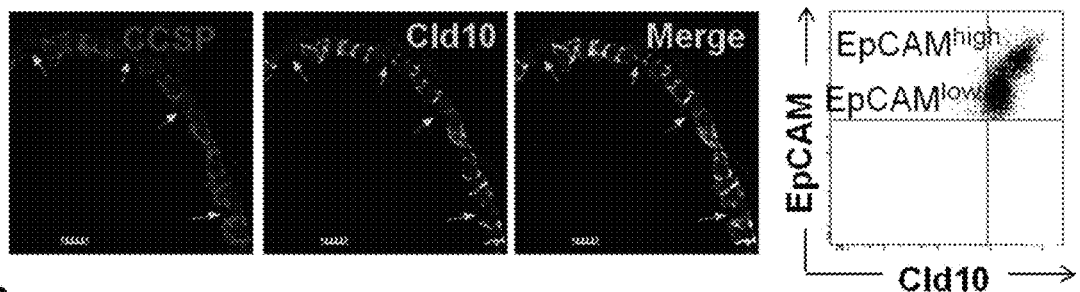
FIG. 7 (a)—left, representative confocol images showing immunohistochemical staining of frozen mouse lung tissue sections stained with DAPI nuclear stain and double-immunolabeled with anti-CCSP and anti-Cldn10 showing that Claudin10 is localized to the entire lateral surface of only CCSP cells (arrowheads show CCSP$^{neg}$, Cldn10$^{neg}$ cells). (a)—right, flow cytometry dot-plots showing freshly isolated lung cells, stained with antibodies against Cldn10 and EpCAM. (b) Flow cytometry analysis of freshly isolated lung cells, showing EpCAM-positive epithelial cells marked with antibodies specific for CCSP, pro-SPC, T1α, β-tubulin, Pro-collagen, and α-SMA. EpCAM$^{high}$ cells are exclusively Clara cells whereas the EpCAM$^{low}$ population is composed largely of Clara cells (>90% CCSP$^+$) with a small number of AT-II cells (<10%), which are positive for pro-SPC, the classic marker for AT-II cells. Both populations are negative for T1α (a marker for AT-I cells) and β-tubulin (a marker for ciliated cells).
Figure 7:
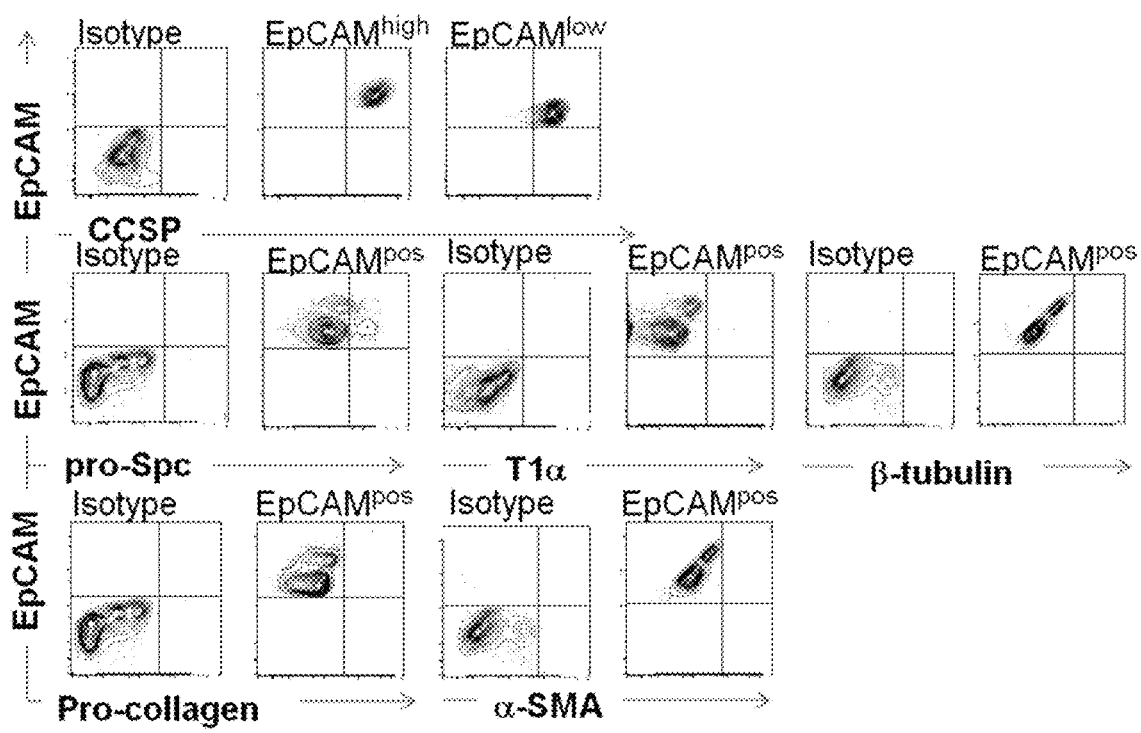
Figure 11:
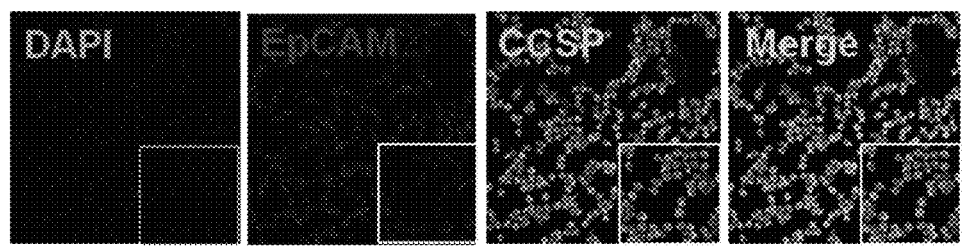
FIG. 11 (a) Confocal microscopy images of EpCAM$^{pos}$ cells stained with nuclear stain DAPI and CCSP, pro-SPC, T1α, β-tubulin, Pro-collagen, and α-SMA. Immunostaining indicated EpCAM$^{pos}$ cells are composed largely of Clara cells and a small number of AT-II cells, but not AT-I or ciliated cells. EpCAM$^{neg}$ cells are composed largely of fibroblasts, which are positive for pro-collagen and α-SMA. (b) Immunostaining of cytospined EpCAM$^{high}$ cells with CCSP antigen, confirming EpCAM$^{high}$ cells are CCSP-expressing cells. (c) The proliferation and differentiation status of EpCAM$^{high}$ cells compared to EpCAM$^{low}$ cells. EpCAM$^{high}$ have high expression levels of Hes1, which regulates the maturation of Clara cells. The EpCAM$^{low}$ population has abundant Foxp1, N-myc and β-Catenin expression indicating that the EpCAM$^{high}$ population is less proliferative than the EpCAM$^{low}$ population and it contains more differentiated cells, identified to be naphthalene-sensitive Clara cells.
Figure 11:
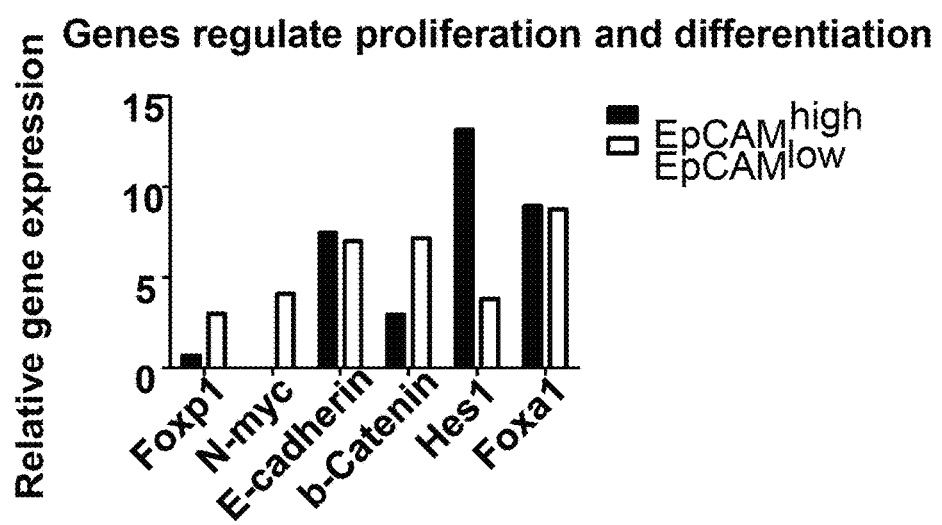

For iPP induction, a highly purified naphthalene-sensitive EpCAM$^{high}$ Clara cell population was identified, isolated and selected from mouse lungs. Clara cells were isolated using a modified Clara cell specific isolation protocol (Atkinson J et al., 2008) and subsequent FACS. Briefly, CD45$^{neg}$CD31$^{neg}$EpCAM$^{pos}$ lung epithelial cells were sorted according to EpCAM expression divulging two distinct epithelial populations, namely EpCAM$^{high}$ and EpCAM$^{low}$ (FIG. 1b). Flow cytometric analysis of freshly isolated lung cells, using antibodies specific for different epithelial cell types, indicated that EpCAM$^{high}$ cells were exclusively Clara cells expressing CCSP whereas the EpCAM$^{low}$ population was composed largely of Clara cells (~90%) (FIG. 1c) with a small number of type II alveolar epithelial cells (AT-II) cells (~10%) staining positive for pro-SPC. EpCAM$^{high}$ and EpCAM$^{low}$ cells were negative for type I alveolar epithelial cell (AT-I) marker, T1α and β-tubulin (a marker for ciliated cells) (FIG. 7b). Immunostaining confirmed that these EpCAM$^{pos}$ cells are composed of Clara cells and AT-II cells, but not AT-I or ciliated cells. EpCAM$^{neg}$ cells were composed largely of fibroblasts, staining positive for pro-collagen and α-SMA (FIG. 11a).

In order to confirm the Clara cell phenotype, Claudin 10 (Cldn10) was selected as an additional marker. Consistent with other studies (Zemke et al., 2009; Brook C et al., 2010) immunohistochemical staining of frozen mouse lung tissue sections double-labeled with anti-Cldn10 and anti-CCSP showed that Claudin10 was localized to the entire lateral surface of CCSP-expressing cells (FIG. 7a), arrowheads show CCSP$^{neg}$, Cldn10$^{neg}$ cells). Indeed, flow cytometry result showed all EpCAM$^{high}$ cells were positive for Cldn10 (FIG. 7a). Gene expression analyses of EpCAM$^{high}$ and EpCAM$^{low}$ cells comparing epithelial lineage-specific gene and Clara cell-related gene expression by real-time qPCR, showed that the EpCAM$^{high}$ population has a markedly higher CCSP expression (30.28 fold) compared to EpCAM$^{low}$ (2.37 fold). In contrast, sftpc expression is significantly higher in the EpCAM$^{low}$ population (53.57 fold vs 0.62 fold) compared to EpCAM$^{high}$ population. Clara cell-related genes Cyp2f2, Cldn10, Aox3, and Pon1 were detected within both populations whereas higher expression levels detected in EpCAM$^{high}$ population (FIG. 1d, e).

In parallel, in order to evaluate whether EpCAM$^{high}$ and EpCAM$^{low}$ populations contained functionally different subtypes of Clara cells, EpCAM expression in freshly isolated cells derived from naphthalene-treated (n=3) and non-treated mice (n=3) was compared. Flow cytometry results illustrated near ablation of Clara cells depicting the EpCAM$^{high}$ cells as naphthalene-sensitive Clara cells (FIG. 1f).

Figure 8:
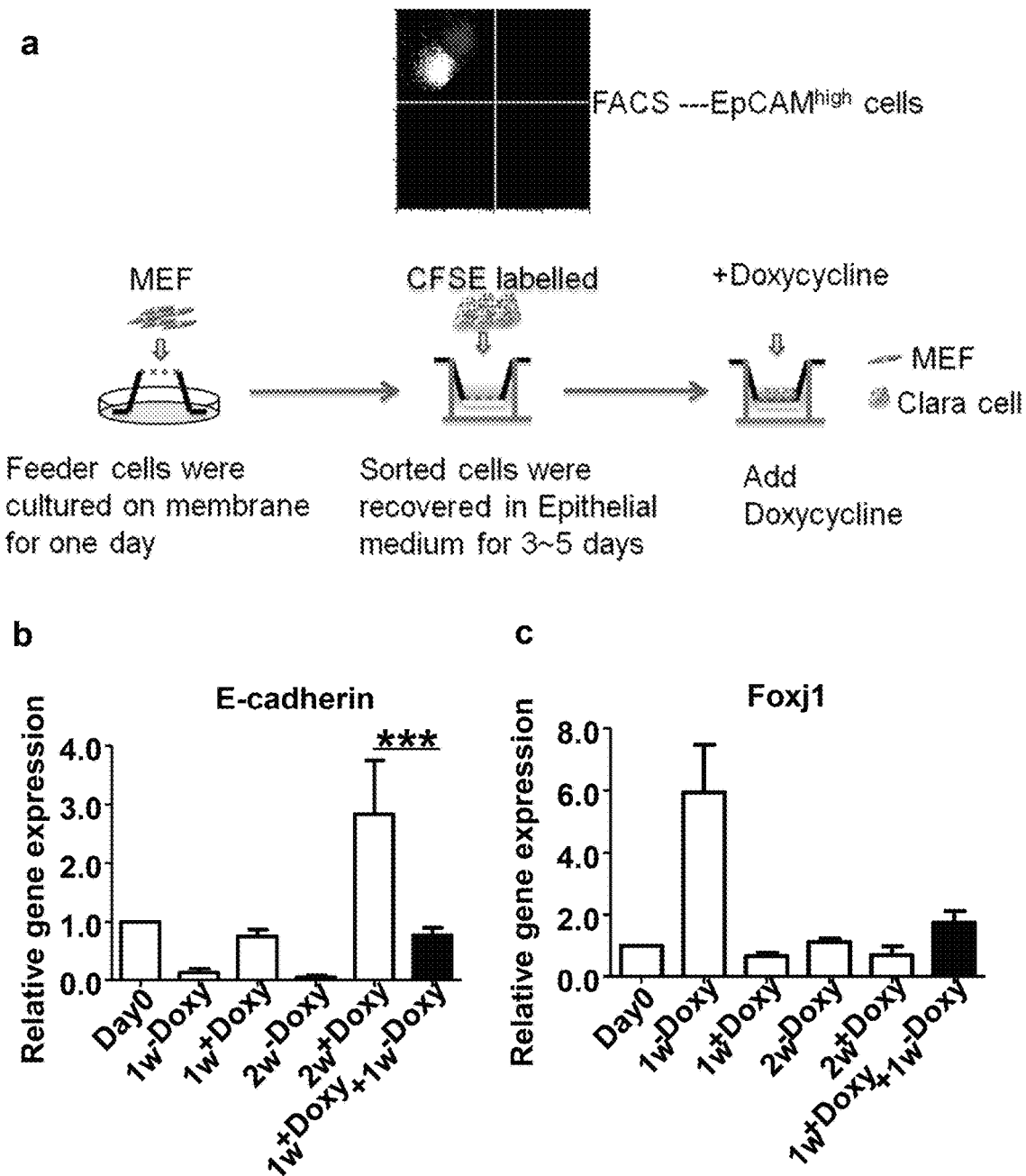
FIG. 8 (a) Schematic graph of bottom-feeder culture condition which enables the separation of seeded cells from supporting feeder cells. Expression of (b) E-Cadherin and (c) Foxj1, as measured by qRT-PCR comparing fold-differences in gene expression of in freshly isolated cells (Day 0), cells treated for 1 week with doxycycline (1 w$^{+Doxy}$), and induced cells cultured for an additional 1 week in the presence (2 w$^{+Doxy}$) and absence (1 w$^{+Doxy}$+1 w$^{-Doxy}$) of doxycycline.

Transient Induction Enables EpCAM$^{high}$-Clara Cells to Proliferate and Return to Quiescence Upon Withdrawal of Factors An advantage of the iPP concept is for example the possibility for expansion of epithelial populations. In order to measure the proliferative response of EpCAM$^{high}$ Clara cells to the inductive factors, feeders need to be excluded from detection. Thus, a previously described feeder-seeding method which can separate seeding cells from feeders to support the growth of human ES cells and reduce the contamination from feeders was tried (Sinae K et al, 2007). In the experiment design, feeders were seeded and attached to the bottom of the trans-well membrane one day before Clara cells culturing on the top of the membrane (FIG. 8a).

In order to obtain inducible EpCAM$^{high}$ Clara cells, EpCAM$^{high}$ cells were isolated and purified from ROSA26-rtTA and Col1a1::tetO-4F2A double transgenic mice allowing for doxycycline inducible induced pluripotent stem cell reprogramming transgenes (Oct4, Sox2, Klf4 and c-Myc) activation. To evaluate the proliferative response of EpCAM$^{high}$ cells to the inductive factors, cell were labelled with CFSE dye at day 0 and assessed for the presence of fluorescent dye at day 5, and 7 with or without doxycycline treatment. Flow cytometry results indicated that the inductive factors induce cell proliferation in EpCAM$^{high}$ cells and that doxycycline treatment results in a larger proportion of CFSE-negative proliferative cells to non-treated controls (FIG. 1g).

To further determine the proliferative capacity of these cells upon withdrawal of the reprogramming factors, both non-treated and doxycycline-treated EpCAM$^{high}$ cells were labelled with CFSE at day 7 followed by an additional 7-day culture with or without doxycline. CFSE staining demonstrated that withdrawal of reprogramming factors generated EpCAM$^{high}$-derived transient induced cells with limited proliferative capacity, showing EpCAM-positive quiescent-like cells with CFSE expression. In parallel, as expected continuous doxycycline treatment (14 days) resulted in CFSE$^{neg}$ EpCAM$^{neg}$ proliferative cells (FIG. 1h). Proliferation was confirmed by real-time quantitative RT-PCR (qRT-PCR) assessment of Cyclin D1 revealing limited expression in the day 7-doxycycline withdrawal group and significant up-regulation in the doxycycline-treated groups (FIG. 1i). Of note, it was confirmed that transgene construct 4F2A expression in the day 7 withdrawal group was silenced upon doxycycline withdrawal (FIG. 1i). Importantly, comparable levels of expression of lung epthelium-related genes, EpCAM and E-Cadherin in the withdrawal group and the day 0 EpCAM high cells were found (FIG. 1j). Similarly, levels of CCSP expression were upregulated in the withdrawal group, though still remain lower than the day 0 cells (FIG. 1k). These results suggest that these transiently induced cells mimic expression patterns of and possibly "revert" to the original EpCAM$^{high}$ cell phenotype.

Transient Induction Under Matrigel™-Based Colony Formation Conditions Results in Efficient Clonal Expansion of EpCAM$^{high}$-Clara Cells A more supportive culture system for epithelial cells, providing greater cell-cell contact with better mediation of paracrine factors was desired in order to induce a greater proliferation and expansion of the EpCAM$^{high}$ population. Thus, a Matrigel™-based colongenic 3D condition, previously shown to the self-renewal and differentiation potential of endogenous lung stem cells (McQualter et al., 2010), was modified for iPP induction as described in the Materials and Methods.

Flow cytometry sorted fresh EpCAM$^{high}$ cells were suspended in Matrigel™ and seeded on inactivated MEF feeders and treated with or without doxycycline. Under doxycycline treatment, EpCAM$^{high}$ cells exhibited clonogenic growth with colonies forming at days 4-5 and increasing in number over time. In contrast, no colonies were generated in non-doxycycline treated groups (FIG. 2a) demonstrating that EpCAM$^{high}$ cells lack progenitor clonogenic ability in Matrigel™ alone. At day 6, induced colonies were stained for EpCAM to determine their epithelial phenotype. Confocal microscopy z-series stained colonies showed that induced colonies are airway-like epithelial colonies with hollow lumens (FIG. 2b)

To assess self-renewal of induced colonies, bulk passaging of whole cultures was performed and showed that a subset of induced colonies retained colony-forming potential after serial passaging under doxycycline treatment (FIG. 2c, right Y axis). Importantly, there was a progressive increase in total cell number amounting to an approximately 30-fold expansion of day 0 seeded EpCAM$^{high}$ cells after a 3-week induction (FIG. 2c, left Y axis). To evaluate whether self-renewal was a function of induction time, single colonies were picked and passaged after 3, 4 and 5 weeks of induction. Colony-forming ability was measured after 7 days of culturing with or without doxycycline. Results showed that doxycycline-treated cells possessed greater colony-forming potential and 5-week induced cells treated with doxycycline had the highest CFU incidence among all the groups. Significantly, 3-week induced colonies were inductive factor-dependent and therefore no colonies were generated without doxycycline treatment (FIG. 2d). In contrast, few 4-week and 5-week induced colonies retained their clonal proliferation ability when doxycycline was withdrawn, suggesting attainment of a factor-independent stage in the reprogramming process; indicative of a phenomenal change between 3 and 5 weeks of induction. To determine the optimal time window for doxycycline withdrawal, induced colonies were characterized using Oct4 (a measure of transgene activation), Nanog (indicative of pluripotency), Pan-CK (showing epithelial phenotype) and CCSP (showing Clara cell phenotype) staining. 3 weeks of doxycycline treatment resulted in successful activation of the transgenes as shown by Oct4 immunoreactivity and sufficiently suppressed the expression of somatic markers-Pan-CK and CCSP. Importantly, negative staining for Nanog, confirmed that the cells had not yet gained pluripotency at 3 weeks induction (FIG. 2e). On the other hand, an additional 2 weeks in doxycycline (5 week induction), showed that 20-30% of induced colonies were able to express Nanog implying the potential of generating induced pluripotent stem cell cells (FIG. 2f). Thus, the time window for iPP induction was framed at sometime between 3 but less than 5 weeks of induction, at which time the greatest level of expansion was achieved without gaining pluripotency.

Optimized Transient Induction Allows EpCAM$^{high}$-Derived Colonies to Return to their Original Clara Cell-Phenotype Upon Withdrawal of Factors The ability of EpCAM$^{high}$-derived transiently induced colonies to return to their original phenotype following induction and subsequent culture without doxycycline was assessed. Colonies obtained at different time points were characterized by immunostaining for Nanog, Pan-CK and CCSP expression. 3-week induced colonies showed over 90% of multi-layered cells capable of expressing Pan-CK. Approximately 80% of the Pan-CK$^+$ cells expressed CCSP upon doxycycline withdrawal and subsequent 2 weeks of culture in epithelial medium (FIG. 3a). This result indicated that the majority of the 3-week induced cells were able to return to their original epithelial (pan-CK) and Clara (CCSP) phenotype following the 2 week withdrawal from doxycycline. Notably, in addition to "returning" to a Pan-CK$^+$ CCSP$^+$ phenotype, 3-week induced cells did not express the Nanog. On the other hand, when doxycycline was withdrawn one week later, at 4 weeks, the majority of the colonies were Nanog$^-$Pan-ck$^+$ (FIG. 3b) with 3 of the 49 colonies expressing Nanog (FIG. 3c). In addition, it was found that Pan-CK was not expressed by Nanog-positive+ cells, making it a more efficient epithelial marker than EpCAM, to identify epithelial property in reprogramming process since given the latter is also expressed by induced pluripotent stem cells.

Figure 9:
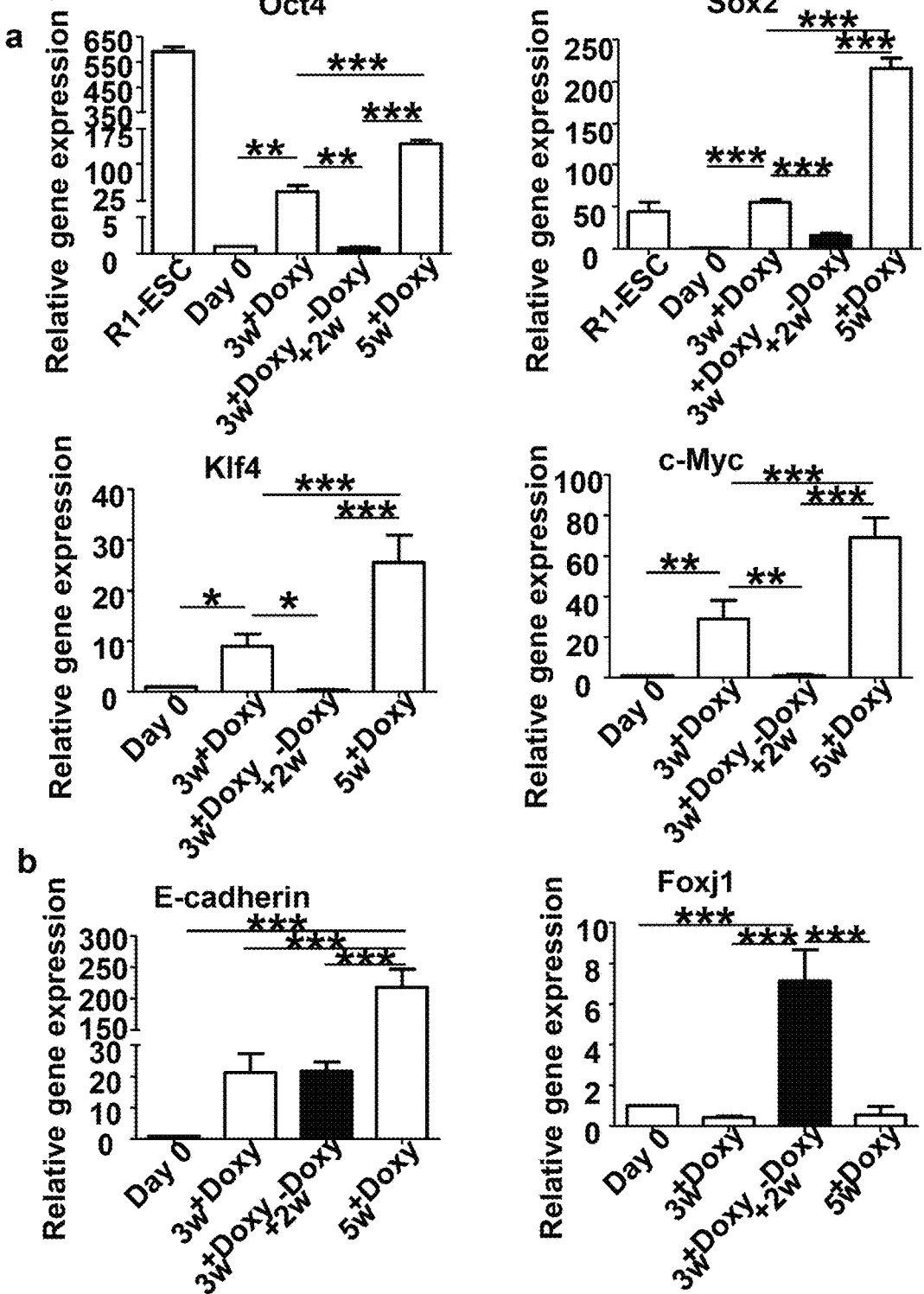
FIG. 9 Expression of (a) Oct4, Sox2, klf4, c-Myc, and (b) E-Cadherin, Foxj1, as measured by qRT-PCR comparing fold-differences in gene expression in R1-ESC cells, freshly isolated cells (Day 0), 3-week induced cells (3 W$^{+Doxy}$), 3-week induced cells with subsequent 2-week culture in Doxycycline-free media (3 W$^{+Doxy}$+2 W$^{-Doxy}$) and 5-week induced cells (5 W$^{+Doxy}$). For d-h, values are mean±S.D. of triplicate samples. *, p<0.05; , p<0.001; *, p<0.0001.

Gene expression analysis of colonies obtained from different groups confirmed a correlation between transgene activation and proliferation gene-CyclinD1 expression. Under doxycycline treatment, expression levels of transgene 4F2A and Cyclin D1 were both up-regulated over time. In parallel, 3-week induction following 2 weeks of doxycycline withdrawal group, turned off transgene 4F2A and therefore the expression of Cyclin D1 was down-regulated (FIG. 3d, e). It was also confirmed that this withdrawal group does not have endogenous expression of the 4 transcription factors (FIG. 9a). Notably, the silencing of the exogenous genes and doxycycline-dependent/controlled cell proliferation allows distinguishing of iPP cells from the typical partially reprogrammed induced pluripotent stem cell cells despite the fact that both fail to express Nanog.

Genetic expression of epithelial gene EpCAM was well maintained after doxycycline withdrawal and was further up-regulated after 4~5 weeks of induction, possibly indicating a phenotypic change of cells under induction (FIG. 3f). Note that similar results were obtained with E-cadherin (FIG. 9b). Importantly, CCSP gene expression, sufficiently suppressed after 3 weeks of induction, is present at robust levels upon withdrawal of factors (FIG. 3g). CCSP, as one of the most important somatic markers of Clara cells, showed a "returning" expression pattern in 3-week withdrawal group at both protein and gene levels. This finding greatly supported the iPP concept that an optimized transient induction allows induced cells return to their original Clara cell phenotype. Moreover, there is an up-regulation of Foxj1 expression further highlighting the differentiation potential of induced Clara cells to ciliated cells (FIG. 9b).

iPP Cells are Able to Generate Functional CFTR Expressing Ciliated Epithelium

Figure 5:
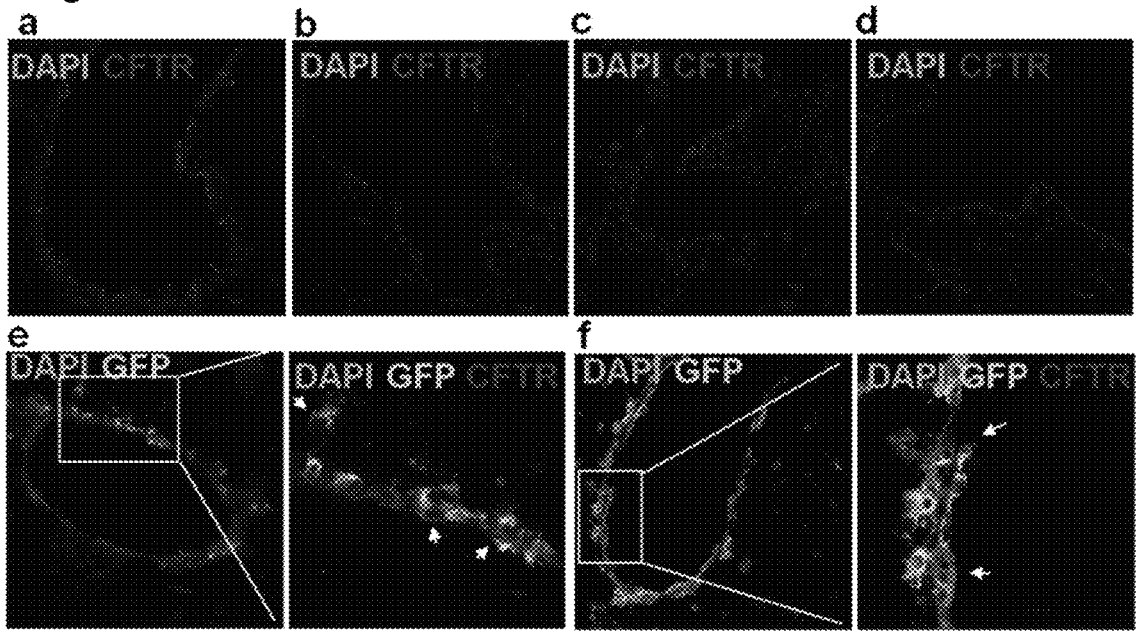
FIG. 5 EpCAM$^{high}$-derived iPP cells can repopulate injured CFTR-knockout epithelium in vivo. Confocal microscopy images of (a) native B57/L6 airway control, (b) native CFTR-KO airway epithelium, injured airway epithelium of CFTR-KO mice at (c) 1 week and (d) 3 weeks post naphthalene treatment showing nuclear stain DAPI and CFTR. Confocal microscopy images of iPP cell-treated injured airway sections, (e) 7 days and (f) 21 days post cell delivery, showing nuclear stain DAPI and CFTR. Scale bar, 10 μm (a-d). (g) Western blot showing the presence of CFTR protein band appearing at approximately 170 kDa representative of the complex glycosylated functional form of CFTR in homogenized lung tissue from iPP cell-treated CFTR-knockout injured mice. (h) Expression of genomic CFTR, as measured by qRT-PCR comparing fold-difference in gene expression at day 7 and day 21 (relative to CFTR wild-type animals). (i) cDNA expression levels of CCSP, FoxJ1 and CFTR, as measured by qRT-PCR comparing fold-differences in expression in wildtype lungs.
Figure 5:
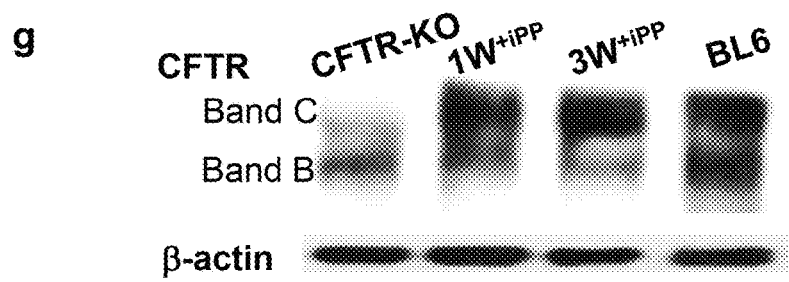
Figure 5:
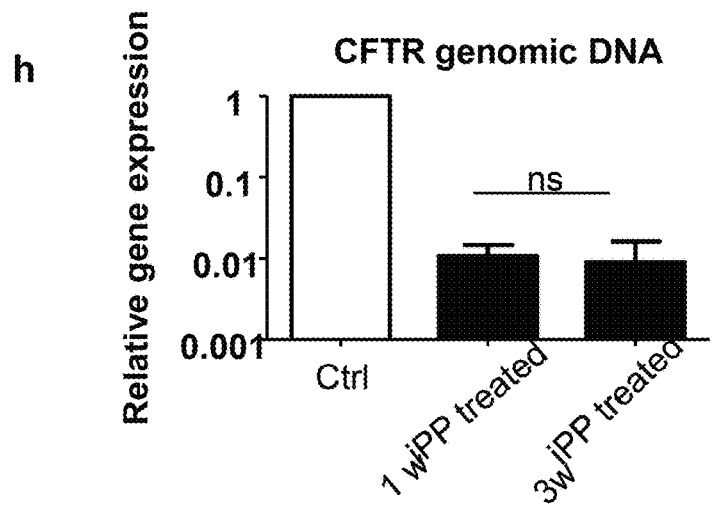
Figure 5:
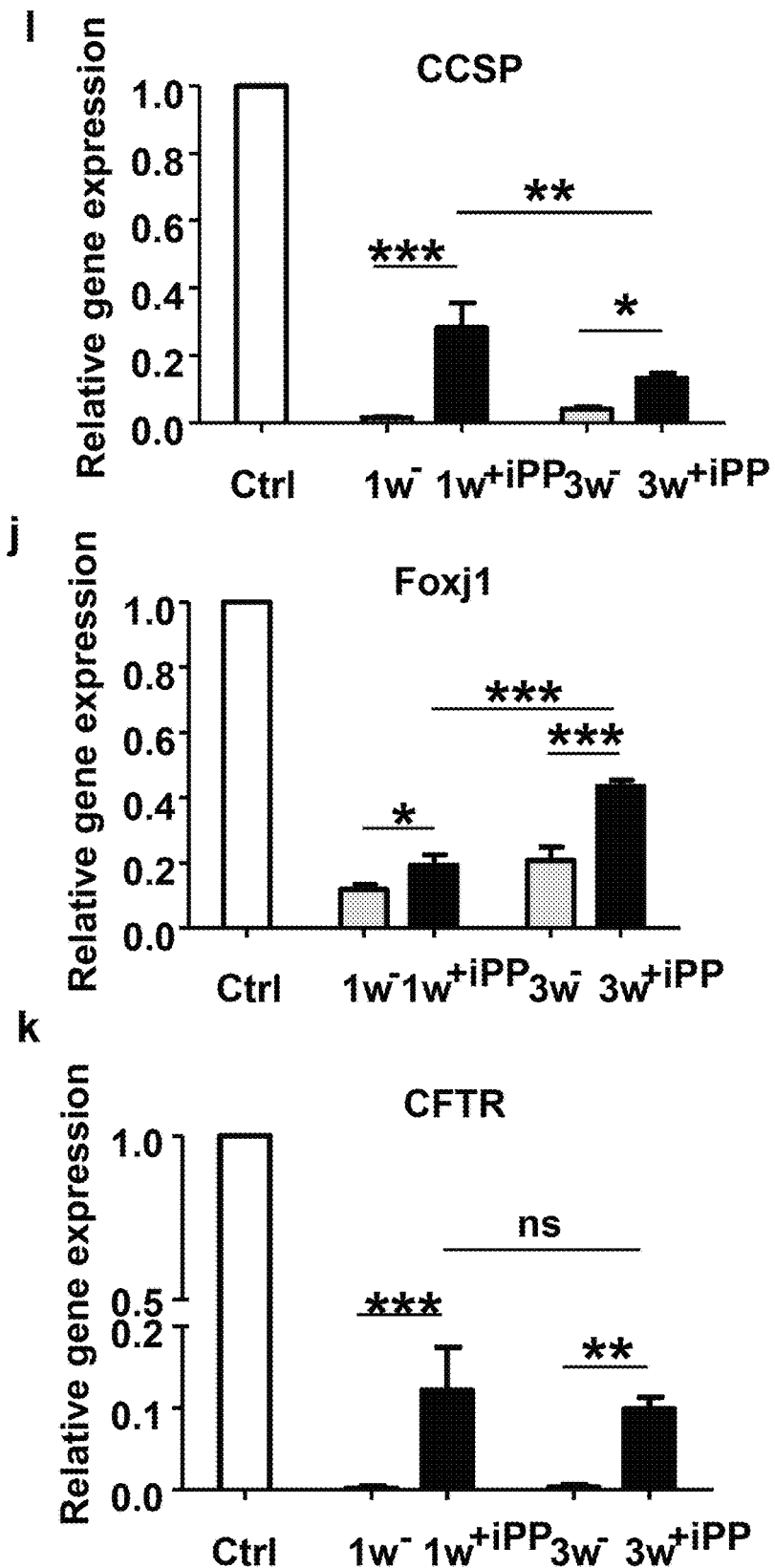
Figure 10:
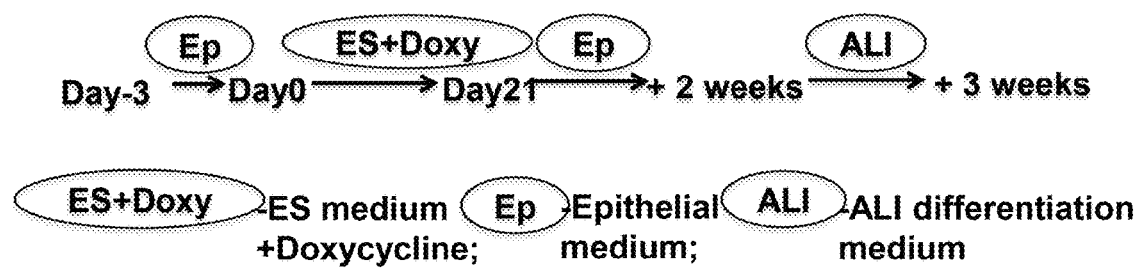
FIG. 10 Schematic graph showing the timeline and optimization conditions used to generate ciliated cells.

In support of the hypothesis that transient induced cells are able to return to their original phenotype, it was shown that EpCAM high-derived iPP cells were able to return to their original Clara cell phenotype with near homogeneity, upon a 2-week withdrawal of inductive factors (FIG. 5a). In order to further elucidate the "homogeneity" of iPP cells to native Clara cells, the differentiation potential of iPP cells in a novel ALI system was examined. Briefly, induced Clara cells generated using a 3-week induction following a 2-week withdrawal, were differentiated in a modified ALI system for 3 weeks (FIG. 10). ALI-conditioned cells were stained with β-tubulin IV for cilia formation showing positivity for the majority of the cells (FIG. 5b). Notably, it was found that ciliogenesis occurred with greater efficiency in the modified Matrigel™-based ALI system compared to the traditional ALI system. To assess the functionality of the induced ciliated epithelium, CFTR expression at both protein and gene levels using immunostaining, flow cytometry and real-time qPCR was examined. It was found that at least 60% of E-cadherin-positive cells expressed CFTR, indicating the formation of functional ciliated epithelium with tight junctions (FIG. 4c). X-Z projections of horizontal optical sections confirmed the apical membrane localization of CFTR while E-cadherin staining was visualized at the lateral membranes (FIG. 4d). Flow cytometric analysis of day 0 fresh isolated EpCAMhigh cells and ALI-conditioned iPP cells revealed the successful generation of CFTR-expressing cells from day 0 cells of low CFTR immunoreactivity (FIG. 4e). Gene expression analysis of ALI-conditioned cells compared to pre-ALI cells (3-week induction+2-week withdrawal cells) showed a reduction of CCSP expression (FIG. 4g) but a marked up-regulation of Foxj1 and CFTR (FIG.

4g), suggesting the likely differentiation of induced Clara cells (pre-ALI) to CFTR-expressing ciliated cells (ALI).

Together, these results show the optimized transient induction can not only achieve expansion of Clara cells, but also preserve the differentiation potential of parental Clara cells to generate functional CFTR-expressing ciliated cells.

Example 2

Methods for In Vivo Engraftment Assay

GFP-iPP cells were transtracheally delivered to naphthalene-treated CFTR-knockout mice lungs to test their ability to engraft and repair CFTR-deficient epithelium. Lung tissues were harvested at 7 and 21 days post cell delivery for further evaluation. The visualization and differentiation of engrafted cells were accessed by dual-label immunohistochemistry staining of anti-GFP and anti-CFTR. CFTR expression in airways of wildtype mice and injured CFTR-knockout mice served as positive and negative controls, respectively. Cell engraftment (cell retention rate) was quantified by qRT-PCR measuring genomic expression of wildtype CFTR.

EpCAM$^{high}$-Derived iPP Cells are Able to Repopulate Injured CFTR-Knockout Epithelium In Vivo.

Herein, the ability of iPP cells to engraft and restore CFTR expression in naphthalene-treated CFTR-knockout mice was tested in vivo. iPP cells derived from male GFP-Col1a14F2A mice were delivered transtracheally to female CFTR-KO animals 2 days post naphthalene injury. Lung tissues were collected 7 days after cell delivery. CFTR expression of engrafted GFP-iPP cells was assessed by immunohistochemistry staining for GFP and CFTR antigens. CFTR expression of native B57/L6 airways was used as positive control. CFTR expression of native CFTR-knockout and naphthalene-treated airways were served as negative controls.

Immunohistochemistry analysis of native B57/L6 mice showed an abandant CFTR expression in airways (FIG. 5a). CFTR-knockout mice lungs without injury showed a significant decrease in the expression of CFTR protein (FIG. 5b), a mark of CFTR disfunction in these transgenic mice. Naphthalene injury resulted in further reduction of CFTR expression in these mice (FIG. 5c). Importantly, in GFP-iPP cell-treated CFTR-knockout lungs, a large number of GFP cells was found which indicates significant cell engraftment at day 7 post cell delivery. Moreover, a number of GFP cells started expressing CFTR (FIG. 5d). iPP cells may be used to repair injured CFTR dysfunctional airways.

Engraftment and CFTR expression data at day 21 will be obtained. Cell engraftment will be quantified using SRY (Sex-determining Region Y) analysis using male-specific amplifying primers or quantified by qRT-PCR measuring genomic expression of wildtype CFTR. Genomic DNA from female mice will be used as negative controls. Western blot measuring CFTR protein restoration in iPP-repopulated lung will be performed.

Results for a first group (n=3) have been obtained and are described below.

Transient Induction Allows Preservation of Lineage Preference and Commitment

Figure 6:
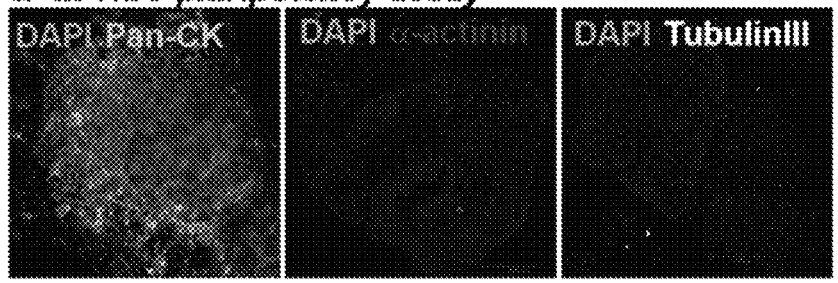
FIG. 6 Transient induction allows preservation of lineage preference and commitment. Confocal microscopy images of (a) 3-week induced iPP cells following in vitro culture under teratoma formation conditions. Images show staining for nuclear stain DAPI, Pan-CK, anti-α-actinin, and tubulin III. (b) Cells induced for >8 weeks under in vitro teratoma assay conditions with (b) Pan-CK, (c) anti-α-actinin, and (d) Nanog respectively. Confocal microscopy images of >8 week induced cells under (e) neuron cell differentiation assay conditions showing tubulin III staining and (f) under ALI ciliated cell differentiation conditions showing β-tubulin IV staining. Scale bar, 10 μm.
Figure 6:
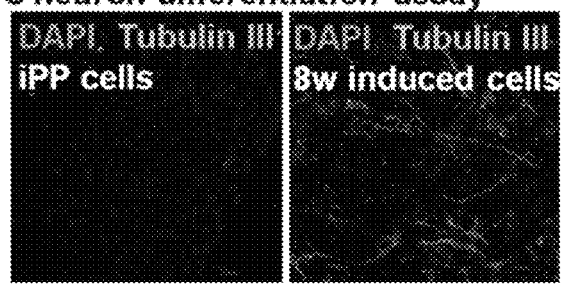
Figure 6:
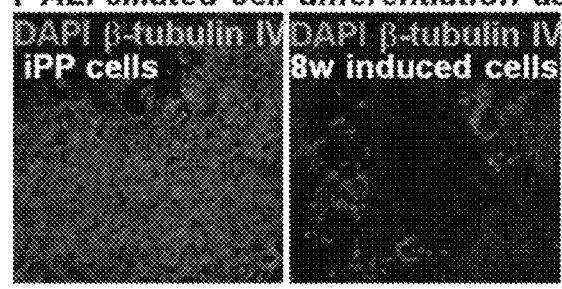

To elucidate the cell lineage preference of iPP cells, an in vitro teratoma assay (Shulamit Levenberg et al., 2003) was used to compare the differentiation potential of 3-week induced iPP cells to those induced for a prolonged duration (>8 weeks). Lineage differentiation was accessed by immunostaining for Pan-CK (endoderm epithelial cell marker), α-actinin (mesoderm cardiomyocyte marker) and β-tubulin III (ectoderm neuron cell marker) and demonstrated that 3-week induced iPP cells committed only to an epithelial lineage (presence of Pan-CK-expressing cells) (FIG. 6a). On the contrary, over 8 week-induced cells, in addition to showing Pan-CK expression, were able to generate α-actinin$^+$ cells, with the typical periodicity in the Z line of cardiac myofibrils (FIG. 6b, c). Nanog-positive undifferentiated cells were also observed (FIG. 6d). The existence of mixed populations of differentiated cells and undifferentiated cells in the 2-3 months induced cell group indicated a multi-lineage differentiation potential, similar to pluripotent cells. Taken together, optimized transient induction preserve lineage preference that iPP cells exhibited a significant tendency for differentiation to epithelial cells.

Neuron-specific differentiation comparing iPP cells and >8-week induced cells revealed a lack of β-tubulin III (a specific marker of neuron cells) in iPP cell group (FIG. 6e). In contrast, β-tubulin III expressing cells were found in >8-week induced cell group suggesting prolonged induction results in divergence from the original lineage and a greater capacity for pluripotency (FIG. 6e). The disclosed iPP cell generation approach, allows for regulated-transient induction and preservation of epithelial lineage preference and commitment.

In support of commitment to lineage of memory, the ability of the optimal 3-week induced iPP cells to produce ciliated cells was also tested. 3-week induced iPP cells and >8-week induced cells were cultured under ALI conditions for 3 weeks then characterized by immunostaining of β-tubulin IV. Immunostaining analysis showed 3-week induction derived iPP cells exhibited a higher tendency for generation of ciliated cells (β-tubulin 66.7%±7.64% cells) (FIG. 6f) compared to 2-3 months induced cells (β-tubulin 25%±5% cells) (FIG. 6f). This result highlights that the optimized transient induction used to generate iPPs allows reservation of memory of parental Clara cells from which they originate and thereby favor lineage differentiation potential.

Example 3

Figure 13:
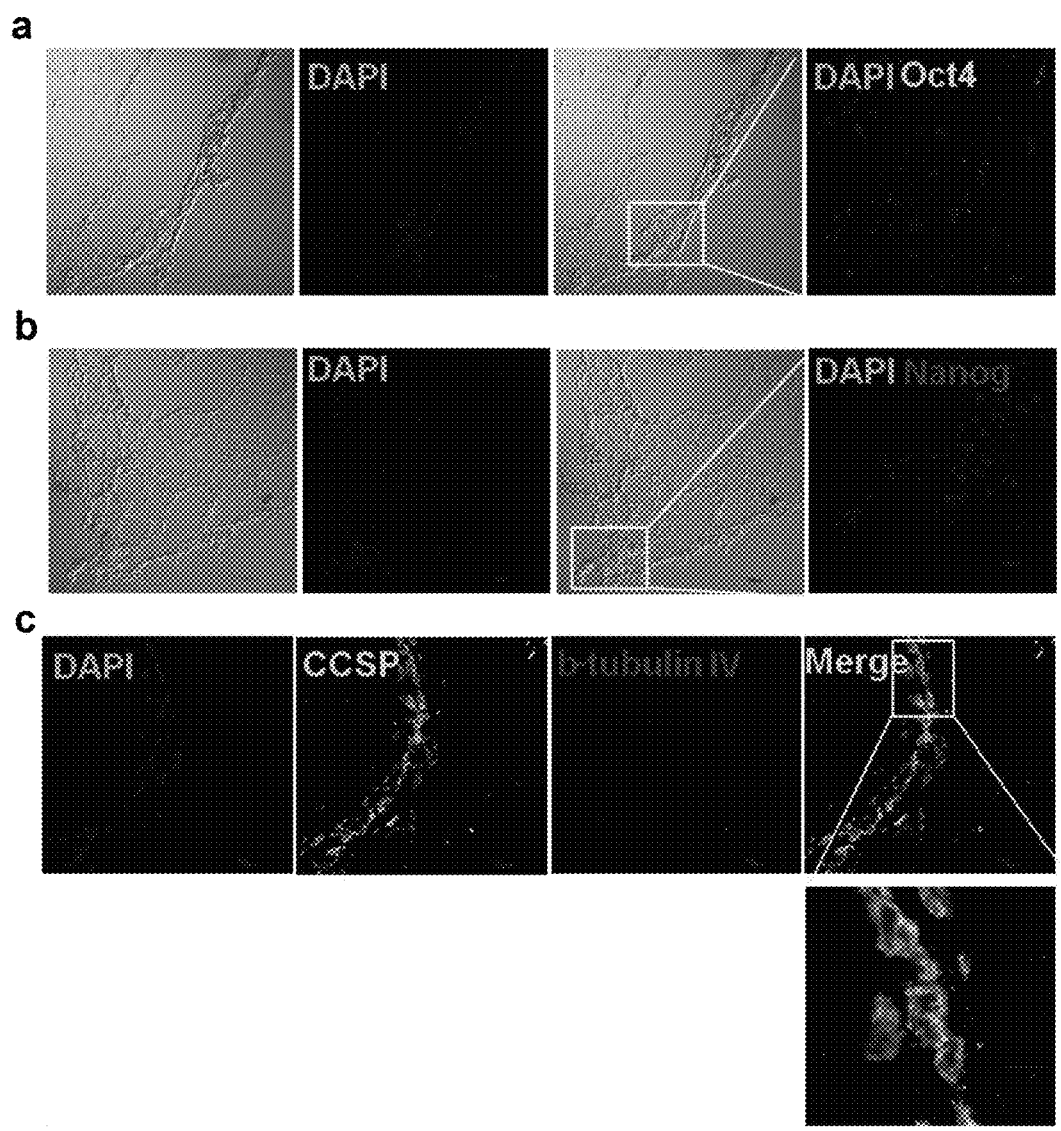
FIG. 13. Microscopy images of recellularized and decellularized lung. Whole cultures were incubated at 37° C. in a humidified incubator and re-fed every 3 days. After 9 days, lungs were harvested and frozen sectioned for immunohistochemistry analysis. The activation of the transgenes and pluripotency of the engrafted cells were accessed by immunohistochemistry staining of DAPI, Oct4 (Panel A) and Nanog (Panel B), respectively. The differentiation of iPP cells was assessed by dual-label staining of different epithelial lineage markers (AQP5,CCSP,SPC,β-tubulin) and only showing CCSP immuno-reactivity (Panel C).

Ex Vivo the Engraftment and Differentiation of EpCAM$^{high}$-Derived iPP Cells in Mouse Lung Scaffold An ex vivo study using decellularized mouse lung scaffold to determine the engraftment and differentiation of EpCAM$^{high}$-derived iPP cells was performed. Briefly, EpCAM$^{high}$-derived iPP cells were suspended in epithelial medium and trans-tracheally delivered to the one decellularized lobe of mouse lungs while the other lobes were ligated and used as negative controls. Whole cultures were incubated at 37° C. in a humidified incubator and re-fed every 3 days. After 9 days, lungs were harvested and frozen sectioned for immunohistochemistry analysis. DAPI staining showed the injected cells were able to survive and engraft in lung scaffold culturing for 9 days. Interestingly, almost all the engrafted cells were found at the bronchiolar airways where the parental Clara cells were located (FIG. 13A). It is known that cell-cell contact, cell-matrix interaction and stem cell niche are involved in cell engraftment, differentiation and therefore injury repair. Whether there is a preference of where iPP cells engrafted or just a matter of culturing period is still under determined. Negative staining of both Oct4 and Nanog showed the silencing of transgenes and non-pluripotency, respectively (FIG. 13A-B).

The differentiation of iPP cells was assessed by dual-label immunohistochemistry staining of different epithelial lineage markers (AQP5,CCSP,SPC,β-tubulin). Immunohistochemistry result showed some engrafted cells were able to re-gain CCSP expression culturing in lung scaffold (FIG. 13C). This result is consistent with previous in vitro study that the epigenetic fingerprint of iPP cells enables them to return to the original Clara cell phenotype upon withdrawal of the inductive factors. However, no β-tubulin IV-positive cells were detected suggesting some other factors which mimic in vivo development may be required for differentiation of Clara cell to ciliated cell in ex vivo (e.g. bioreactor). In addition, neither AQP5-positive nor SPC-positive cells were found.

This ex vivo study highlighted the great ability of iPP cells to engraft and differentiate, and thereby to repair injury which will be further determined in animal injury model in vivo.

Example 4

Minimal research has been performed investigating the involvement of induced pluripotent stem cell technology on the repair of lung injuries. Thus, there is great hope that induced pluripotent stem cells, which in many ways are equivalent to the controversial embryonic stem (ES) cell, could be a potential source for replacement of damaged pulmonary epithelium. The present results indicate that functional lung cells can be derived from induced populations of cells.

Reprogramming of EpCAM$^{high}$-Clara Cells Derived from Oct4-eGFP Chimera Lungs The iPP concept was proven using Col1a1-4F2A transgenic mice. In order to further determine whether this concept can be applied to other reprogrammable cells with different constructs, EpCAM$^{high}$-Clara cells derived from Oct4-eGFP chimera mice lungs were isolated and reprogrammed. The Oct4-eGFP chimera mice are derived from PiggyBac7/Oct4-eGFP iPSC. Mouse Oct4-GFP construct was inserted into R1 mouse ES cells to generate Oct4-GFP mouse. MEFs were isolated from E12.5 embryo, expanded for at least two passages then transfected with PB-TET-MKOS and rtTA using the neo system. Doxycycline was added 48 h after transfection. Stable GFP-iPS cells thus generated express characteristic pluripotency markers after doxycycline addition. This iPS cell line was able to generate teratoma and chimeric animals. The Oct4-eGFP chimeric mouse allows the endogenous Oct4 expression to be easily monitored by GFP expression.

Figure 12:
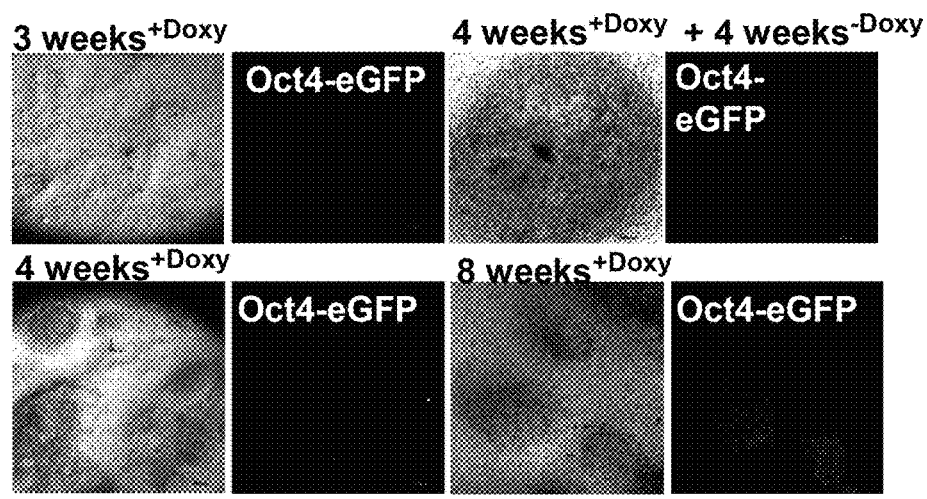
FIG. 12. Reprogramming of EpCAM$^{high}$-Clara cells derived from Oct4-eGFP chimera lungs (a) Morphological changes of induced colonies at different time points. A few induced colonies started expressing eGFP at 7~8 weeks of induction. (b) ES-like colonies expressed endogenous Oct4, Nanog and SSEA-1. Eight week-induced cells are not only able to express endogenous Oct4, but also the important pluripotency marker-Nanog indicating the great potential to generate true induced pluripotent stem cells (top). Eight week-induced cells are able to express eGFP suggesting the activation of endogenous Oct4. Pan-CK expressing cells are non-GFP cells, which further confirmed previous finding Pan-CK could serve as a sufficient marker to identify epithelial cells from induced pluripotent stem cell-like cells (bottom). (c) EpCAM$^{high}$ Clara cells were induced for 4 weeks followed by another 4 weeks in epithelial medium showing approximately 30-40% of the Pan-CK positive wells were positive for CCSP. Scale bar, 10 μm.
Figure 12:
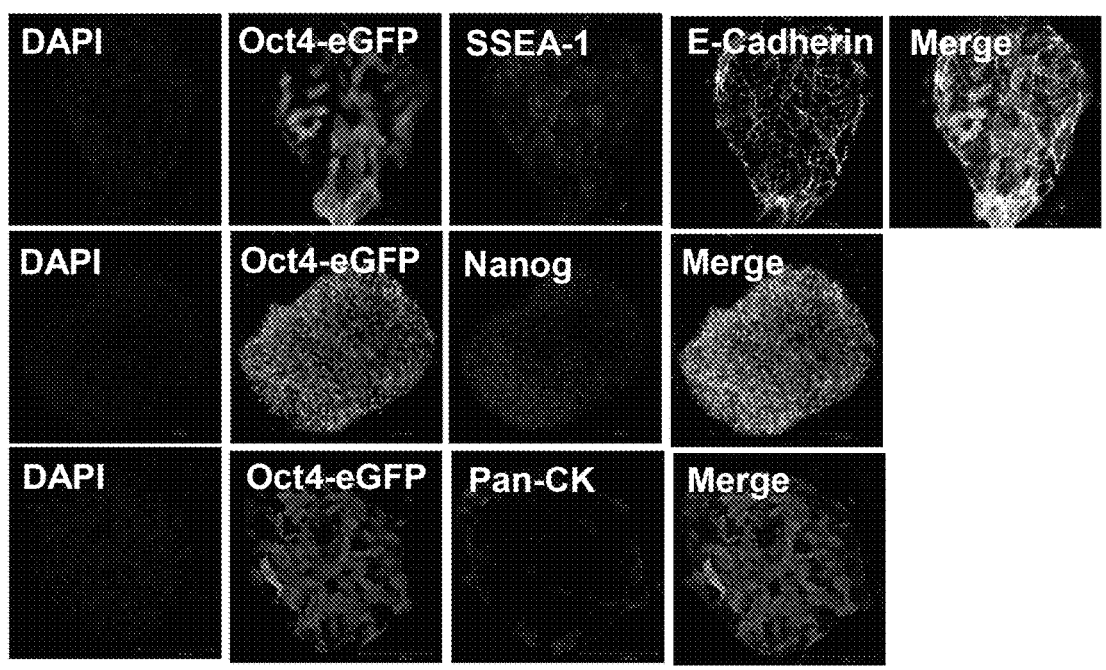
Figure 12:
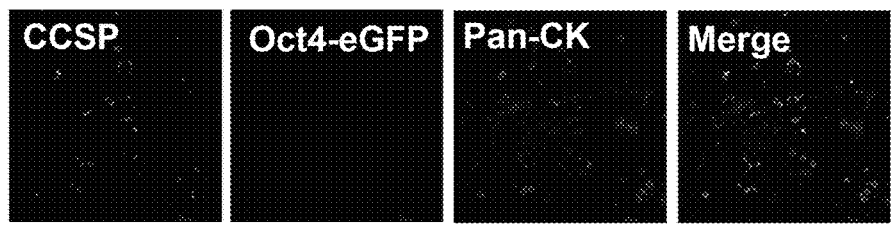

In a 2D reprogramming condition, a few colonies started expressing eGFP after 7-8 weeks of induction indicating the activation of endogenous Oct4 expression (FIG. 12. A). Furthermore, these colonies were characterized by immunostaining of pluripotency markers (Nanog and SSEA-1) and exhibited a characteristic of iPS-like expressing all these markers (FIG. 12.B). In addition, it was found that Pan-CK$^+$ cells are non-GFP cells that further confirmed a previous finding that Pan-CK serves as a sufficient marker to identify epithelial cells in the induced pluripotent stem cell reprogramming process. When EpCAM$^{high}$ Clara cells were induced for 4 weeks followed by another 4 weeks culturing in epithelial medium, 30-40% of pan-CK-positive cells were able to express CCSP showing the "returning" of the induced cells to their original Clara cell phenotype upon withdrawal of the inducing factors (FIG. 12.C).

Matrigel™

Example 5

Expansion of Patient-Specific Cystic Fibrosis (CF) Epithelial Cells for Drug Screening Through Transient Partial Reprogramming The expansion and scale-up of patient-specific CF epithelial cells for use in drug screening through transient partial reprogramming will be undertaken. Epithelial cells will be isolated from patient. Patient-specific CFTR expressing ciliated cells will be generated using the herein described iPP induction method. These can be used for drug screening and for the development of patient-specific drugs.

Specifically, cells will be expanded using the iPP method and differentiated into ciliated cells. This process involves (1) isolating and purifying airway epithelial cells from CF human lung tissue samples; (2) transiently reprogramming cells into a progenitor cell state which can be expanded under tightly regulated conditions; and (3) differentiating the expanded epithelial population into mature airway cells to be used for drug screening applications.

Ciliated cells will be identified by positive staining for ciliated cell specific marker β-tubulin IV. It will be tested whether differentiated cells can form tight monolayers in 24 well plates and be utilized in Ussing chambers (used to measure chloride transport across epithelial membranes). This will be used to test the functionality of CFTR. This newly developed technology will not only allow for drug screening in CF, but may be applicable to a wide range of other cells and tissues.

Example 6

Isolation of Basal-Progenitor Populations from Mouse Tracheal Epithelial Cells

Figure 14:
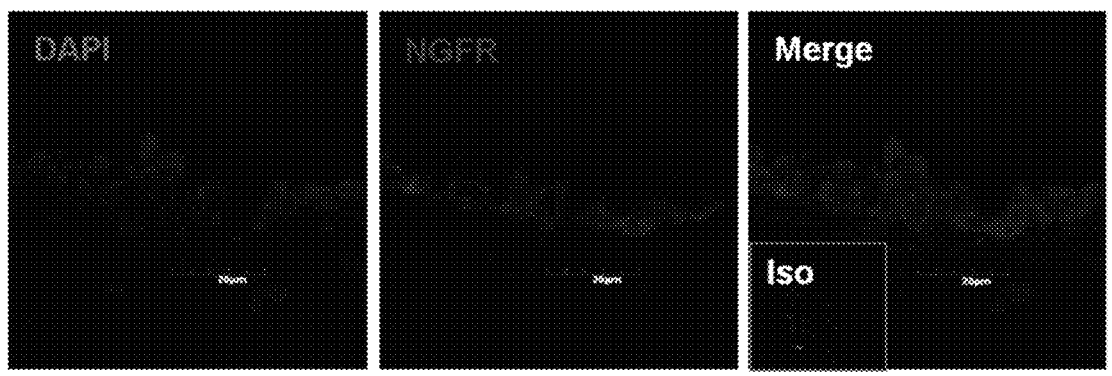
FIG. 14. Panel (a) shows NGFR expression of mouse trachea frozen section and panel (b) shows flow cytometric isolation of NGFR-expressing cells from mouse trachea. Antibody titration was optimized for flow cytometry therefore allowing cell sorting based on NGFR expression.
Figure 14:
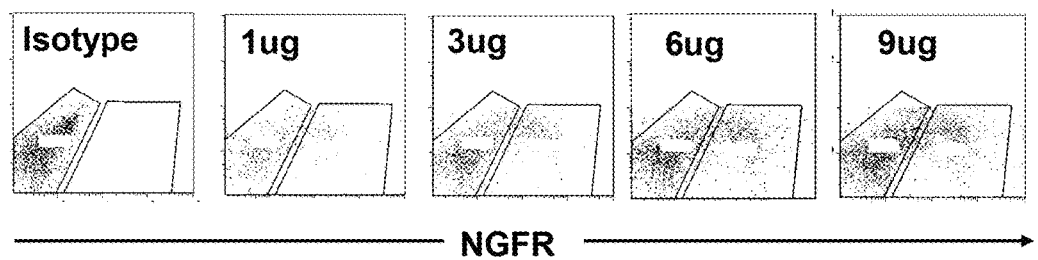

As previous publications have described, NGFR is a member of the TNF receptor super family, and is enriched in tracheal basal cells [4]. Basal-progenitor cells in the mouse trachea could be sorted using flow cytometry based on their NGFR expression. First, NGFR expression was detected in the mouse trachea of frozen sections by immunohistochemistry (FIG. 14.A). Antibody titration was optimized for flow cytometry therefore allowing cell sorting based on NGFR expression (FIG. 14.B).

Figure 15:
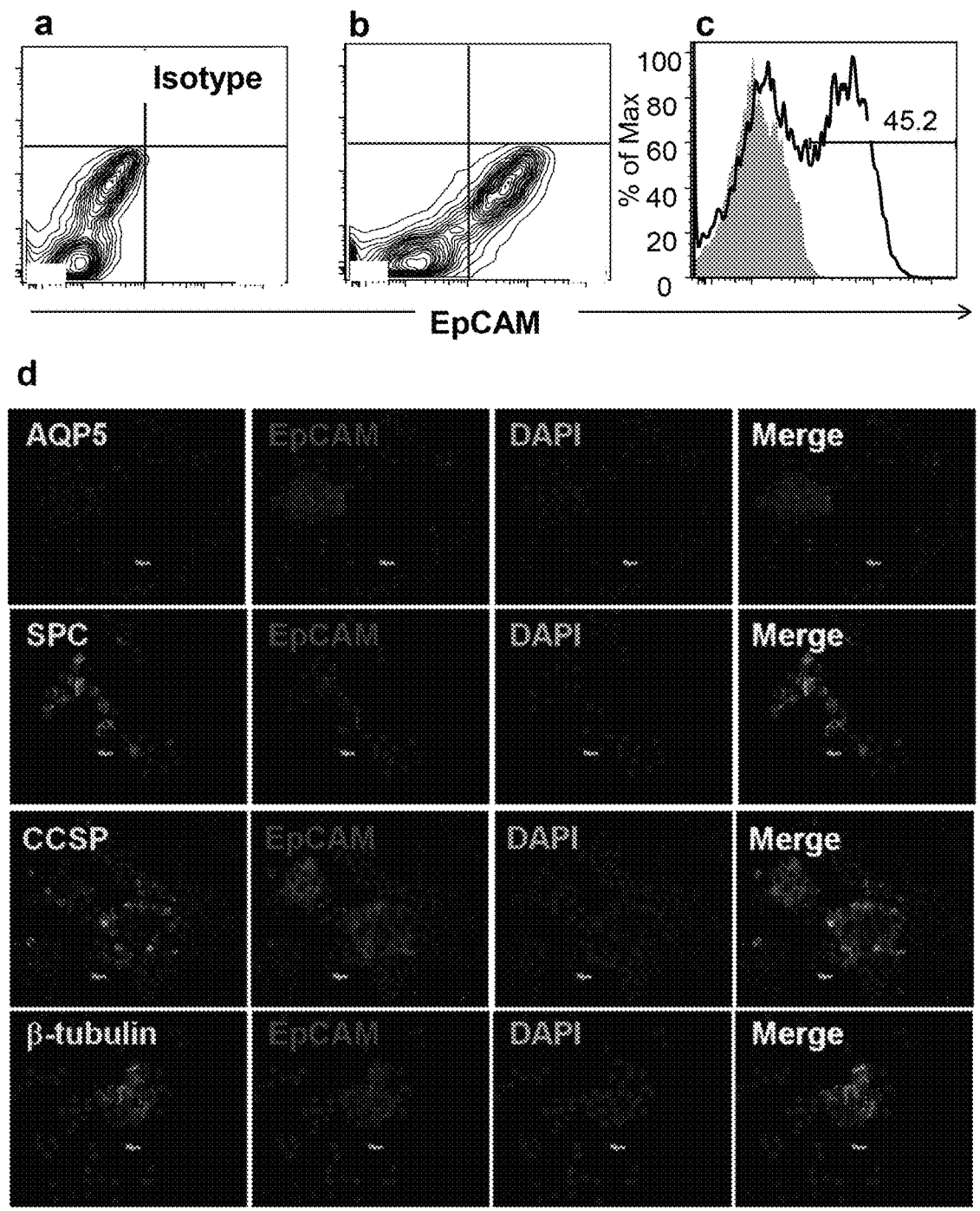
FIG. 15. Isolation and characterization of total lung epithelial cells. Total lung epithelial cells (EpCAM$^{pos}$ CD45$^{neg}$ CD31$^{neg}$), sorted by FACs (Panels A-C). Dual-label immunohistochemistry staining of different epithelial lineage markers AQP5, SPC CCSP, and β-tubulin of the isolated EpCAM$^{pos}$ CD45$^{neg}$ CD31$^{neg}$ cells (Panel D from top to bottom).
Figure 16:
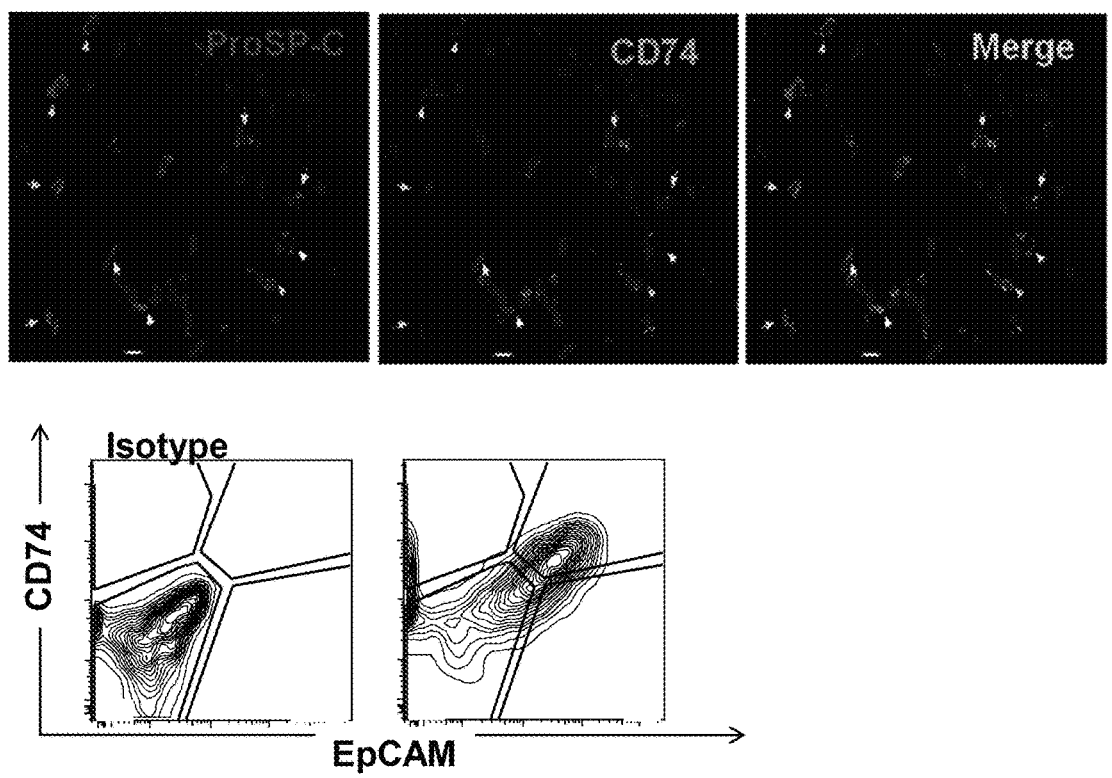
FIG. 16. (a) CD74 expression of frozen mouse lung section and (b) AT-II cell isolation using CD74 AND EpCAM.

Isolation and Characterization of Lung Total Epithelial Cells:

In order to obtain total epithelial cells from mouse lung, cells were isolated and further purified by FACS. Briefly, CD45 and CD31 were used to sort non-hematopoietic (CD45$^{neg}$) and non-endothelial cells (CD31$^{neg}$) then sorted a pure epithelial population according to EpCAM expression. Total lung epithelial cells (EpCAM$^{pos}$ CD45$^{neg}$ CD31$^{neg}$), which make-up 40-50% of CD45$^{neg}$ CD31$^{neg}$ cells, can be sorted by FACs (FIG. 15, A-C). The EpCAM$^{pos}$ cell population is a mixture of AT-II, ciliated cells and Clara cells. AQP5+ cells, as a marker of Type I cells, were not detectable (FIG. 15.D).

a Novel Isolation Method for Lung Alveolar Type II Cells:

Leigh M. Marsh, et al. (2010) [3] reported that the expression of CD74 in mouse lung sections was predominantly localized to AEC-II and alveolar macrophages and no expression was detected in the bronchial epithelium. The inventors performed immunohistochemical staining of frozen mouse lung tissue sections with anti-CD74 and the classical AEC-II marker anti-proSP-C, and confirmed that the AEC-II cells expressed high surface levels of CD74 [3] (FIG. 16.A). In order to obtain high purity ATII cells, a FACS strategy using CD74 as an additional surface marker to further purify ATII cell population was developed. Based on the AT-II-specific isolation protocol[2] (indicated in Method), AT-II cells (approximately 35% of CD45/CD31 neg cells) could be FACs sorted using the EpCAM and CD74 antibodies (FIG. 16.B).

To isolate AT-II cells, lungs are filled with 0.25% trypsin and 10 units per ml of porcine elastase for 15 mins. The lung are then be minced and cells collected by centrifugation. The cell pellet are resuspended in DMEM:F12 without serum and cells plated on collagen-coated dishes for 30 mins. The non-adherent cells are collected and sorted by FACS to isolate the $CD74^{pos}EpCAM^{pos}$ AT-II cells.

The methods established for the generation of $EpCAM^{high}$ Clara-cell iPP cells, as described in Example 1, are applied to obtain AEC-II iPP cells. Transient reprogramming is accomplished though activation of transgenes by doxycycline (directly added to culture media). As previously described, the optimal duration for doxycycline treatment resulting in $EpCAM^{high}$ iPP cells, was determined to be 3 weeks. A time course of doxycycline treatment evaluating the clonal proliferation ability of the AEC-II iPP cells is performed weekly for 6 weeks to determine the exact time point before which the cells show factor independent proliferation. In order to evaluate the AEC-II cell partial reprogramming process, RNA is isolated at various time points of the reprogramming process for quantification of gene expression by qRT-PCR under the optimized culture conditions. Four groups of genes will be detected: 1) the reprogramming factors, MKOS, including their transgene expression and endogenous expression, 2) Pluripotency related genes including the maturation phase group of genes (Oct4, Nanog and Sall4), as well as the stabilization phase group (Dnmt3I, Lin28, Utf1, PECAM, Stella and Dppa4), 3) Epithelial-lineage genes and epithelial-associated genes, and 4) Epithelial progenitor-related genes.

Detailed Methodology:

Isolated AEC-II cells from ROSA26-rtTA and Col1a1: tetO-4F2A double transgenic mice, are induced using the Matrigel™-based iPP assay described in Example 1. Mitomycin treated in-activated mouse embryonic fibroblasts (MEF) are seeded on 0.1% gelatin coated 24-well Transwell® filter inserts (Corning) one day prior to the addition of AEC-II cells. FAC sorted AEC-II cells resuspended in 100 µL of Matrigel™ (BD Biosciences) prediluted 1:1 (vol/vol) with epithelial-specific (Epi-S) media are then added to MEF-coated 24-well Transwell® filter inserts in a 24-well tissue culture plate containing 500 µL of media for 3-5 days then replaced with ES medium containing 1.5 µg/ml Doxycycline (Sigma). ES medium comprised of DMEM/F12 (Invitrogen) supplemented with 10% FBS, penicillin/streptomycin, 10 mg/ml insulin, 5 mg/ml transferring-selenium (Sigma), epidermal growth factor (EGF, 20 ng/mL; Sigma), fibroblast growth factor-10 (FGF-10, 50 ng/mL; R&D Systems) and hepatocyte growth factor (HGF, 30 ng/mL; R&D Systems). Media is replenished three times per week. For bulk passaging and sample analysis, whole cultures will be dissociated in Collagenase (1 mg/ml; Sigma)/Dispase (3 mg/ml; BD Biosciences) in PBS to generate single-cell suspensions. For clonal passaging, single colonies will be picked and dissociated in the Collagenase/Dispase solution.

Example 7

Generation of IPP Cells from Human Lung Tissue

Clara cells are isolated from human lung tissue on the basis of CD31, CD45, and EpCAM expression. Specifically, $EpCAM^{HIGH}$-Clara cells are isolated using methods described for isolation Clara cells from mouse lung in Example 1.

Transfection of both human lung epithelial cell lines (Beas2b/NHBE) as well as isolated human primary epithelial cells is done using a doxycycline-inducible lentivirus system (Stemgent® Dox Lentivirus Set: h4F2A human containing a single polycistronic lentivirus encoding the 4 factors; OR Stemgent® Dox-Inducible Lentivirus Set: Human OKSM containing 4 separate vectors—one for each factor).

Alternative reprogramming construct, such as viral transduction, are also used with human cells.

The cells are reprogrammed to iPS cells and evaluated at specific time points to determine the period of induction before pluripotency is reached. Cells are then evaluated for ability to return to their original phenotype without pluripotency by withdrawing doxycycline at various time points prior to pluripotency.

Example 8

Isolation and Identification of a Naphthalene-Sensitive Clara Cell Population

Properties of the starting cell population, including heterogeneous transgene expression (Wernig M. et al, 2008; Shao L. et al, 2009) and the degree of differentiation across the starting cell population (Eminli S. et al., 2009; Hanna J. et al., 2009) have been shown to influence the iPS reprogramming process. To minimize confounding factors, a highly purified Clara cell population from mouse lung was selected. Using a modified Clara cell isolation protocol (Atkinson J. et al, 2008), $CD45^{neg}CD31^{neg}EpCAM^{pos}$ lung epithelial cells were sorted according to EpCAM expression, which identified two distinct epithelial populations, namely $EpCAM^{high}$ and $EpCAM^{low}$ cells (FIG. 1b). Flow cytometry analysis using Clara cell-specific markers, Clara cell secretory protein (CCSP) (Hackett B P et al, 1992) and Claudin10 (Cldn 10) (Tsao P-N et al., 2009) demonstrated that $EpCAM^{high}$ cells are exclusively Clara cells expressing CCSP (FIG. 1 b), and Cldn 10 (FIG. 7a). The $EpCAM^{low}$ population, although composed largely of Clara cells (~90%) (FIG. 1c), also contained a percentage of pro-SPC (Fehrenbach H, 2001) expressing type II alveolar epithelial cells (AT-II) (FIG. 7b). Both populations were negative for type I alveolar epithelial cell (AT-1) marker, T1a (Williams M et al., 1996) and ciliated cell marker, β-tubulin (Rawlins E et al., 2008) (Supplementary FIG. 1b). Gene expression analyses showed that the $EpCAM^{high}$ population had markedly higher CCSP expression. In contrast, Sftpc expression is significantly higher in the $EpCAM^{low}$ population. Clara cell-related genes Cyp2f2, Cldn10, Aox3, and Pont were detected within both populations with higher levels in the $EpCAM^{high}$ population (FIG. 1d, e). Previous studies have demonstrated that naphthalene results in selective loss of mature Clara cells which are subsequently replaced by naphthalene-resistant progenitors termed variant Clara cells (Stripp B R et al., 1995). In order to evaluate whether $EpCAM^{high}$ and $EpCAM^{low}$ populations contained functionally different subtypes of Clara cells, EpCAM expression in cells isolated from naphthalene-treated and non-treated mice was compared. EpCAM$^{high}$ cells where nearly completed ablated, showing that they are indeed naphthalene-sensitive Clara cells (FIG. 1f).

Transient Induction Enables EpCAM$^{high}$-Clara Cells to Proliferate but Return to Quiescence Upon Withdrawal of Reprogramming Factors EpCAM$^{high}$ cells were derived from ROSA26-rtTA/Col1a1::tetO-4F2A double transgenic mice allowing for doxycycline-inducible iPS reprogramming transgene (Oct4, Sox2, Klf4 and c-Myc) activation. To measure the proliferative response of EpCAM$^{high}$-Clara cells to inductive factors, a previously described culture system allowing for separation of seeded cells from a feeder population was adapted (Kim S et al., 2007) (FIG. 8a). EpCAM$^{high}$ cells were labeled with carboxyfluorescein diacetate, succinimidyl ester (CFSE) (Benharouga M et al., 2003) dye in the presence and absence of doxycycline. Inductive factors induced cell proliferation in EpCAM$^{high}$ cells (FIG. 1g). Withdrawal of reprogramming factors after 1 week arrested their proliferative capacity. In parallel, continuous doxycycline treatment (14 days) resulted in proliferation and loss of EpCAM expression (FIG. 1h). CFSE dilution coincided with significant up-regulation of cyclin D1 in the doxycycline-treated groups (FIG. 1i). Doxycycline withdrawal resulted in almost complete downregulation of the transgene construct 4F2A expression (FIG. 1j). Importantly, EpCAM and CCSP expression re-emerged in the withdrawal group (FIG. 1k, l). Taken together, these results suggest that transiently induced expanded cells mimic the phenotype of the original EpCAM$^{high}$ cells.

Figure 2:
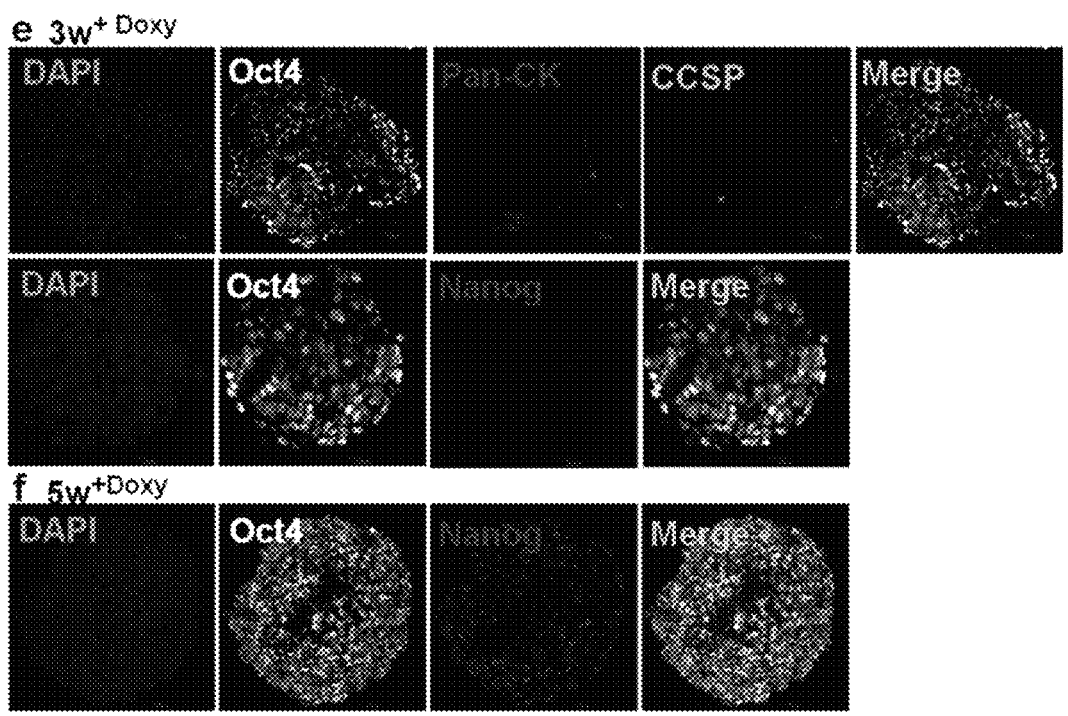
FIG. 2 Transient induction in Matrigel™-based conditions results in clonal expansion of $EpCAM^{high}$-Clara cells. (a) Morphological changes of induced colonies during the 3-week doxycycline treatment. Light microscopy brightfield images showing colony formation at 1 week (1 w), 2 weeks (2 w), and 3 weeks (3 w) in the presence of doxycycline in Matrigel™-based clonogenic 3D conditions. (b) Brightfield (top, left) and confocol microscopy images of doxycycline-treated EpCAM high cells (1 week) stained with nuclear stain DAPI (top-right), and EpCAM (bottom-left). (c) Bulk serial passage of induced colonies during the 3 weeks of induction. Left Y axis represents the folds change in total cell number relative to Day 0 seeded cells (10,000 cells/well). Right Y axis represents the total number of colony forming units (CFU) generated. (d) Second generation colonies (enzymatic digestion and CFU formation of single $1^{st}$ generation colonies) obtained after 3, 4 and 5 weeks of induction with or without doxycycline withdrawal. Quantification of $2^{nd}$ generation CFU incidence at 3, 4 and 5 weeks comparing induced cells in the presence and absence of doxycycline for 7 days. (e) Confocol microscopy images depicting 3-week induced colonies (3 $w^{+Doxy}$) stained with nuclear stain DAPI (top/bottom panel), transcription factor OCT4 (top/bottom panel), epithelial cell marker Pan-CK (top panel), Clara cell marker CCSP (top panel) and Nanog (bottom panel). (f) Immunostaining of 5 week-induced colonies (5 $w^{+Doxy}$) showing Nanog immunereactivity. For c and d, values are mean±S.D. of triplicate samples. Scale bar, 10 µm (a, b, e and f).

Transient Induction in Matrigel™ Results in Efficient Clonal Expansion of EpCAM$^{high}$-Clara Cells To optimize expansion during the iPP induction process, a Matrigel™-based clonogenic 3D system was modified (McQualter J et al., 2010). Isolated EpCAM$^{high}$ cells were suspended in Matrigel™ and seeded on inactivated MEF feeders and treated with or without doxycycline. During doxycycline treatment, EpCAM$^{high}$ cells exhibited clonogenic growth (FIG. 2a) showing airway-like epithelial colonies with hollow lumens (FIG. 2b). No colonies were generated in the absence of doxycycline (FIG. 2a) demonstrating that native EpCAM$^{high}$ cells lack clonogenic ability in Matrigel™ alone. Serial passaging in the presence of doxycycline showed that a subset of induced colonies retained colony-forming potential (FIG. 2 c, right Y axis). Importantly, there was a progressive increase in total cell number (~30-fold expansion) after a 3-week induction (FIG. 2c, left Y axis). Single colonies, passaged after 3, 4 and 5 weeks of induction, and cultured in the presence and absence of doxycycline showed that doxycycline-treated cells possessed greater colony-forming potential and 5-week induced cells treated with doxycycline had the highest CFU count among all the groups. Even after three weeks of exposure to doxycycline, clonogenic capacity remained dependent on continued expression of inductive factors (FIG. 2d). In contrast, some 4-week and 5-week induced colonies retained their clonal proliferation ability when doxycycline was withdrawn, suggesting attainment of a factor-independent stage in the reprogramming process; indicative of a important change somewhere between 3 and 5 weeks of induction.

To determine the optimal time window for doxycycline withdrawal, induced colonies were characterized using immunofluorescence for Oct4 (a measure of transgene activation), Nanog (suggestive of pluripotency, but not one of the transgenes), Pan-CK (showing epithelial phenotype) and CCSP (showing Clara cell phenotype). Three weeks of doxycycline treatment resulted in successful activation of the transgenes and suppression of lung markers-Pan-CK and CCSP. Negative staining was seen for Nanog, confirmed that the cells had not yet gained transgene-independent pluripotency (FIG. 2e). An additional 2 weeks of doxycycline treatment (5-week induction) resulted in 20-30% Nanog-positive colonies (FIG. 2f). Thus, the time window for iPP creation was framed at sometime between 3 but less than 5 weeks of induction, at which time the greatest level of expansion was achieved without gaining pluripotency.

Transient Induction Allows EpCAMhigh-Derived Colonies to Return to their Original Clara Cell-Phenotype Upon Withdrawal of Factors The ability of EpCAM$^{high}$-derived transiently induced colonies to return to their original phenotype following doxycycline withdrawal was assessed. Colonies obtained at different time points were characterized by immunostaining for Nanog, Pan-CK and CCSP expression. Three-week induced colonies showed over 90% of cells expressed Pan-CK. Approximately 80% of the Pan-CK+ cells expressed CCSP after doxycycline withdrawal and a further 2 weeks of culture in epithelial media (FIG. 3a). Notably, 3-week induced cells did not express Nanog. Withdrawal of doxycycline, one week later, at 4 weeks, colonies were still predominantly Nanog-Pan-CK+ colonies (FIG. 3b) but also a few Nanog+ colonies (FIG. 3c). Doxycycline treatment results in up-regulation of transgene 4F2A and Cyclin D1 with greater expression in the 5-week induced group. Three-week induction followed by 2 weeks of doxycycline withdrawal, turned off transgene 4F2A and down-regulated expression of Cyclin D1 (FIG. 3d, e). Also, the fact that the withdrawal group does not have endogenous expression of the 4 transcription factors was confirmed (FIG. 9a). Induced pluripotent progenitors differ from partially reprogrammed iPS cells in that the latter express the inductive transcription factors and show factor-independent proliferation (Yin L et al., 2012). Expression levels of EpCAM (FIG. 3f) and E-cadherin (FIG. 9b) were well maintained after doxycycline withdrawal but were further upregulated after 4-5 weeks of induction. Importantly, CCSP (at both protein and gene levels) markedly suppressed after 3 weeks of induction, was upregulated to robust levels upon withdrawal of factors (FIG. 3g).

iPP Cells are Able to Generate Functional CFTR-Expressing Ciliated Epithelium

Cystic fibrosis transmembrane conductance regulator (CFTR), mainly expressed in ciliated epithelium in the lung, encodes a cAMP-regulated chloride channel and plays a role in regulating chloride and water transport (Benharouga M, 2003). To determine whether iPP cells are able to generate CFTR expressing ciliated epithelium, Clara cells generated using a 3-week induction following a 2-week withdrawal, were differentiated in a Matrigel™-based ALI system for 2-3 weeks (FIG. 10a). ALI-conditioned cells were stained with b-tubulin IV for cilia formation with the majority of the cells staining positively (FIG. 4b). It was found that at least 60% of E-cadherin+ cells expressed CFTR, indicating the formation of functional ciliated epithelium with tight junctions (FIG. 4c). X-Z projections of horizontal optical sections confirmed the apical membrane localization of CFTR while E-cadherin staining was visualized at the lateral membranes (FIG. 4d). Flow cytometry analysis showed that ALI-conditioning resulted in CFTR expressing cells (FIG. 4e). Gene expression analysis of ALI-conditioned cells compared to pre-ALI cells (3-week induction+2-week withdrawal cells) showed a reduction of CCSP expression but a marked up-regulation of Foxj1 and CFTR (FIG. 4g), suggesting the appropriate differentiation of expanded Clara cells (pre-ALI) to CFTR-expressing ciliated cells (ALI). An iodide efflux assay measuring cAMP agonist stimulation of the CFTR channel showed iPP-derived ciliated epithelium possess cAMP-regulated CFTR activity (FIG. 4f). Together, these results show the optimized transient induction can not only achieve expansion of Clara cells, but also preserve the differentiation potential of parental Clara cells to generate functional CFTR-expressing ciliated cells.

EpCAM$^{high}$-Derived iPP Cells are Useful as a Component of Cell Replacement Therapy for Cystic Fibrosis In Vivo.

ROSA26-rtTA/Col1a1::tetO-4F2A double transgenic mice were bred to actin GFP mice and GFP+ Clara cells isolated and subjected to the iPP protocol. To test their ability to engraft in CFTR-deficient epithelium in vivo, GFP-iPP cells were delivered to CFTR-knockout mice by transtracheal injection. Recipient mice were treated with a conditioning regimen previously shown (Duchesneau P et al., 2010) to augment retention of delivered cells. Lung tissues were harvested at 7 and 21 days after cell delivery for further evaluation. The localization and differentiation of engrafted cells were assessed by dual-label immunohistochemstry staining with anti-GFP and anti-CFTR antibodies. CFTR expression in airways of wildtype mice and naphthalene-treated CFTR-knockout mice served as positive and negative controls (FIG. 5a-d), respectively. Confocal images showed CFTR expression on the surface of engrafted GFP cells at both day 7 (FIG. 5e) and 21 (FIG. 5f), suggesting the successful differentiation of iPP cells to CFTR-expressing cells in vivo. CFTR protein was confirmed in CFTR-knockout mouse lungs treated with this cell replacement regimen by Western blotting (FIG. 5g).

Genomic expression of CFTR was quantified (relative to lungs from CFTR wildtype mice) and used as a measure of cell retention. Donor iPP cells were able to survive and engraft in recipient lungs (FIG. 5h) with no significant difference in cell retention between lungs 3 weeks after cell delivery compared to 1 week. Gene expression analysis showed that iPP cells were able to partially restore the expression of CCSP, Foxj1 and CFTR in treated CFTR-deficient lungs. Three-week iPP treatment resulted in a reduction of CCSP expression and a significant increase in Foxj1, indicating the likely differentiation of Clara cells, whether endogenous or derived from the iPP protocol, to ciliated cells in vivo (FIG. 5i). Sustained rather than upregulated CFTR expression in the 3-week treatment group was expected given recipient-derived ciliated cells are CFTR-deficient.

Transient Induction Allows Preservation of Lineage Preference and Commitment

For therapeutic applicability, lineage restriction is critical. Thus an in vitro teratoma assay was used (Levenberg S et al., 2003) to ensure that 3-week induced iPP cells have restricted differentiation capacity. Lineage differentiation was accessed by immunostaining for Pan-CK (endoderm epithelial cell marker), α-actinin (mesoderm cardiomyocyte marker) and β-tubulin III (ectoderm neuron cell marker) and demonstrated that 3-week induced iPP cells remain committed to an epithelial lineage (FIG. 6a). In contrast, long term-induced cells (>8 weeks), in addition to showing Pan-CK expression (FIG. 6b), were able to generate α-actinin+(FIG. 6c) and β-tubulin III+ (FIG. 6e) cells. Nanog-positive undifferentiated cells were also observed (FIG. 6d). It was also found that 3-week induced iPP cells exhibited a higher tendency for generation of ciliated cells (β-tubulin IV+: 66.7%±7.64% cells) compared to long term-induced cells (>8 weeks) (β-tubulin IV+: 25%±5% cells) (FIG. 6f). The existence of mixed populations of differentiated cells and undifferentiated cells in the long-term induced cell group suggests that prolonged induction results in divergence from the original lineage and a greater capacity for pluripotency, if not full creation of traditional iPS cells.

Discussion

This example shows that transient induction of reprogramming factors can induce quiescent EpCAM$^{high}$ cells to proliferate which can be regulated by withdrawal of the inductive factors. EpCAM$^{high}$-derived, transiently-induced cells have the capability of returning to their original phenotype upon withdrawal of reprogramming factors. In vitro, they can differentiate to generate functional CFTR expressing ciliated epithelium and repopulate CFTR-knockout epithelium in vivo after a recipient conditioning regimen. These results show that transient reprogramming is not only able to achieve expansion of the selected mature cell type, but also preserves the differentiation potential of the parental population to generate functional progeny.

The novel iPP reprogramming strategy disclosed herein exploits factor-dependent proliferation, (distinct from factor-independent proliferation of iPS and ES cells), present in the earlier phases of reprogramming allowing the generation of large numbers of epithelial cells without reaching the pluripotent state. Recent advances in the understanding of the mechanisms involved in iPS reprogramming have demonstrated that "epigenetic memory" found both in human and mouse iPS cells renders iPS cells permissive to preferred differentiation to the lineage of the cell of origin (Chin M H et al., 2009; Ghosh Z et al., 2010; Marchetto M C N et al, 2009). In this study, the "residual" epigenetic memory of the starting material en route to a stable conversion to iPS cells was harnessed.

Despite significant effort put forth to generate lung epithelium using embryonic (ES) stem cells (Denham M et al., 2007; Rippon H J et al, 2004; Van Vranken B E et al., 2007) and current progress in directed differentiation studies using ES and iPS cells (Mou H et al., 2012; Wong A P et al., 2012; Christodoulou C et al., 2011; Longmire T A et al., 2012) cells, the therapeutic use of these cells remains hindered by low yields and insufficient purity of mature cell types as well as safety issues resulting from potential teratoma formation in vivo. Two recent studies showed in vitro differentiation of iPS and ESCs to lung epithelium (Mou H et al., 2012; Wong A P et al., 2012), but were not able to generate large numbers of either Clara cells or ciliated cells. Importantly neither group has evaluated the in vivo contribution of resultant cell types in a model of cell replacement therapy. On the contrary, the iPP cells disclosed herein hold the potential for treating respiratory diseases and can give rise to both Clara cells and ciliated cells. In vivo studies showing successful retention and localization in CFTR-deficient epithelium highlight the therapeutic potential of iPP cells. Also, since iPP cells are not fully reprogrammed, they appear not to be pluripotent compared to traditional iPS cells and thus likely not tumorigenic. Cyclical transient induction using intermittent doxycycline treatment can be used to obtain greater cell numbers This study shows the generation of induced lung epithelial progenitor cells with controlled proliferation and lineage-restricted differentiation. The iPP concept is broadly applicable and can be extended to other somatic cell types giving rise to numerous progenitor cell populations (Hanna J et al., 2009).

Methods Summary

Animal Husbandry

ROSA26-rtTA and Col1a1: tetO-4F2A mice (Jackson Laboratory, 011004) were used to generate inducible lung epithelial cells. Animals were maintained as an in-house breeding colony under specific pathogen-free conditions.

Naphthalene Administration and Cell Delivery

Adult (6- to 8-week-old) female CFTR-knockout mice (Jackson's lab) were used for naphthalene treatment studies.

Naphthalene (>99% pure; Sigma-Aldrich, St Louis, Mo.) was dissolved in Mazola corn oil and injected intra-peritoneally between 8:00 and 10:00 A.M. at a dose of 200 mg/kg as previously described (Stripp et al., 1995). Busulfan (Otsuka America Pharmaceutical, Rockville, Md.) was given by intra-peritoneal injection 1 day after naphthalene treatment at a dose of 20-50 mg/kg and donor cells were transplanted the following day (106 cells in 50 µl PBS) transtracheally using sterile gel-loading tips. The mice received donor cells were rotated to ensure equal dispersion of cell suspension to both lungs.

Isolation of Clara Cells from Mouse Lung

Mice were injected intra-peritoneally with heparin (250 U/mouse) and by CO2 narcosis. Lungs were perfused through the right ventricle with cold phosphate buffered saline (PBS) (~10 mL) to remove blood by directing the catheter towards the main pulmonary artery. Endo-bronchial lavage was then performed to remove alveolar leukocytes. Clara cells were isolated using a previously described protocol (Atkinson, 2008) with modifications. Briefly, lungs were instilled with 0.5 mL of 1% low melting temperature agarose in PBS through the trachea then placed on ice for 2 min. For lung digestion, 0.5~1 mL of 0.25% trypsin was instilled into the trachea followed by ligation of the trachea with a suture. Lungs were incubated for 10 min at 37° C., then lung tissue was teased away from the large airways, finely minced to 1 mm2 pieces and placed in 250 µg/mL of DNAse I in DMEM containing antibiotic for 10 min minutes. The suspension was transferred to a 50 mL tube, and FBS was added to 10% of final volume. The suspension was sieved through 100 and 40 µm nylon meshes and centrifuged at 200 g for 10 minutes. The cell pellet was re-suspended in red blood cell lyses buffer for 3 min and the lysing was stopped by addition of an equal volume of PBS. Cells were centrifuged at 40 g for 6 min then re-suspended in 10% FBS-DMEM and centrifuged 2 more times at 40 g for 6 min. The final pellet was suspended in 0.5% vol/vol FBS-PBS for all subsequent procedures.

Fluorescence Activated Cell Sorting and Analysis

For purification of epithelial cells, fresh isolated cells were suspended and incubated in 0.5% vol/vol FBS-PBS containing an optimally pre-titered mixture of antibodies [anti-CD45, anti-CD31 (BD Biosciences), anti-EpCAM (Abcam) and relevant isotype controls] for approximately 30 min on ice. Labeled cells were washed in 0.5% vol/vol FBS-PBS, re-suspended at 3~5×106 cells/mL. Cell viability was accessed by propidium iodide (1 µg/mL) staining. For intra-cellular antigen analysis, cells were fixed and stained using a Fix and Perm kit (Invitrogen) as per manufacturer instructions. Sorting was performed using a Moflo BRU cell sorter (Becton Dickinson), acquisition was performed using a BD LSRII analyzer (Becton Dickinson) and data was analyzed using FlowJo software.

Immunofluorescence

Immunoreactivity of different antigens was evaluated using immunofluorescence techniques. Briefly, samples were fixed with 4% paraformaldehyde (PFA) for 30 min and blocked with 5% goat serum and 2% BSA in PBS containing 0.5% Triton X-100 for 1 hour. Primary antibodies were diluted in BSA/PBS, applied to samples and incubated overnight at 4° C. Secondary antibodies AlexaFluors 488, 532, 546, 633 or 647 (Invitrogen) were applied according to the species in which the primary antibody was used for 2 hours at room temperature. Nuclear staining was performed using 2 mg/ml 4, 6, diamidino-2-phenylindole (DAPI; Sigma). Stained samples were mounted with immunofluorescent mounting medium (DAKO). Appropriate non-specific IgG isotypes were used as controls. Immunoreactivities of antigens were visualized as single optical planes using an Olympus Fluoview confocal microscope and analyzed using FV10-ASW 2.0 Viewer software.

Real-Time PCR Analysis

Total RNA was prepared using the RNeasy® Kit (Qiagen) as per manufacturer's instructions. cDNA was prepared and assayed using Superscript® III (Sigma) according to manufacturer's protocol. Differential gene expression was determined using SYBR® green detection (Roche). All Real-time PCR reactions were done in triplicate for each sample. GAPDH was used as a housekeeping gene to normalize gene expression levels using LightCycler® 480 software (Roche). Normalized mRNA levels were shown as relative to the control samples (day 0 fresh isolated cells or adult lung).

Cell Culture

Bottom-Feeder Conditioned CFSE Assay

CFSE (carboxyfluorescein diacetate, succinimidyl ester) cell proliferation assay was used to evaluate proliferative capacity. To separate seeded cells from feeders, a previously described 18 bottom-feeder seeding method was applied. Mitomycin treated in-activated mouse embryonic fibroblast (MEF) feeders were seeded and allowed to attach to the bottom of the Transwell® (Corning) membrane one day prior to addition of sorted cells on the top of the membrane. CFSE working solution (10-15 µM/106 cells; Invitrogen) was prepared and applied to cells according to the manufacturer's protocol. Cell were labelled with CFSE and analyzed using flow cytometry.

Matrigel™-Based iPP Induction

Feeders (MEF) were seeded on 0.1% gelatin coated 24-well Transwell® filter inserts (Corning) one day prior to the addition of epithelial cells. Sorted epithelial cells resuspended in 100 µL of Matrigel™ (BD Biosciences) prediluted 1:1 (vol/vol) with epithelial-specific (EpiS) media were added to a MEF-coated 24-well Transwell® filter inserts in a 24-well tissue culture plate containing 500 µL of epithelial media for 3-5 days then replaced with ES (embryonic stem cell) medium containing 1.5 ug/ml Doxycycline (Sigma). EpiS medium comprised of DMEM/F12 (Invitrogen) supplemented with 10% FBS, penicillin/streptomycin, 10 mg/ml insulin, 5 mg/ml transferring-selenium (Sigma), epidermal growth factor (EGF, 20 ng/mL; Sigma), fibroblast growth factor-10 (FGF-10, 50 ng/mL; R&D Systems) and hepatocyte growth factor (HGF, 30 ng/mL; R&D Systems). Media was replenished three times per week. For bulk passaging, whole cultures were dissociated in Collagenase (1 mg/ml; Sigma)/Dispase (3 mg/ml; BD Biosciences) in PBS to generate a single-cell suspension. For clonal passaging, single colonies were picked and dissociated in the Collagenase/Dispase solution.

In Vitro Differentiation Assays

In order to examine the in vitro potential of these cells to differentiate along certain lineages a variety of differentiation assays were performed. iPP cells induced for 3 weeks were compared to a positive control group consisting of cells exposed to reprogramming factors for 8 weeks.

Air-Liquid Interface (ALI) Differentiation Assay

To evaluate generation of ciliated cells, a novel 3D Matrigel™-based ALI system was developed which allows the differentiation to occur with support of feeder cells, thereby enhancing the efficiency of ciliogenesis. Prior to the ALI assay, induced cells were cultured and recovered in ES medium for 2 weeks. For ALI culture, the ES medium from upper chamber was removed in order to expose cells to the air while medium in lower chamber was replaced with ALI-specific medium (Lonza). Media was replenished 2 times per week and cells were maintained under ALI conditions for 2-3 weeks.

In Vitro Pluripotency Assay

In vitro pluripotency formation was done using a previously described protocol 20. Briefly, 3-week and over 8-week induced cells were dissociated then re-suspended in 50% (Matrigel) and 20% FBS containing medium supplemented with the following growth factors: activin-A (20 ng/ml), transforming growth factor (TGF)-b1 (2 ngml), 10 g/ml insulin, 5 g/ml transferrin and retinoic acid (RA) (300 ng/ml) for 2-3 weeks. Lineage differentiation was accessed by immunostaining for Pan-Cytokeratin (endoderm epithelial cell marker), a-actinin (mesoderm cardiomyocyte marker) and b-tubulin III (ectoderm neuron cell marker).

Neuron Differentiation Assay

To determine the lineage commitment of induced cells, a defined neuron differentiation assay (Millipore) was performed with slight modifications. Briefly, 3-week and >8-week induced cells from Matrigel™ cultures were digested to single cell suspension and differentiated under neuron-specific conditions for 2-3 weeks following the manufacturer's protocol. Generation of neurons was accessed by immunostaining of b-tubulin III.

Iodide Efflux Assay

ALI-conditioned cells cultured on Transwell® membranes were loaded with 500 μl NaI solution [3.0 mM KNO3, 2.0 mM Ca(NO3)2, 11 mM glucose, 20 mM HEPES, 136 mM NaI] from the bottom chamber and incubated at 37° C. for 1 h. To remove the redundant iodide, cultures were washed out with 5 times 1 ml of washing buffer comprised of nitrate (3.0 mM KNO3, 2.0 mM Ca(NO3)2, 11 mM glucose, 20 mM Hepes, 136 mM NaNO3) and 100 μM amiloride. For time course measurement, 200 μl of washing buffer was added to the top chamber of Transwell®s at one-minute intervals for 3 minutes followed by adding 200 μl of cAMP agonists which contain forskolin (10 μM), 3-isobutyl-1-methylxanthine (100 μM, IBMX), and genistein (50 μM) in washing buffer at one-minute intervals for 6 minutes. Reacted solutions at each minute were transferred to a 96-well plate to measure the absolute iodide electrode value (mV) using halide-selective microelectrode (Lazar Research Laboratories, Los Angeles, Calif.). Measured mV values were converted to iodide concentrations using a standard curve measuring the mV values of 1 μM to 1 mM iodide.

Statistics

Statistical analysis was performed using GraphPad Prism 5.0 statistical software (San Diego, Calif., USA). The statistical significance of multiple groups was compared to each other using Tukey's multiple comparison test ANOVA. A p value of <0.05 was considered significant.

Example 9

Cyclical Transient Induction

Cyclic induction in which iPP cells undergo numerous (>1) repeats of transient induction may result in greater expansion than that obtained using only a one-time exposure to reprogramming factors. Cyclic induction was evaluated in vitro (up to 3 cycles) and in vivo (up to 2 cycles).

Figure 17:
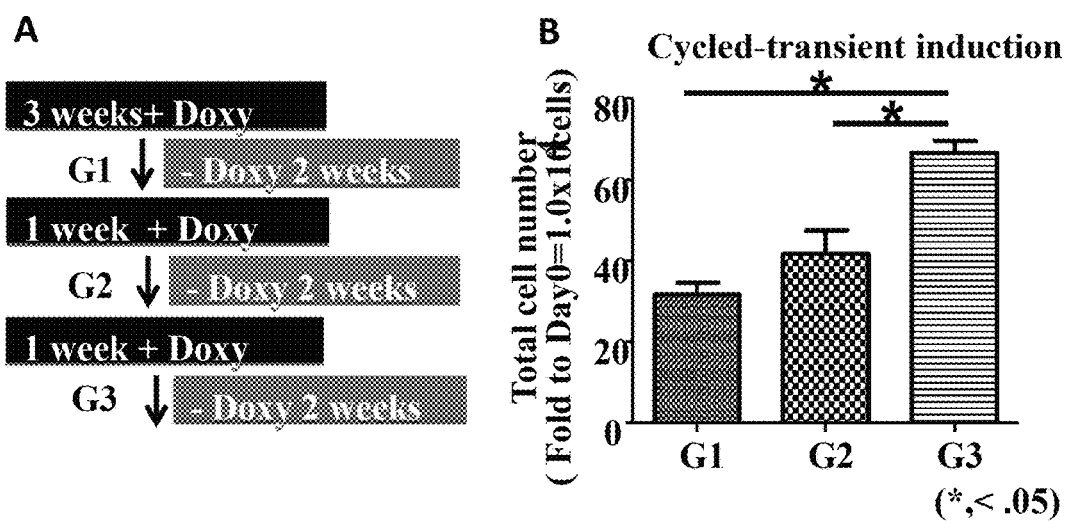
FIG. 17. Scheme (A) and graph (B) for cyclic induction.

For in vitro cyclic induction, $Epcam^{high}$ derived iPP cells were cultured without doxycycline for 2 weeks ($1^{st}$ cycle) and then received a second doxycycline exposure for 1 week followed by another 2 weeks without doxycycline ($2^{nd}$ cycle). This was done for one additional cycle ($3^{rd}$ cycle) (FIG. 17). Characterization of cells after each cycle will be performed. Results showed a progressive increase in the number of expanded cells and statistical significance after 3 cycles (compared to $1^{st}$ and $2^{nd}$ cycles; one-way ANOVA—turkey post-hoc test; p<0.05; n=3).

In order to determine whether cyclic transient induction in vivo (one cycle of in vivo induction after one cycle of in vitro induction) could expand engrafted iPP cells, male iPP cells were delivered to female naphthalene-treated BL6 mice and treated them with or without doxycycline containing water (1 mg/ml) 7 days after cell delivery. Cell engraftment was measured by genomic expression of SRY using qPCR.

Figure 18:
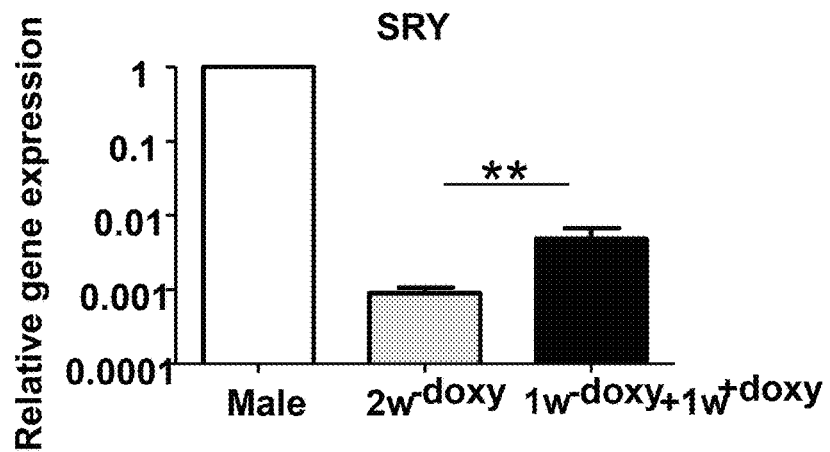
FIG. 18. Graph showing in vivo cyclic induction.

Results showed that cyclic induction could significantly expand engrafted iPP/iPP-derived cells in vivo (FIG. 18). Characterization of in vivo expanded cells will be performed. These results highlight the potential of cyclic induction as a tool to achieve further expansion of target cells. The number of cycles may be optimized to result in greatest expansion, and maintenance of epithelial cell lineage commitment without traversing to pluripotency.

Example 10

The Potential of Cyclic Transient Induction in Repopulating Injured Airway Epithelium In Vivo Transient expression of iPS reprogramming factors in vitro leads to controlled expansion of $EpCAM^{high}$-Clara cells and generates an induced progenitor population (iPP). iPP cells which are able to generate Clara cells and CFTR-expressing ciliated cells in vitro may for example be used as a component of cell replacement therapy for cystic fibrosis in vivo.

Figure 19:
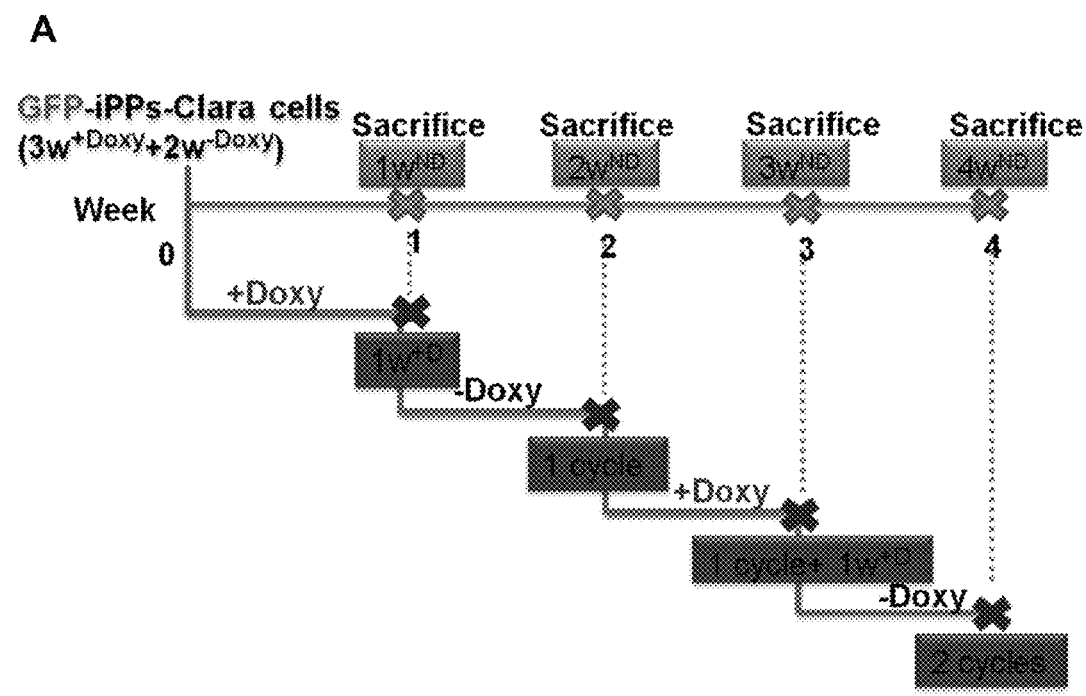
FIG. 19 (A) Scheme showing in vivo doxycycline administration. (B) Cell retention rate of engrafted cells in recipient lungs (% of Day 0 injected cells), was calculated using genomic GFP expression at different time (relative to β-actin GFP lungs) measured by qRT-PCR. (C) The transgene 4F2A of engrafted iPP-derived cells can be activated in vivo. Expression of the transgene construct mCol4F2A. Values are mean±S.D. of triplicate samples. *, p<0.05; , p<0.001; *, p<0.0001. (D). Expression of CCSP of recipient lungs. Values are mean±S.D. of triplicate samples. *, p<0.05; , p<0.001; *, p<0.0001. (E). Confocal microscopy images of iPP cell-treated injured airway sections, BL6 control (top left), 2-week without doxycycline treatment (top right) and cyclical treated lungs (bottom), showing nuclear stain DAPI (blue). GFP (green) and CCSP (red)
Figure 19:
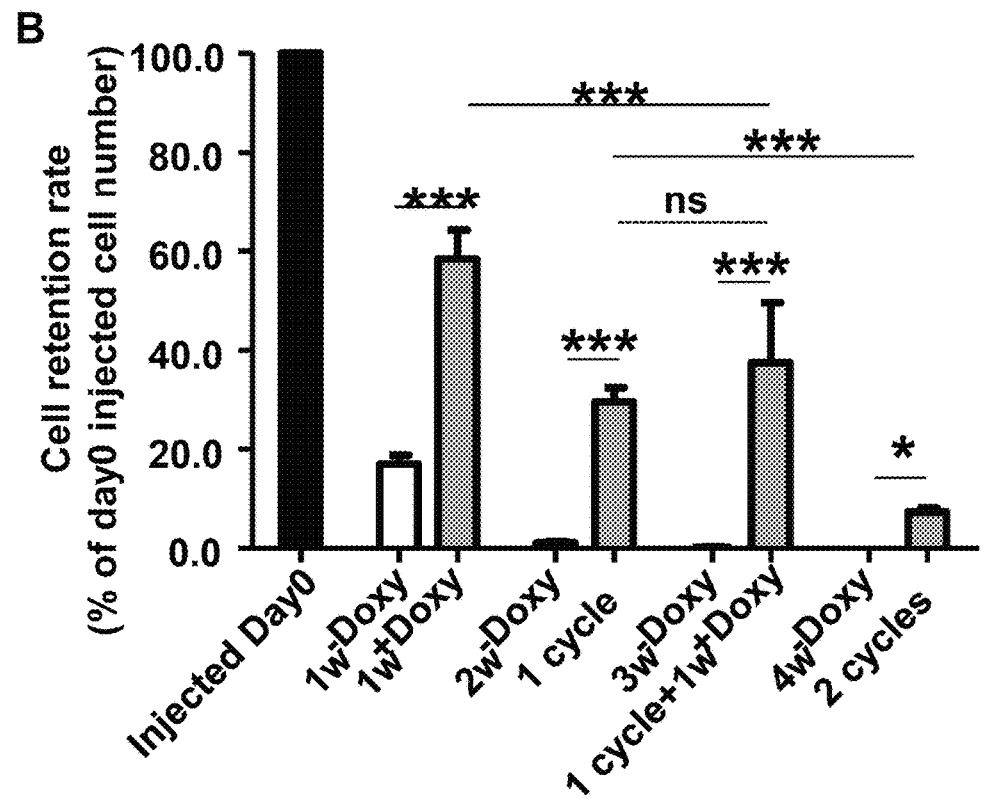
Figure 19:
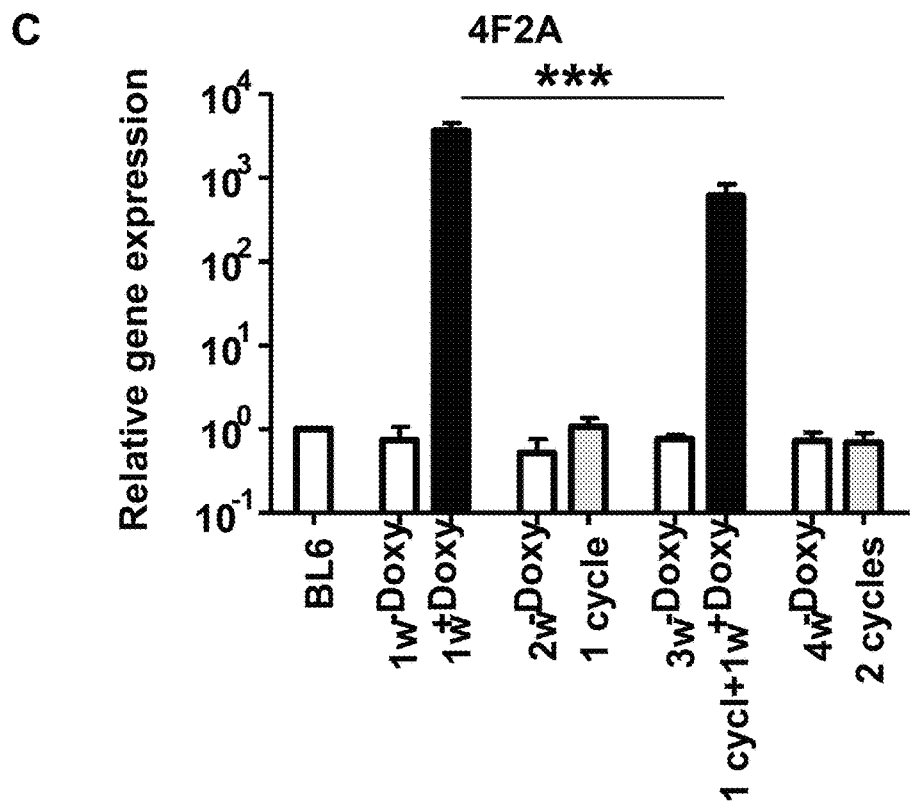
Figure 19:
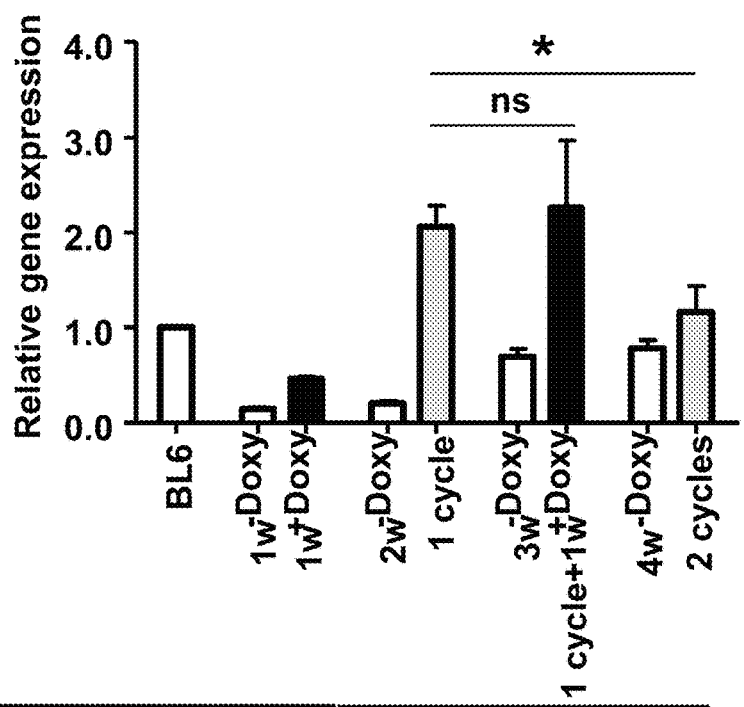
Figure 19:
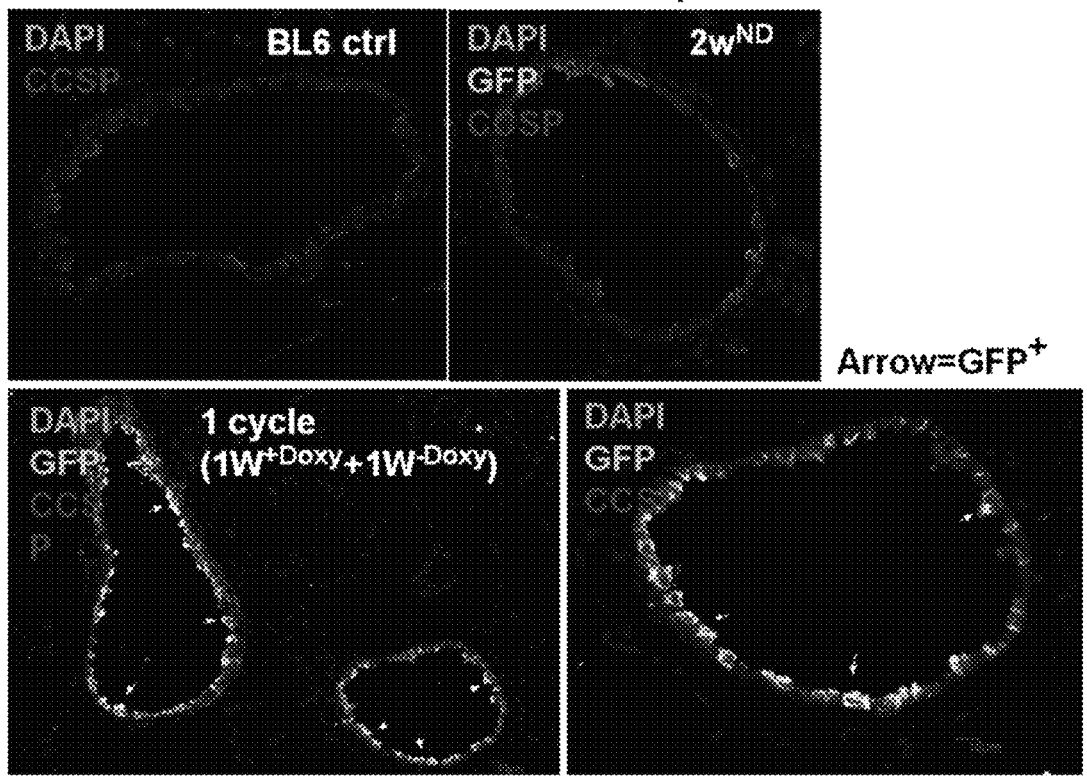

GFP-iPP-Clara cells were intratracheally delivered to naphthalene-busulfan conditioned BL6 recipients. Mice fed with regular food were used as controls. For in vivo cyclic induction, mice were fed with doxycycline contained food (625 μg/g) for 1 week followed by another week without doxycycline ($1^{st}$ cycle). This was done for one additional cycle ($2^{nd}$ cycle) (FIG. 19). Mice under different treatments were sacrificed per week for further evaluation.

Engrafted iPP-Derived Cells can Respond to In Vivo Cyclical Induction

Measurement of cell retention rate of engrafted cells in recipient lungs (FIG. 19B) result showed that the number of engrafted cell gradually decreased in non-doxy-treated groups (1 $W^{-Doxy}$>2 $W^{-Doxy}$>3 $W^{-Doxy}$4 $W^{-Doxy}$) The iPP-derived cells are able to respond to in vivo induction and the number of engrafted cells increased under doxycycline treatment and decreased upon the removal of doxycycline. On a gene expression level, PCR analysis of transgene 4F2A expression (FIG. 19C) showed that it is not expressed in non-induced lungs. It can be activated under doxycycline treatment and down-regulated/silenced upon removal of doxycycline indicating that iPP-derived cells can respond to in vivo induction.

Cyclical Induction can Efficiently Restore CCSP Expression of Recipient Airways

Without in vivo doxycycline treatment, donor iPP-Clara cells quickly undergo differentiation to ciliated cells and they were not able to restore CCSP expression of naphthalene-treated recipient epithelium. In contrast 1 cycle (1 $w^{+D}$+1 $w^{ND}$) induction is already able to restore the CCSP expression of injured epithelium, at a robust level of both gene (FIG. 19D) and protein (FIG. 19E) expression compared to normal BL6 epithelium. However, the expression of the $2^{nd}$ cycle-treated lungs is lower which may due to the fact that the endogenous repair has been activated or completed 4 weeks after naphthalene treatment and less exogenous CCSP-expressing cells were needed.

The current results show that cyclical induction enhances cell replacement potential of engrafted iPP-derived cells.

Example 11 iPP Induction of a Lung Stem Cell Population-AT-II Cells

SftPC$^+$ AEC-II cells function as progenitor cells in the alveoli and proliferate and differentiate into AEC-I cells. These processes, which are normally quite slow, are stimulated after injury (e.g. bleomycin). The number and function of lung airway progenitors decreased or depleted in certain pathological conditions and in age-related decline. In vitro, AT-II cells can give rise to alveolar colonies which possess limited passaging capacity.

It is demonstrated herein that iPP induction is able to rescue the limited passaging capacity of AT-II colonies, and also efficiently expand cells in vitro.

Isolation and Characterization of Mouse AT-II Cells.

AT-II cells were isolated from Col1a14F2A mice using a modified elastase-based protocol. Flow-cytometric analysis of freshly isolated cells stained with anti-SPC and CD74 showed EpCAM$^{low}$ cells are exclusively AT-II cells expressing both markers (FIG. 20B-C).

Induction Protocol (and/or Late Induction) can Rescue the Limited Passaging Capacity of AT-II Colonies An induction condition for AT-II cells progenitor cells involved differentiating the cells in Matrigel for 2 weeks prior to exposing to doxycycline (FIG. 20A). This 2-week "late induction" (2 W$^{ND}$2 W$^{+Doxy}$) significantly increased the colony forming efficiency (FIG. 20D-E) and total number of cells (FIG. 20F). Importantly, these induced colonies are alveolar-like colonies expressing higher level of SPC and EpCAM, compared to non-treated group (FIG. 20G). Furthermore, the differentiation status of colonies were evaluated by immunostaining of AT-I cell marker (T1α). In ND group, AT-I cell markers are greatly up-regulated at both gene (AQP5) and protein (T1α) levels (FIG. 20H), indicating the differentiation of AT-II cells to AT-I cells in vitro. Under late induction, more Spc+ and less T1α+ cells were found, which may suggest the de-differentiation of AT-II derived AT-I cells to the original clonogenic AT-II cells.

The table shows the fold changes of cell number upon iPP induction compared to non-induced groups over time.

2 W$^{ND}$+2 W$^{+D}$+2 W$^{ND}$ refers to the final product. 2 W$^{ND}$: 2-week culture without doxycycline; 4 W$^{ND}$: 4-week culture without doxycycline; 2 W$^{ND}$-2 W$^{+D}$: 2-week without doxycycline followed by 2-week with doxycycline; ND: non-doxycycline treated; +D: doxycycline-treated Next, the changes upon withdrawal of the factors was determined. Although CFU % was reduced upon withdrawal of inductive factors for 2 weeks after a 2-week late induction (2 W$^{ND}$+2 W$^{+Doxy}$+2 W$^{ND}$), it is still significantly higher than that of non-treated groups. Interestingly, average colony size (diameter) became bigger and epithelial-like adherent cells were also found in withdrawal group. Immunostaining showed Spc and EpCAM were well maintained in these large-sized colonies while present at much lower levels in the doxycycline-treated group (2 W$^{ND}$+4 W$^{+Doxy}$) (FIG. 20I). This preliminary data showed that iPP induction is not only able to rescue the limited passaging capacity of AT-II colonies, but also efficiently expand cells (102 fold to day 0).

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims. All publications, patents and patent applications are herein incorporated by reference in their entirety to the same extent as if each individual publication, patent or patent application was specifically and individually indicated to be incorporated by reference in its entirety.

CITATIONS

1. Global Alliance against Chronic Respiratory Diseases. Stop the global epidemic of chronic disease. http://www.who.int/gard/en (accessed Aug. 31, 2010).
2. M. Chilosi, et al. (2010). Epithelial stem cell exhaustion in the pathogenesis of idiopathic pulmonary fibrosis. *Sarcoidosis casculitis and diffuse lung diseases.* 27; 7-18
3. Leigh M. Marsh, et al. (2009). Surface expression of CD74 by type II alveolar epithelial cells: a potential mechanism for macrophage migration inhibitory factor-induced epithelial repair. *Am J Physiol Lung Cell Mol Physiol* 296: L442-L452.
4. Rock, J. R., et al. (2009). Basal cells as stem cells of the mouse trachea and human airway epithelium. *Proc. Natl. Acad. Sci. USA* 106, 12771-12775.
5. Payman Samavarchi-Tehrani, et al. (2010). Functional Genomics Reveals a BMP-Driven Mesenchymal-to-Epithelial Transition in the Initiation of Somatic Cell Reprogramming. *Cell Stem Cell* 7, 64-77.
6. Anna C. Zemke, et al. (2009) Molecular staging of epithelial maturation using secretory cell-specific genes as markers. *Am J Respir Cell Mol Biol Vol* 40. pp 340-348,
7. Woltjen, K. et al. (2009). PiggyBac transposition reprograms fibroblasts to induced pluripotent stem cells. *Nature* 458, 766-770.
8. Fehrenbach H., et al. (2001). Alveolar epithelial type II cell: defender of the alveolus revisited. Respir Res; 2: 33-46.
9. M. Lynn Berndt-Weis. et al. (2009). Global transcriptional characterization of a mouse pulmonary epithelial cell line for use in genetic toxicology. *Toxicology in Vitro* 23, 816-833.
10. Jeffrey J Atkinson. et al. (2008). Clara cell adhesion and migration to extracellular matrix. *Respiratory Research* 10.1186/1465-9921-9-1.
11. Rawlins E L, Hogan B L. Epithelial stem cells of the lung: privileged few or opportunities for many? *Development* 2006; 133:2455-2465.
12. Okubo T, Knoepfler P S, Eisenman R N, Hogan B L. Nmyc plays an essential role during lung development as a dosage-sensitive regulator of progenitor cell proliferation and differentiation. *Development* 2005; 132:1363-1374.
13. Wan H, Dingle S, Xu Y, Besnard V, Kaestner K H, Ang S L, Wert S, Stahlman M T, Whitsett J A. Compensatory roles of foxa1 and foxa2 during lung morphogenesis. J Biol Chem 2005; 280:13809-13816.
14. Shu W, Guttentag S, Wang Z, Andl T, Ballard P, Lu M M, Piccolo S, Birchmeier W, Whitsett J A, Millar S E, et al. Wnt/beta-catenin signaling acts upstream of n-myc, bmp4, and fgf signaling to regulate proximaldistal patterning in the lung. *Dev Biol* 2005; 283:226-239.
15. Lu Y, Thomson J M, Wong H Y, Hammond S M, Hogan B L. Transgenic over-expression of the microrna mir-17-

92 cluster promotes proliferation and inhibits differentiation of lung epithelial progenitor cells. *Dev Biol* 2007; 310:442-453.

16. Rupa S., et al. Role of the murine reprogramming factors in the induction of pluripotency. *Cell* 2009:136, 364-377.

17. Bryce W. Carey, et al. A single-gene transgenic mouse strain for reprogramming adult somatic cells. *Nature Methods* 2010; 7(1): 56-59.

18. Sinae Kim, et al. A novel culture technique for human embryonic stem cells using porous membranes. *Stem cell* 2007; 25:2601-2609.

19. McQualter, et al. Evidence of an epithelial stem/progenitor cell hierarchy in the adult mouse lung. *PNAS* 2010; 107: 1414-1419

20. Shulamit Levenberg, et al. Differentiation of human embryonic stem cells on three-dimensional polymer scaffolds. PNAS 2003; 22: 12741-12746

21. Stripp B R, et al. Plasticity of airway cell proliferation and gene expression after acute naphthalene injury. *Am J Physiol* 1995; 269(6 Pt 1): L791-9.

22. Yin L, et al. Induction of vascular progenitor cells from endothelial cells stimulates coronary collateral growth. Circ Res 2012; 110(2): 241-52.

23. Kim K, et al. Epigenetic memory in induced pluripotent stem cells. Nature 2010; 467(7313): 285-90.

24. Polo J M, et al. Cell type of origin influences the molecular and functional properties of mouse induced pluripotent stem cells. Nat Biotechnol 2010; 28(8): 848-55

25. Herridge, M. S. et al. One-year outcomes in survivors of the acute respiratory distress syndrome. The New England journal of medicine 348, 683-693, doi:10.1056/NEJMoa022450 (2003).

26. Wiesen, J., Komara, J. J., Walker, E., Wiedemann, H. P. & Guzman, J. A. Relative cost and outcomes in the intensive care unit of acute lung injury (ALI) due to pandemic influenza compared with other etiologies: a single-center study. Annals of intensive care 2, 41, doi: 10.1186/2110-5820-2-41 (2012).

27. Murray, C. J., Lopez, A. D. & Jamison, D. T. The global burden of disease in 1990: summary results, sensitivity analysis and future directions. Bulletin of the World Health Organization 72, 495-509 (1994).

28. Menzin, J., Boulanger, L., Tang, S., Thakker, K. & Nissen, S. E. Cost analysis of amlodipine versus enalapril in patients with coronary artery disease and normal blood pressure: findings from the CAMELOT economic substudy. Applied health economics and health policy 6, 157-162, doi:10.2165/00148365-200806020-00007 (2008).

29. Vasiliadis, H. M., Collet, J. P., Penrod, J. R., Ferraro, P. & Poirier, C. A cost-effectiveness and cost-utility study of lung transplantation. The Journal of heart and lung transplantation: the official publication of the International Society for Heart Transplantation 24, 1275-1283, doi: 10.1016/j.healun.2004.10.012 (2005). 1. Raiser, D. M. & Kim, C. F.

30. Bertoncello, I. & McQualter, J. L. Endogenous lung stem cells: what is their potential for use in regenerative medicine? *Expert Rev Respir Med* 4, 349-362 (2010).

31. Liu, X., Driskell, R. R. & Engelhardt, J. F. Stem cells in the lung. *Methods in enzymology* 419, 285-321 (2006).

32. Mou, H. et al. Generation of multipotent lung and airway progenitors from mouse ESCs and patient-specific cystic fibrosis iPSCs. *Cell Stem Cell* 10, 385-397 (2012).

33. Wong, A. P. et al. Directed differentiation of human pluripotent stem cells into mature airway epithelia expressing functional CFTRTR protein. *Nat. Biotechnol.* 30, 876-882 (2012).

34. Sridharan, R. et al. Role of the Murine Reprogramming Factors in the Induction of Pluripotency. *Cell* 136, 364-377 (2009).

35. Rawlins, E. L. et al. The Role of Scgb1a1+Clara Cells in the Long-Term Maintenance and Repair of Lung Airway, but Not Alveolar, Epithelium. *Cell Stem Cell* 4, 525-534 (2009).

36. Wernig, M. et al. A drug-inducible transgenic system for direct reprogramming of multiple somatic cell types. *Nat. Biotechnol.* 26, 916-924 (2008).

37. Shao, L. et al. Generation of iPS cells using defined factors linked via the self-cleaving 2A sequences in a single open reading frame. *Cell Res.* 19, 296-306 (2009).

38. Eminli, S. et al. Differentiation stage determines potential of hematopoietic cells for reprogramming into induced pluripotent stem cells. *Nat. Genet.* 41, 968-976 (2009).

39. Hanna, J. et al. Direct cell reprogramming is a stochastic process amenable to acceleration. *Nature* 462, 595-601 (2009).

40. Hackett, B. P. & Gitlin, J. D. Cell-specific expression of a Clara cell secretory protein-human growth hormone gene in the bronchiolar epithelium of transgenic mice. *Proc. Natl. Acad. Sci. U.S.A.* 89, 9079-9083 (1992).

41. Tsao, P.-N. et al. Notch signaling controls the balance of ciliated and secretory cell fates in developing airways. *Development* 136, 2297-2307 (2009).

42. Williams, M. C., Cao, Y., Hinds, A., Rishi, A. K. & Wetterwald, A. T1 alpha protein is developmentally regulated and expressed by alveolar type I cells, choroid plexus, and ciliary epithelia of adult rats. *Am. J. Respir. Cell Mol. Biol.* 14, 577-585 (1996).

43. Rawlins, E. L. & Hogan, B. L. M. Ciliated epithelial cell lifespan in the mouse trachea and lung. *AJP: Lung Cellular and Molecular Physiology* 295, L231-L234 (2008).

44. Parish, C. R. Fluorescent dyes for lymphocyte migration and proliferation studies. *Immunol. Cell Biol.* 77, 499-508 (1999).

45. Benharouga, M. The Role of the C Terminus and Na+/H+ Exchanger Regulatory Factor in the Functional Expression of Cystic Fibrosis Transmembrane Conductance Regulator in Nonpolarized Cells and Epithelia. *Journal of Biological Chemistry* 278, 22079-22089 (2003).

46. Duchesneau, P., Wong, A. P. & Waddell, T. K. Optimization of Targeted Cell Replacement Therapy: A New Approach for Lung Disease. *Molecular Therapy* 18, 1830-1836 (2010).

47. Amabile, G. & Meissner, A. Induced pluripotent stem cells: current progress and potential for regenerative medicine. *Trends Mol Med* 15, 59-68 (2009).

48. Wu, S. M. & Hochedlinger, K. Harnessing the potential of induced pluripotent stem cells for regenerative medicine. *Nat. Cell Biol.* 13, 497-505 (2011).

49. Sommer, C. A. & Mostoslaysky, G. The evolving field of induced pluripotency: recent progress and future challenges. *J. Cell. Physiol.* 228, 267-275 (2013).

50. Plath, K. & Lowry, W. E. Progress in understanding reprogramming to the induced pluripotent state. *Nat. Rev. Genet.* 12, 253-265 (2011).

51. Ben-David, U. & Benvenisty, N. The tumorigenicity of human embryonic and induced pluripotent stem cells. *Nat. Rev. Cancer* 11, 268-277 (2011).

52. Pfisterer, U. et al. Direct conversion of human fibroblasts to dopaminergic neurons. *Proc. Natl. Acad. Sci. U.S.A.* 108, 10343-10348 (2011).
53. Caiazzo, M. et al. Direct generation of functional dopaminergic neurons from mouse and human fibroblasts. *Nature* 476, 224-227 (2011).
54. Ambasudhan, R. et al. Direct reprogramming of adult human fibroblasts to functional neurons under defined conditions. *Cell Stem Cell* 9, 113-118 (2011).
55. Chin, M. H. et al. Induced pluripotent stem cells and embryonic stem cells are distinguished by gene expression signatures. *Cell Stem Cell* 5, 111-123 (2009).
56. Ghosh, Z. et al. Persistent Donor Cell Gene Expression among Human Induced Pluripotent Stem Cells Contributes to Differences with Human Embryonic Stem Cells. *PLoS ONE* 5, e8975 (2010).
57. Marchetto, M. C. N. et al. Transcriptional Signature and Memory Retention of Human-Induced Pluripotent Stem Cells. *PLoS ONE* 4, e7076 (2009).
58. Denham, M. et al. A murine respiratory-inducing niche displays variable efficiency across human and mouse embryonic stem cell species. *Am. J. Physiol. Lung Cell Mol. Physiol.* 292, L1241-1247 (2007).
59. Rippon, H. J., Ali, N. N., Polak, J. M. & Bishop, A. E. Initial observations on the effect of medium composition on the differentiation of murine embryonic stem cells to alveolar type II cells. *Cloning Stem Cells* 6, 49-56 (2004).
60. Van Vranken, B. E., Rippon, H. J., Samadikuchaksaraei, A., Trounson, A. O. & Bishop, A. E. The differentiation of distal lung epithelium from embryonic stem cells. *Curr Protoc Stem Cell Biol* Chapter 1, Unit 1G.1 (2007).
61. Christodoulou, C. et al. Mouse ES and iPS cells can form similar definitive endoderm despite differences in imprinted genes. *J. Clin. Invest.* 121, 2313-2325 (2011).
62. Longmire, T. A. et al. Efficient derivation of purified lung and thyroid progenitors from embryonic stem cells. *Cell Stem Cell* 10, 398-411 (2012).
63. Brook B. Cole, et al. (2010) Tracheal Basal Cells A Facultative Progenitor Cell Pool Am J Pathol. 177(1): 362-376
64. Lin, H., Li, H., Cho, H. J., Bian, S., & Roh, H. J. (2007). Air-liquid interface (ALI) culture of human bronchial epithelial cell monolayers as an in vitro model for airway drug transport studies. *J Pharm Sci.* 2007 February; 96(2):341-50. Kesimer, M., Kirkham, S., Pickles, R. J., Henderson, A. G., Alexis, N. E., Demaria, G., et al. (2009). Tracheobronchial air-liquid interface cell culture: a model for innate mucosal defense of the upper airways? *American Journal of Physiology. Lung Cellular and Molecular Physiology,* 296(1), L92-L100. doi:10.1152/ajplung.90388.2008.
65. Roszell, B. et al. Efficient derivation of alveolar type II cells from embryonic stem cells for in vivo application. *Tissue Eng. Part A* 15, 3351-3365 (2009).
66. Cortiella, J. et al. Tissue-engineered lung: an in vivo and in vitro comparison of polyglycolic acid and pluronic F-127 hydrogel/somatic lung progenitor cell constructs to support tissue growth. *Tissue Eng.* 12, 1213-1225 (2006).
67. Jensen, T. et al. A rapid lung de-cellularization protocol supports embryonic stem cell differentiation in vitro and following implantation. *Tissue Eng. Part C Methods* 18, 632-646 (2012).
68. Li, M. et al. Co-electrospun poly(lactide-co-glycolide), gelatin, and elastin blends for tissue engineering scaffolds. *J. Biomed. Mater. Res. A* 79, 963-973 (2006).
69. Takahashi, K. & Yamanaka, S. Induction of Pluripotent Stem Cells from Mouse Embryonic and Adult Fibroblast Cultures by Defined Factors. *Cell* 126, 663-676 (2006).
70. Soh, B. S. et al. CD166(pos) subpopulation from differentiated human ES and iPS cells support repair of acute lung injury. *Mol. Ther. J. Am. Soc. Gene Ther.* 20, 2335-2346 (2012).
71. Yang, K.-Y. et al. IV delivery of induced pluripotent stem cells attenuates endotoxin-induced acute lung injury in mice. *Chest* 140, 1243-1253 (2011).
72. Imaizumi, M. et al. Evaluation of the use of induced pluripotent stem cells (iPSCs) for the regeneration of tracheal cartilage. *Cell Transplant.* 22, 341-353 (2013). González F, Boué S, Izpisúa Belmonte J C. Methods for making induced pluripotent stem cells: reprogramming à la carte. Nat Rev Genet. 2011 April; 12(4):231-42.
73. Onorati, M. et al. Neuropotent self-renewing neural stem (NS) cells derived from mouse induced pluripotent stem (iPS) cells. *Mol. Cell. Neurosci.* 43, 287-295 (2010).
74. Nagai, K. et al. Long-term culture following ES-like gene-induced reprogramming elicits an aggressive phenotype in mutated cholangiocellular carcinoma cells. *Biochem. Biophys. Res. Commun.* 395, 258-263 (2010).
75. Kim, K. et al. Epigenetic memory in induced pluripotent stem cells. *Nature* 467, 285-290 (2010).
76. Kunisato, A. et al. Generation of induced pluripotent stem cells by efficient reprogramming of adult bone marrow cells. *Stem Cells Dev.* 19, 229-238 (2010).
77. Guo, G. et al. Klf4 reverts developmentally programmed restriction of ground state pluripotency. *Dev. Camb. Engl.* 136, 1063-1069 (2009).
78. Prigione, A., Fauler, B., Lurz, R., Lehrach, H. & Adjaye, J. The senescence-related mitochondrial/oxidative stress pathway is repressed in human induced pluripotent stem cells. *Stem Cells Dayt. Ohio* 28, 721-733 (2010).
79. Wolfrum, K. et al. The LARGE principle of cellular reprogramming: lost, acquired and retained gene expression in foreskin and amniotic fluid-derived human iPS cells. *Plos One* 5, e13703 (2010).
80. Aasen, T. et al. Efficient and rapid generation of induced pluripotent stem cells from human keratinocytes. *Nat. Biotechnol.* 26, 1276-1284 (2008).
81. Seki, T. et al. Generation of induced pluripotent stem cells from human terminally differentiated circulating T cells. *Cell Stem Cell* 7, 11-14 (2010).
82. Lin, S.-L. et al. Mir-302 reprograms human skin cancer cells into a pluripotent ES-cell-like state. *RNA* 14, 2115-2124 (2008).
83. Lin, S.-L. et al. Regulation of somatic cell reprogramming through inducible mir-302 expression. *Nucleic Acids Res.* 39, 1054-1065 (2011).

The invention claimed is:

1. A method of obtaining cells expressing pan-cytokeratin (Pan-CK), comprising the steps:
   a) obtaining EpCAM$^{high}$ Clara cells comprising a nucleic acid sequence encoding Oct4, Klf4, Sox2 and cMyc each of which is under the control of an inducible promoter responsive to an inducing agent;
   b) culturing the cells obtained in step a) in embryonic stem (ES) cell medium in the presence of the inducing agent;
   c) culturing the cells obtained in step b) in epithelial medium in the absence of the inducing agent such that cells expressing Pan-cytokeratin (Pan-CK) and Clara cell secretory protein (CCSP) but not Nanog are obtained.

2. The method of claim 1, wherein the nucleic acid sequence further encodes Lin28 operably linked to the inducible promoter.

3. The method of claim 1, wherein obtaining the EpCAM$^{high}$ Clara cells comprises the steps:
   a) isolating the EpCAM$^{high}$ Clara cells from a mammal;
   b) transfecting or transducing the EpCAM$^{high}$ Clara cells with a nucleic acid molecule encoding Oct4, Klf4, Sox2 and c-Myc each under the control of an inducible promoter responsive to an inducing agent.

4. The method of claim 1, wherein the inducible promoter is a tet-on or a tet-off promoter and the inducing agent is tetracycline or doxycycline.

5. The method of claim 1, wherein the cells in step b) are cultured in the presence of the inducing agent for a time period: i) of less than 12, 10, 8, 6, 5, 4, 3, 2 or 1 week; or ii) that causes the number of cells to increase at least 5, 10, 20, 30, 50- or 100-fold compared to the starting population.

6. The method of claim 1, wherein step c) comprises washing the cells obtained in step b) prior to culturing in the absence of the inducing agent.

7. The method of claim 1, wherein the cells in step b) are cultured with feeder cells optionally wherein the feeder cells are separated from the cells of step b) with a membrane.

8. The method of claim 1, wherein step c) comprises culturing the cells in step b) in epithelial medium in the absence of inducing agent for less than 6, 5, 4, 3, 2 or 1 week.

9. The method of claim 1, wherein the EpCAM$^{high}$ Clara cells are obtained by:
   i) isolating the EpCAM$^{high}$ Clara cells from a mammal, and
   ii) transfecting the EpCAM$^{high}$ Clara cells with an exogenous nucleic acid sequence encoding Oct4, Sox2, Klf4, and cMyc each of which is under the control of an inducible promoter responsive to an inducing agent.

10. The method of claim 1, wherein the cells obtained after completion of step c) express each of the lineage markers EpCAM, E-Cadherin and Claudin10 in addition to Pan-CK and CCSP.

* * * * *